(12) United States Patent
Casewell et al.

(10) Patent No.: US 12,285,408 B2
(45) Date of Patent: Apr. 29, 2025

(54) METHODS AND COMPOSITIONS FOR THE TREATMENT OF SNAKE BITE

(71) Applicants: Liverpool School of Tropical Medicine, Liverpool (GB); Stichting VU, Amsterdam (NL)

(72) Inventors: Nicholas Casewell, Liverpool (GB); Laura-Oana Albulescu, Liverpool (GB); Jeroen Kool, Amsterdam (NL)

(73) Assignees: Liverpool School of Tropical Medicine, Liverpool (GB); Stichting VU, Amsterdam (NL)

( * ) Notice: Subject to any disclaimer, the term of this patent is extended or adjusted under 35 U.S.C. 154(b) by 0 days.

(21) Appl. No.: 17/744,502

(22) Filed: May 13, 2022

(65) Prior Publication Data

US 2023/0054792 A1    Feb. 23, 2023

Related U.S. Application Data

(60) Provisional application No. 63/188,586, filed on May 14, 2021.

(51) Int. Cl.
| | | |
|---|---|---|
| *A61K 31/405* | (2006.01) | |
| *A61K 31/10* | (2006.01) | |
| *A61K 31/16* | (2006.01) | |
| *A61P 39/02* | (2006.01) | |

(52) U.S. Cl.
CPC ............ *A61K 31/405* (2013.01); *A61K 31/10* (2013.01); *A61K 31/16* (2013.01); *A61P 39/02* (2018.01)

(58) Field of Classification Search
CPC ...... A61K 31/10; A61K 31/16; A61K 31/405; A61K 31/4054; A61P 39/02
See application file for complete search history.

(56) References Cited

FOREIGN PATENT DOCUMENTS

WO    WO-2016081826 A2 *  5/2016 ............. A61K 31/16

OTHER PUBLICATIONS

Gutierrez, Jose Maria et al.; Snakebite envenoming; Nature Reviews; Disease Primers; vol. 3; article No. 17063; 2017.
Harrison, Robert A. et al.; The time is now: a call for action to translate recent momentum on tackling tropical snakebite into sustained benefit for victims; Liverpool School of Tropical Medicine; Jan. 21, 2019.
Williams, David J. et al.; Strategy for a globally coordinated response to a priority neglected tropical disease: Snakebite envenoming; PLOS Neglected Tropical Diseases; Feb. 21, 2019.
Casewell, Nicholas R. et al.; Medically important differences in snake venom composition are dictated by distinct postgenomic mechanisms; PNAS; vol. 111, No. 25; Jun. 24, 2014.
Tasoulis, Theo et al.; A Review and Database of Snake Venom Proteomes; Clinical Toxicology Research Group; Sep. 18, 2017.
Williams, David J. et al.; Ending the drought: New strategies for improving the flow of affordable, effective antivenoms in Asia and Africa; Journal of Proteomics 74; May 19, 2011.
Arnold, Carrie; The snakebite fight; Nature; vol. 537; Sep. 2016.
Gutierrez, Jose Maria et al.; Global Availability of Antivenoms: The Relevance of Public Manufacturing Laboratories; Toxins; Dec. 24, 2018.
Casewell, Nicholas R. et al.; Pre-Clinical Assays Predict Pan-African Echis Viper Efficacy for a Species-Specific Antivenom; PLOS Neglected Tropical Diseases; vol. 4, issue 10; Oct. 2010.
De Silva; H. Asita et al.; Low-Dose Adrenaline, Promethazine, and Hydrocortisone in the Prevention of Acute Adverse Reactions to Antivenom following Snakebite: A Randomised, Double-Blind, Placebo-Controlled Trial; PLOS Medicine; vol. 8, issue 5; May 2011.
Mohapatra Bijayeeni et al.; Snakebite Mortality in India: A Nationally Representative Mortality Survey; PLOS Neglected Tropical Diseases; vol. 5, issue 4; Apr. 2011.
Bulfone, Tommaso C. et al.; Developing Small Molecule Therapeutics for the Initial and Adjunctive Treatment of Snakebite; Journal of Tropical Medicine; Jul. 30, 2018.
Knudsen, Cecilie et al.; Recent Advances in Next Generation Snakebite Antivenoms; Tropical Medicine and Infections Disease; Apr. 15, 2018.
Otero-Patino, Rafael; Epidemiological, clinical and therapeutic aspects of Bothrops asper bites; Toxicon; Jul. 8, 2009.
Kumar, KG Sajeeth et al.; Clinical and epidemiologic profile and predictors of outcome of poisonous snake bites—an analysis of 1,500 cases from a tertiary care center in Malabar, North Kerala, India; International Journal of General Medicine; 2018.
Slagboom, Julien et al.; Haemotoxic snake venoms: their functional activity, impact on snakebite victims and pharmaceutical promise; British Journal of Haematology; Feb. 24, 2017.
Gutierrez, Jose Maria et al.; Snake venom metalloproteinases: Their role in the pathogenesis of local tissue damage; Biochimie; Jul. 20, 2000.
Gutierrez, Jose Maria et al.; Hemorrhage Caused by Snake Venom Metalloproteinases: A Journey of Discovery and Understanding; Toxins; Mar. 26, 2016.
Ferraz, Camila R. et al.; Multifunctional Toxins in Snake Venoms and Therapeutic Implications: From Pain to Hemorrhage and Necrosis; Frontiers in Ecology and Evolution; vol. 7, article 218; Jun. 2019.
Howes, J.-M. et al.; Neutralization of the hemorrhagic activities of viperine snake venoms and venom metalloproteinases using synthetic peptide inhibitors and chelators; Toxicon; Nov. 30, 2006.

(Continued)

*Primary Examiner* — Amanda L. Aguirre
*Assistant Examiner* — Chris E Simmons
(74) *Attorney, Agent, or Firm* — Faegre Drinker Biddle & Reath LLP

(57) ABSTRACT

The disclosure herein are materials and methods for the treatment of snake bite. Aspects of the disclosure includes pharmaceutical compositions, and kits, both of which may be of use in the treatment of snake bite.

25 Claims, 19 Drawing Sheets

(56) References Cited

OTHER PUBLICATIONS

Figure 1:
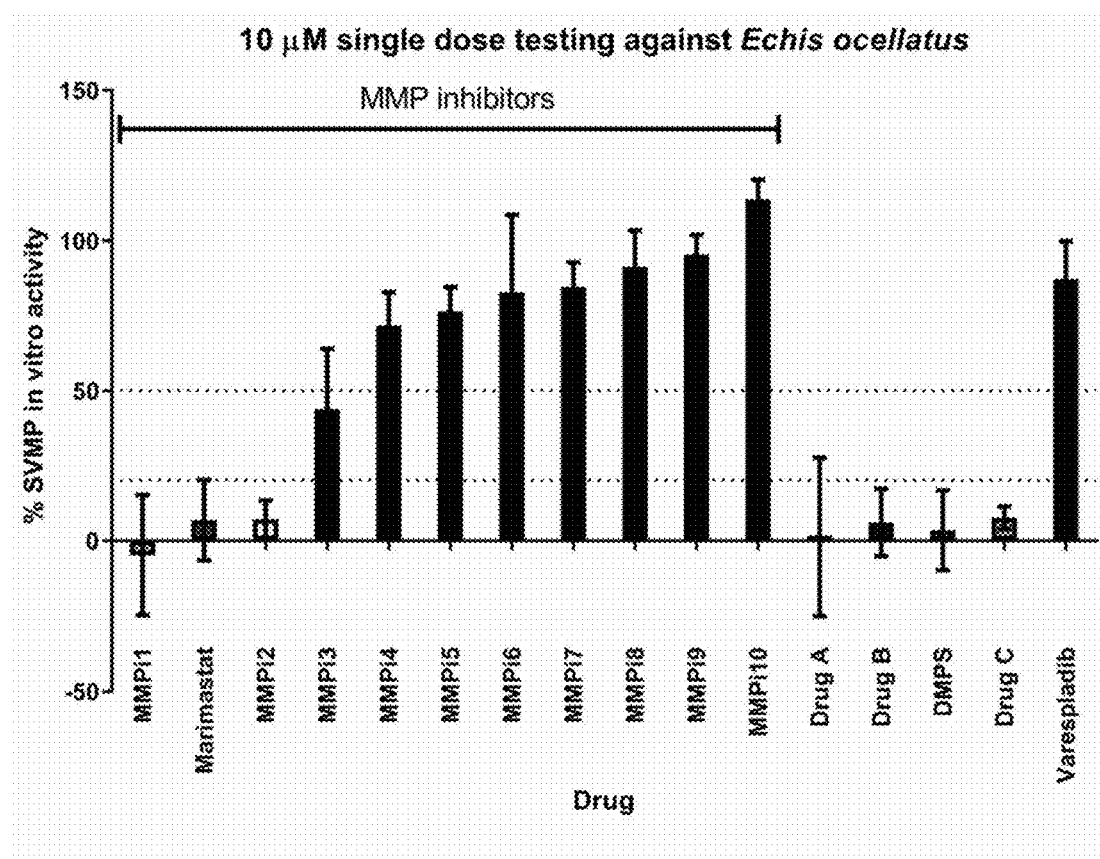

Lewin, Matthew et al.; Varespladib (LY315920) Appears to be a Potent, Broad-Spectrum, Inhibitor of Snake Venom Phospholipase A2 and a Possible Pre-Referral Treatment for Envenomation; Toxins; Aug. 25, 2016.

Arias, Ana Silvia et al.; Peptidomimetic hydroxamate metalloproteinase inhibitors abrogate local and systemic toxicity induced by *Echis ocellatus* (saw-scaled) snake venom; Toxicon; Apr. 8, 2017.

Rucavado, Alexandra et al.; Inhibition of Local Hemorrhage and Dermonecrosis Induced by Bothrops Asper Snake Venom: Effectiveness of Early In Situ Administration of the Peptidomimetic Metalloproteinase Inhibitor Batimastat and the Chelating Agent CaNa2EDTA; The American Society of Tropical Medicine and Hygiene; 2000.

Ainsworth, Stuart et al.; The paraspecific neutralisation of snake venom induced coagulopathy by antivenoms; Communications Biology; 2018.

Lewin, Matthew R. et al.; Delayed LY333013 (Oral) and LY315920 (Intravenous) Reverse Severe Neurotoxicity and Rescue Juvenile Pigs from Lethal Doses of *Micrurus fulvius* (Eastern Coral Snake) Venom; Toxins; Nov. 17, 2018.

Lewin, Matthew R. et al.; Delayed Oral LY333013 Rescues Mice from Highly Neurotoxic, Lethal Doses of Papuan Taipan (*Oxyuranus scutellatus*) Venom; Toxins; Sep. 20, 2018.

Albulescu, Laura-Oana et al.; Preclinical validation of a repurposed metal chelator as an early-intervention therapeutic for hemotoxic snakebite; Science Translational Medicine; May 6, 2020.

Wang, Yiding et al.; Exploration of the Inhibitory Potential of Varespladib for Snakebite Envenomation; Molecules; Feb. 12, 2018.

Layfield, Harry J. et al.; Repurposing Cancer Drugs Batimastat and Marimastat to Inhibit the Activity of a Group I Metalloprotease from the Venom of the Western Diamondback Rattlesnake, *Crotalus atrox*; Toxins; May 9, 2020.

Rowsell, Sian et al.; Crystal Structure of Human MMP9 in Complex with a Reverse Hydroxamate Inhibitor; JMB; 2002.

Still, Kristina B.M. et al.; Multipurpose HTS Coagulation Analysis: Assay Development and Assessment of Coagulopathic Snake Venoms; Toxins; Nov. 25, 2017.

Rogalski, Aymeric et al.; Differential procoagulant effects of saw-scaled viper (*Serpentes: viperidae: echis*) snake venoms on human plasma and the narrow taxonomic ranges of antivenom efficacies; Toxicology Letters; Aug. 25, 2017.

Slagboom, Julien et al.; High throughput screening and identification of coagulopathic snake venom proteins and peptides using nanofractionation and proteomics approaches; PLOS Neglected Tropical Diseases; Apr. 1, 2020.

Winer, Arthur et al. Matrix Metalloproteinase Inhibitors in Cancer Therapy: Turning Past Failures into Future Successes; New York University School of Medicine; Jun. 2018.

Kim, Hyo Shik et al.; Cardiac arrest caused by nafamostat mesilate; Kidney Research and Clinical Practice; Nov. 12, 2015.

Theakston R.D.G et al.; Development of simple standard assay procedures for the characterization of snake venoms; Bulletin of the World Health Organization; 1983.

Harrison, Robert A. et al.; Preclinical antivenom-efficacy testing reveals potentially disturbing deficiencies of snakebite treatment capability in East Africa; PLOS Neglected Tropical Diseases; Oct. 18, 2017.

Annex 5 Guidelines for the production, control and regulation of snake antivenom immunoglobulins, Replacement of Annex 2 of WHO Technical Report Series, No. 964; WHO Expert Committee on Biological Standardization; 2017.

Bolanos, Roger; Toxicity of Costa Rican Snake Venoms for the White Mouse; The American Journal of Tropical Medicine and Hygiene; vol. 21, No. 3; 1972.

Villalta, Mauren et al.; Development of a new polyspecific antivenom for snakebite envenoming in Sri Lanka: Analysis of its preclinical efficacy as compared to a currently available antivenom; Toxicon; Oct. 6, 2016.

Mora-Obando, Diana et al.; Proteomic and functional profiling of the venom of Bothrops ayerbei from Cauca, Colombia, reveals striking interspecific variation with Bothrops asper venom; ScienceDirect; Nov. 11, 2013.

Harrison, Robert A. et al.; Priority Actions and Progress to Substantially and Sustainably Reduce the Mortality, Morbidity and Socioeconomic Burden of Tropical Snakebite; Toxins; Nov. 24, 2016.

De La Rosa, Guillermo et al.; Horse immunization with short-chain consensus a-neurotoxin generates antibodies against broad spectrum of elapid venomous species; Nature Communications; 2019.

Kini, R. Manjunatha et al.; Biosynthetic Oligoclonal Antivenom (BOA) for Snakebite and Next-Generation Treatments for Snakebite Victims; Toxins; Dec. 13, 2018.

Laustsen, Andreas H. et al.; In vivo neutralization of dendrotoxin-mediated neurotoxicity of black mamba venom by oligoclonal human IgG antibodies; Nature Communications; 2018.

Peterson, J. Thomas; The importance of estimating the therapeutic index in the development of matrix metalloproteinase inhibitors; European Society of Cardiology; 2005.

Millar, Andrew W. et al.; Results of single and repeat dose studies of the oral matrix metalloproteinase inhibitor marimastat in healthy male volunteers; Blackwell Science Ltd; 1998.

Rosemurgy, Alexander M.D. et al.; Marimastat in Patients With Advanced Pancreatic Cancer: A Dose-Finding Study; American Journal of Clinical Oncology; vol. 22(3); Jun. 1999.

Nair, Anroop B. et al.; A simple practice guide for dose conversion between animals and human; Journal of Basic and Clinical Pharmacy; 2016.

Varespladib; Adis R&D Profile; 2011.

Rosenson, Robert S. et al.; Effects of Varespladib Methyl on Biomarkers and Major Cardiovascular Events in Acute Coronary Syndrome Patients; Journal of the American College of Cardiology; vol. 56, No. 14; 2010.

Abraham, Edward MD et al.; Efficacy and safety of LY315920Na/S-5920, a selective inhibitor of 14-kDa group IIA secretory phospholipase A2, in patients with suspected sepsis and organ failure; Crit Care Med; vol. 31, No. 3; 2003.

Nicholls, Stephen J. et al.; Varespladib and Cardiovascular Events in Patients With an Acute Coronary Syndrome the VISTA-16 Randomized Clinical Trial; American Medical Association; JAMA; vol. 311, No. 3; Jan. 15, 2014.

Gutierrez, Jose Maria et al.; Varespladib (LY315920) and Methyl Varespladib(LY333013) Abrogate or Delay Lethality Induced by Presynaptically Acting Neurotoxic Snake Venoms; Toxins; Feb. 20, 2020.

Maiorino, Richard M. et al.; Determination and Metabolism of Dithiol Chelating Agents. XVII. In Humans, Sodium 2, 3-Dimercapto-1-Propanesulfonate is Bound to Plasma Albumin Via Mixed Disulfide Formation and is Found in the Urine as Cyclic Polymeric Disulfides; The Journal of Pharmacology and Experimental Therapeutics; vol. 277, No. 1; 1996.

Kosnett, Michael J.; The Role of Chelation in the Treatment of Arsenic and Mercury Poisoning; American College of Medical Toxicology; Nov. 1, 2013.

Wagstaff, Simon C. et al.; Combined snake venomics and venom gland transcriptomic analysis of the ocellated carpet viper, *Echis ocellatus*; ScienceDirect; 2008.

Tan, Nget Hong et al.; Functional venomics of the Sri Lankan Russell's viper (*Daboia russelii*) and its toxinological correlations; Journal of Proteomics; Sep. 3, 2015.

Pla, Davinia et al.; Phylovenomics of Daboia russelii across the Indian subcontinent. Bioactivities and comparative in vivo neutralization and in vitro third-generation antivenomics of antivenoms against venoms from India, Bangladesh and Sri Lanka; Journal of Proteomics; Jul. 17, 2019.

Bradley, John D. et al.; A Randomized, Double-Blinded, Placebo-Controlled Clinical Trial of LY333013, a Selective Inhibitor of Group II Secretory Phospholipase A2, in the Treatment of Rheumatoid Arthritis; The Journal of Rheumatology; 2005.

Sevenet, Pierre-Olivier et al.; Clot waveform analysis: Where do we stand in 2017?; International Journal of Laboratory Hematology; 2017.

(56) References Cited

OTHER PUBLICATIONS

Patra, Aparup et al.; Proteomics and antivenomics of Echis carinatus carinatus venom: Correlation with pharmacological properties and pathophysiology of envenomation; Scientific Reports; Dec. 7, 2017.

Alape-Giron, Alberto et al.; Studies on the venom proteome of Bothrops asper: Perspectives and applications; Toxicon; Jun. 17, 2009.

Calvete, Juan J. et al.; Snake Venomics of Bitis Species Reveals Large Intragenus Venom Toxin Composition Variation: Application to Taxonomy of Congeneric Taxa; Journal of Proteome Research; Jun. 9, 2007.

\* cited by examiner

METHODS AND COMPOSITIONS FOR THE TREATMENT OF SNAKE BITE

CROSS REFERENCE TO RELATED APPLICATION

This application claims priority to U.S. Provisional Application No. 63/188,586, filed on May 14, 2021, the entire disclosure of which is expressly incorporated herein by reference in its entirety.

FIELD OF THE INVENTION

The present invention relates to methods for the treatment of snake bite. Also disclosed are pharmaceutical compositions, and kits, both of which may be of use in the treatment of snake bite.

INTRODUCTION

Snake venoms are complex mixtures of numerous proteins and peptides and extensive interspecific variation in venom composition poses major challenges for the development of generic (i.e., pancontinental) snakebite treatments. Current therapies, known as antivenoms, consist of polyclonal immunoglobulins purified from the plasma/serum of large animals (e.g., equines, ovines) hyperimmunized with snake venoms. Because of the specificity of the resulting immunoglobulins towards the toxins present in the venoms used in manufacture, antivenoms typically have limited efficacy against envenoming by different snake species. In addition, their high cost, poor dose efficacy, adverse reactions and requirement for cold chain make them suboptimal treatments. Antivenoms need to be administered in a clinical setting and many rural snakebite victims suffer major delays in accessing healthcare facilities following a bite. This results in estimates suggesting that 75% of snakebite deaths occur outside of a hospital setting. Therefore, the development of cross-generically efficacious, stable and affordable, prehospital treatments is urgently needed as an effective means to considerably decrease snakebite mortality and morbidity.

Vipers represent a major group of medically important snakes that are widely distributed across the globe, ranging from the Americas to Africa and Asia, and are responsible for causing the majority of snake envenomings in these regions. Treatments for systemic viper envenoming need to neutralize a number of major classes of hemotoxins, which are found in varying abundances across medically important snake species, and typically include the $Zn^{2+}$-dependent snake venom metalloproteinases (SVMPs) and phospholipase $A_2$ ($PLA_2$s), amongst others. Collectively, these three enzymatic families typically comprise >50% of all toxins found in viper venoms.

Small molecule toxin inhibitors have received limited attention as potential alternatives to immunoglobulin-based snakebite therapies, although recent findings have suggested that a number of Phase-2 approved drugs may hold therapeutic promise. Here, we demonstrate that novel combinations of rationally selected small molecule toxin inhibitors offer enhanced efficacy as 'broad spectrum' snakebite therapeutics. We rationally selected two snake venom metalloproteinase inhibitors in vitro and independently combined these drugs with a previously identified phospholipase inhibitor to generate two therapeutic small molecule mixtures capable of neutralizing distinct pathogenic toxins found in the venoms of geographically diverse, medically important, hemotoxic vipers. Preclinical efficacy data demonstrate that the described therapeutic combinations of small molecule toxin inhibitors offer enhanced efficacy over single drugs and thus are promising therapeutic agents, as well as constituting drug leads for the future development of generic therapies for treating viper snakebites.

FIGURE LEGENDS

FIG. 1. Inhibition of *Echis ocellatus* venom metalloproteinase activity by known matrix metalloproteinase inhibitors (MMPi) and rationally selected drugs based on their target site interactions. One microgram of whole venom per reaction was incubated with 10 µM of drug (dissolved in DMSO). Predicted metalloproteinase inhibitors were based on descriptors from a MedChemExpress commercial library and the literature. The background reading was taken as DMSO sample (100% activity) and maximum inhibition (0% activity based on an independent 10 µM marimastat control), this allowed for normalisation of the results within this range across multiple screening plates. The percentage metalloproteinase activity was calculated from an endpoint read taken 45 minutes after substrate addition. The phospholipase inhibitor varespladib was included as a non-metalloproteinase inhibiting drug control. Seven drugs demonstrated potent inhibition of venom metalloproteinase activity as defined by the 20% venom activity dashed line.

Figure 2:
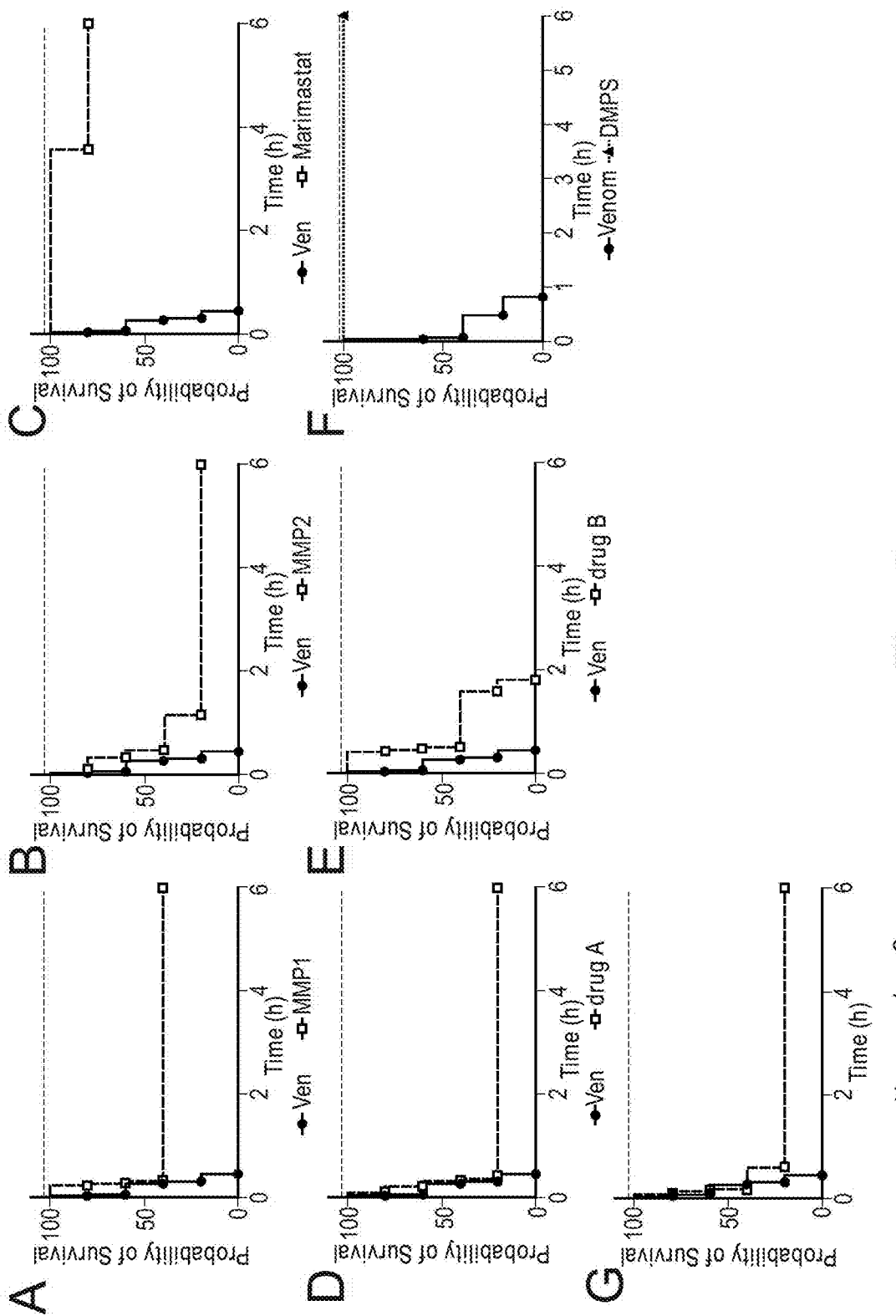

FIG. 2. The MMPi marimastat and the metal chelator DMPS provide murine in vivo preclinical efficacy against systemic envenoming and the lethal effects of venom from the viper *Echis ocellatus*. Kaplan-Meier survival graphs for experimental animals (n=5) receiving *Echis ocellatus* venom (45 µg; 2.5×$LD_{50}$ dose) or venom preincubated (30 min at 37° C.) with various drugs via the intravenous route and monitoring for 6 h (A, MMPi1; B, MMPi2; C, marimastat; D, drug A; E, drug B; F, DMPS; G, drug C). Drug-only controls are presented as black dashed lines at the top of each graph (none of the drugs exhibited any observable toxicity at the given doses). Of the in vitro selected drugs tested, only DMPS and marimastat provided ≥50% survival.

Figure 3:
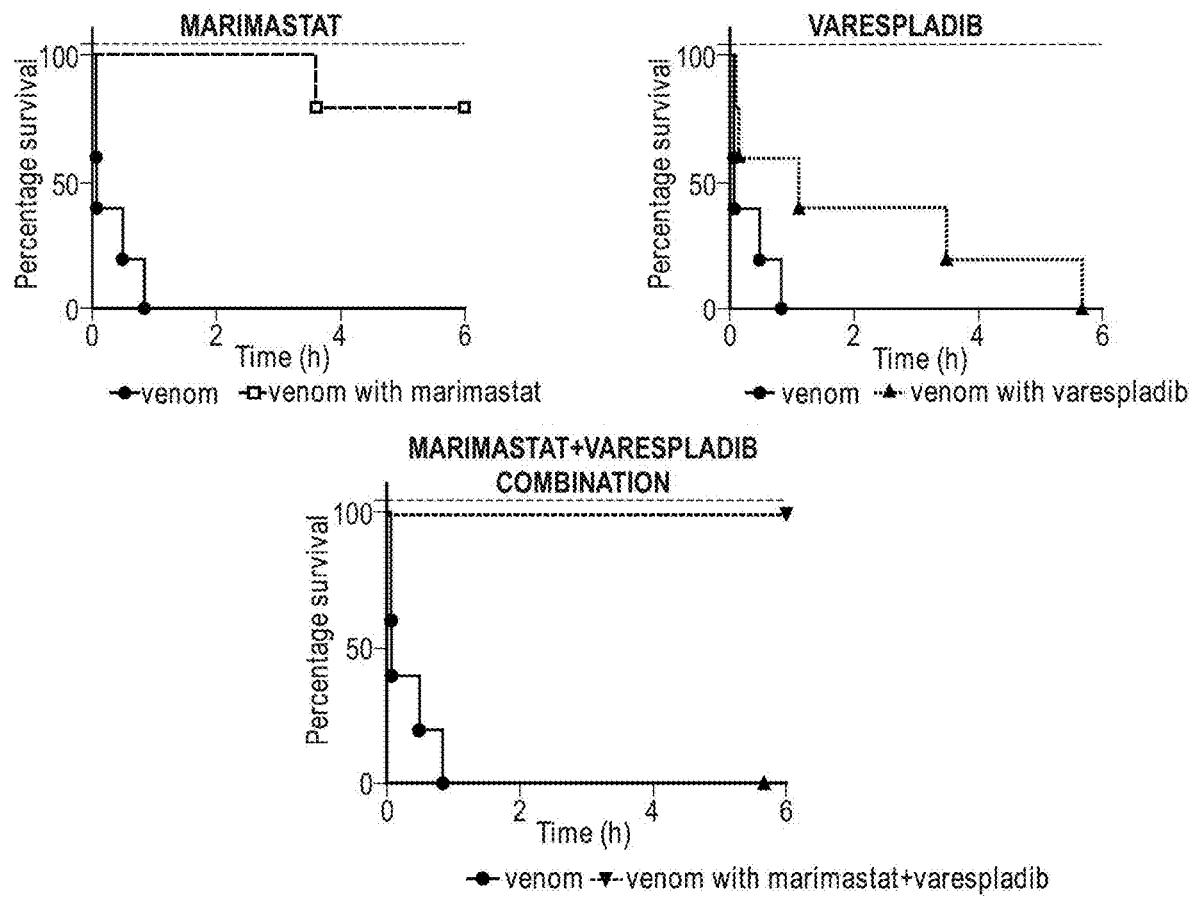

FIG. 3. Preclinical efficacy of solo and combined drugs targeting distinct venom toxin families demonstrates that the drug combination of marimastat and varespladib provides enhanced efficacy over each drug alone. Kaplan-Meier survival graphs for experimental animals (n=5) receiving *Echis ocellatus* venom (45 µg; 2.5×$LD_{50}$ dose) or venom preincubated (30 min at 37° C.) with marimastat or varespladib or a therapeutic mixture containing both marimastat and varespladib via the intravenous route and monitoring for 6 hours. Drug-only controls are presented as black dashed lines at the top of each graph (none of the drugs exhibited any observable toxicity at the given doses).

Figure 4:
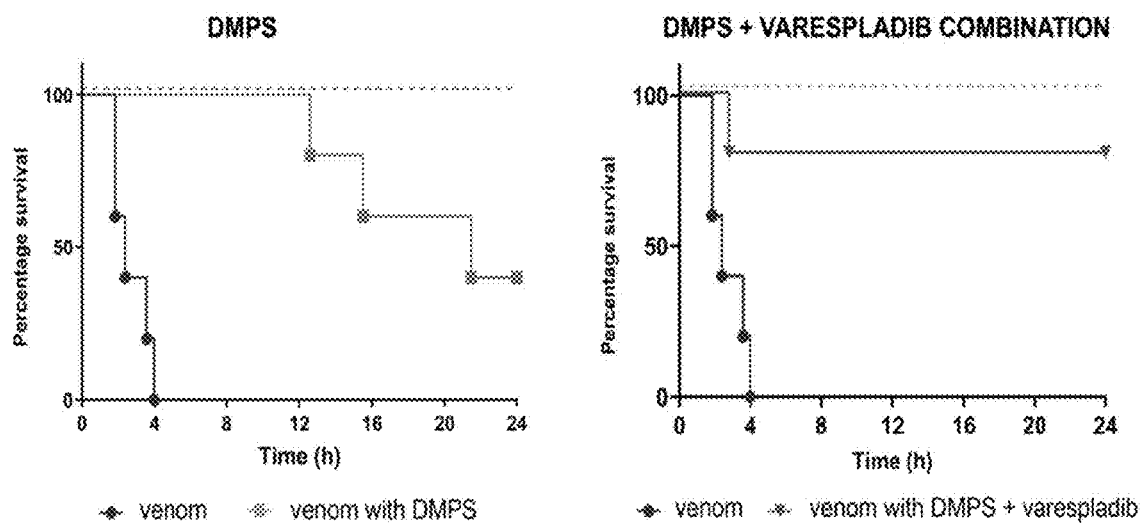

FIG. 4. Preclinical efficacy of solo and combined drugs targeting distinct venom toxin families demonstrates that the drug combination of DMPS and varespladib provides enhanced efficacy over DMPS alone. Kaplan-Meier survival graphs for experimental animals (n=5) receiving *Echis ocellatus* venom via the intraperitoneal route (90 µg; 5×$LD_{50}$ dose) or venom followed 15 minutes later by DMPS or a therapeutic mixture containing DMPS and varespladib, all via the intraperitoneal route and with monitoring for 24 h. Drug-only controls are presented as black dashed lines at the top of each graph (none of the drugs exhibited any observable toxicity at the given doses).

Figure 5:
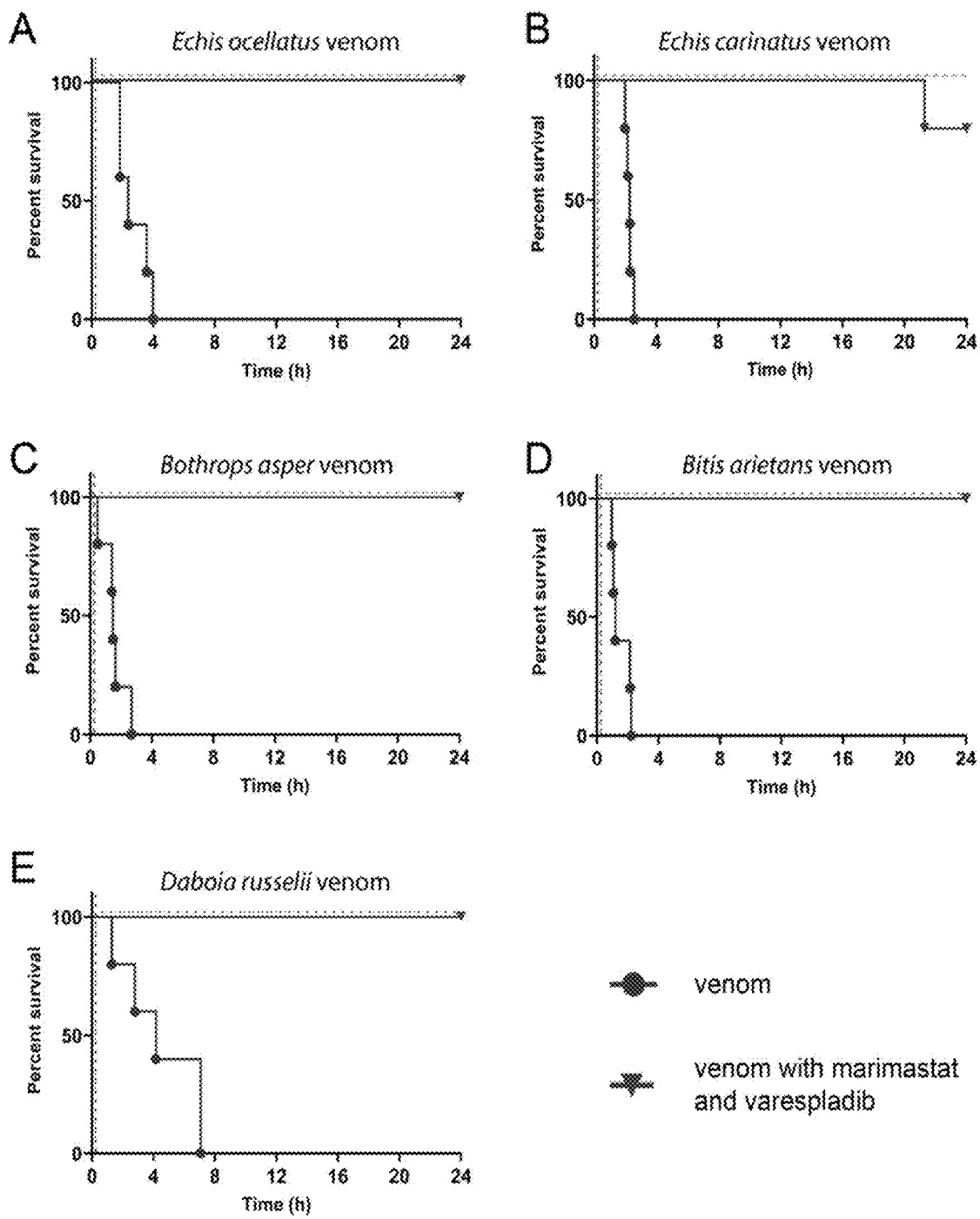

FIG. 5. The therapeutic combination of marimastat and varespladib provides broad preclinical efficacy against the lethal effects of envenomings from various vipers in a murine in vivo challenge and treat model. Kaplan-Meier survival graphs for experimental animals (n=5) receiving venom, followed by delayed drug treatment (15 min later) with a dual drug combination of marimastat and varespladib. Both venom and treatment were delivered via the intraperitoneal route, and the end of the experiment was at 24 h. Survival of mice receiving: A) *E. ocellatus* (90 µg, 5×i.v. LD$_{50}$), B) *E. carinatus* (95 µg, 5×i.v. LD$_{50}$), C) *B. asper* (303 µg, 3×i.p. LD$_{50}$), D) *B. arietans* (108 µg, 5×i.v. LD$_{50}$) and E) *D. russelii* (105 µg, 13×i.v. LD$_{50}$) venom, with and without the inhibitor mix (120 µg of each drug) 15 min later. The drug-only control is presented as a black dashed line at the top of each graph (no toxicity was observed at the given dose).

Figure 6:
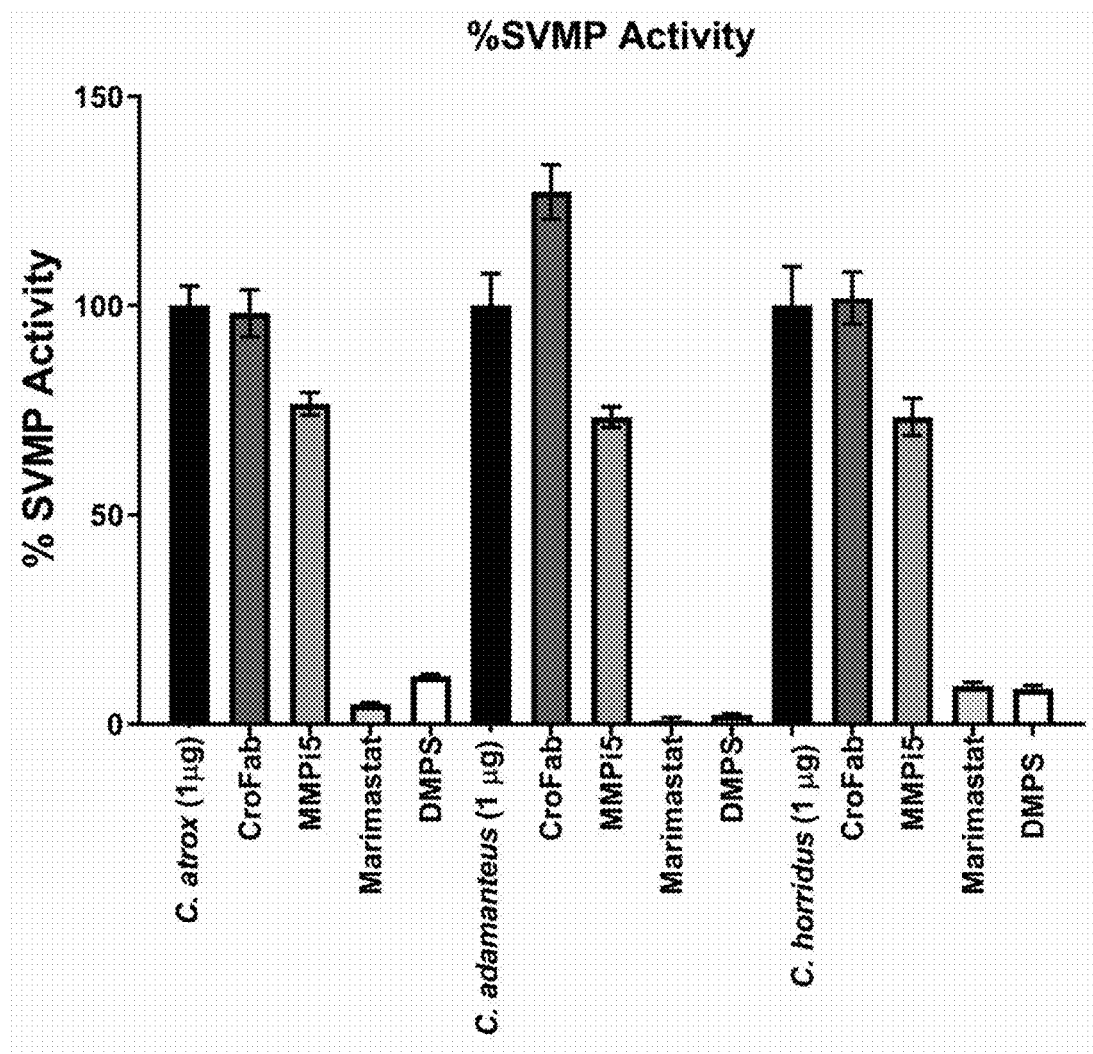

FIG. 6. Marimastat and DMPS potently inhibit the in vitro metalloproteinase activity of North American rattlesnake venoms. One microgram of *C. atrox*, *C. adamanteus* and *C. horridus* venom were incubated with either 25 µM of marimastat, DMPS or "MMPi5" or 25 µg of CroFab antivenom and the percentage metalloproteinase activity calculated from an endpoint read (45 mins) relative to the activity of venom-only samples following the subtraction of background, negative control readings (DMSO only). Error bars represent standard deviation.

Figure 7A:
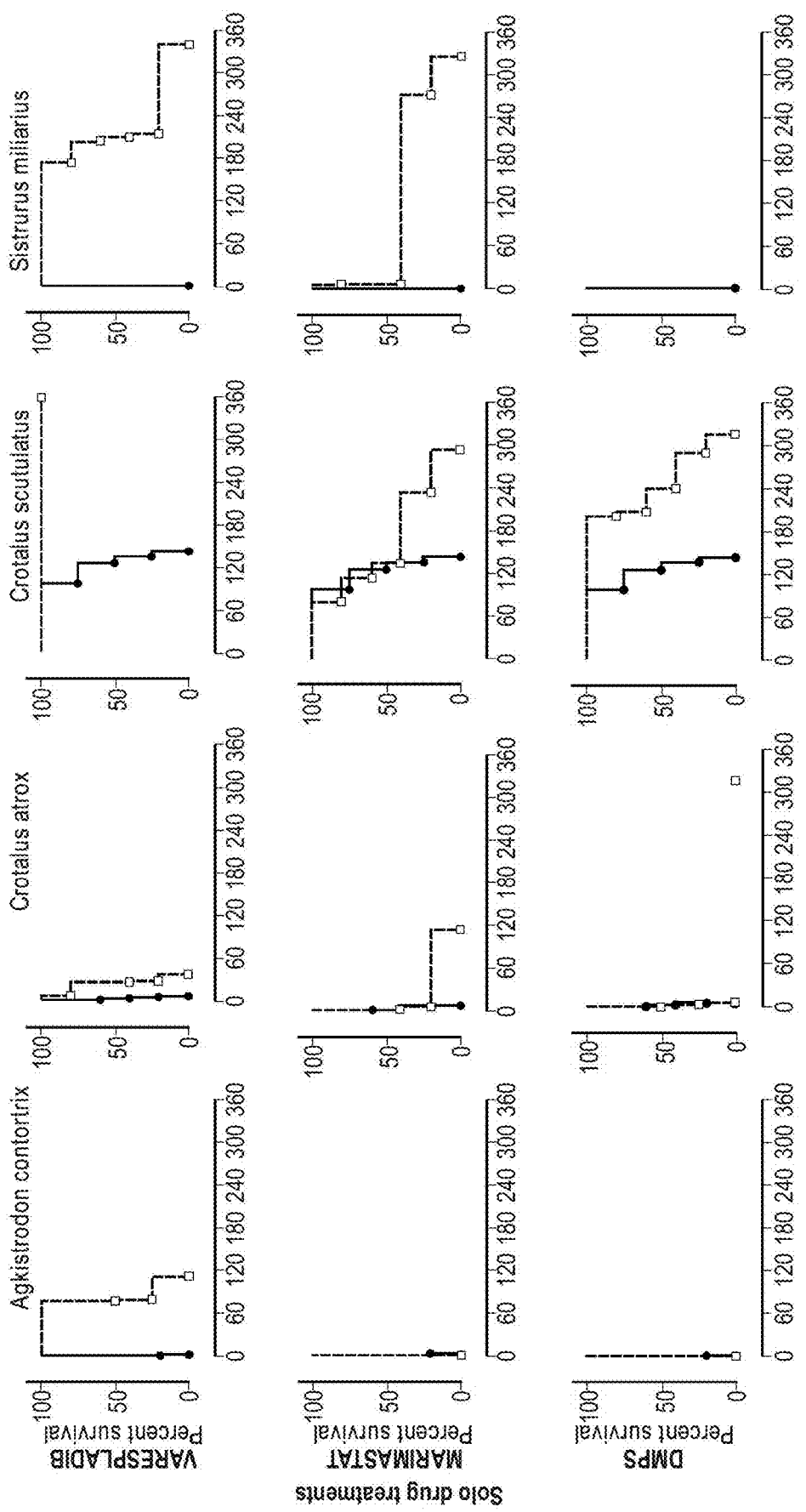

FIG. 7A. The therapeutic combinations of varespladib and marimastat and varespladib and DMPS provide broad preclinical efficacy against the lethal effects of envenomings from various North American pit vipers in a murine in vivo model of lethality. The data shows that drug combinations provide enhanced efficacy over the solo drugs of varespladib, marimastat and DMPS alone. The figure shows Kaplan-Meier survival graphs for experimental animals (n=5) receiving venom (black lines; from either *A. contortrix*, *C. atrox*, *C. scutulatus* or *S. miliarius*, see different columns) or venom preincubated (30 min at 37° C.) with marimastat or varespladib or DMPS or therapeutic mixtures containing both varespladib and marimastat or varespladib and DMPS (grey lines; see different rows) via the intravenous route and monitoring for 6 hours. The panel shows the data from the three solo drugs, varespladib (top), marimastat (middle) and DMPS (bottom).

Figure 7B:
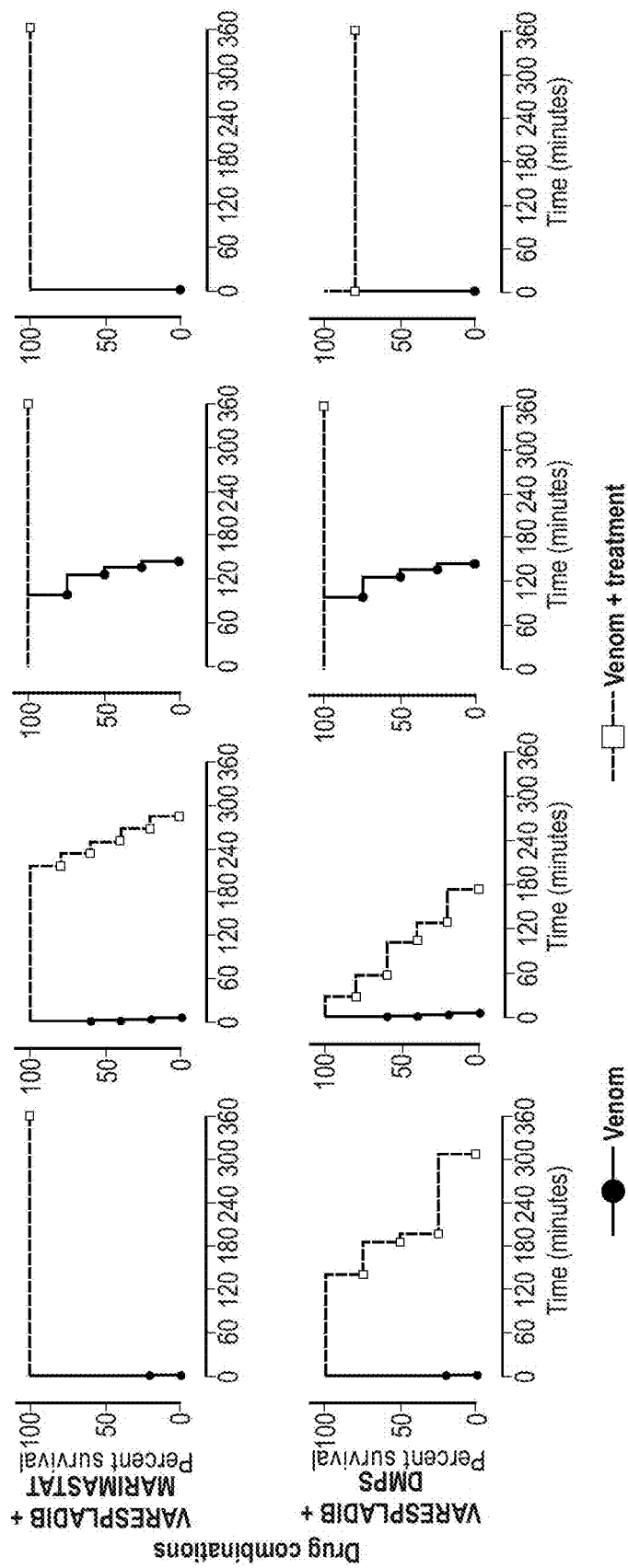

FIG. 7B. The therapeutic combinations of varespladib and marimastat and varespladib and DMPS provide broad preclinical efficacy against the lethal effects of envenomings from various North American pit vipers in a murine in vivo model of lethality. The data shows that drug combinations provide enhanced efficacy over the solo drugs of varespladib, marimastat and DMPS alone. The figure shows Kaplan-Meier survival graphs for experimental animals (n=5) receiving venom (black lines; from either *A. contortrix*, *C. atrox*, *C. scutulatus* or *S. miliarius*, see different columns) or venom preincubated (30 min at 37° C.) with marimastat or varespladib or DMPS or therapeutic mixtures containing both varespladib and marimastat or varespladib and DMPS (grey lines; see different rows) via the intravenous route and monitoring for 6 hours. The panel shows the data from the two drug combinations, varespladib and marimastat (top) and varespladib and DMPS (bottom).

Figure 8:
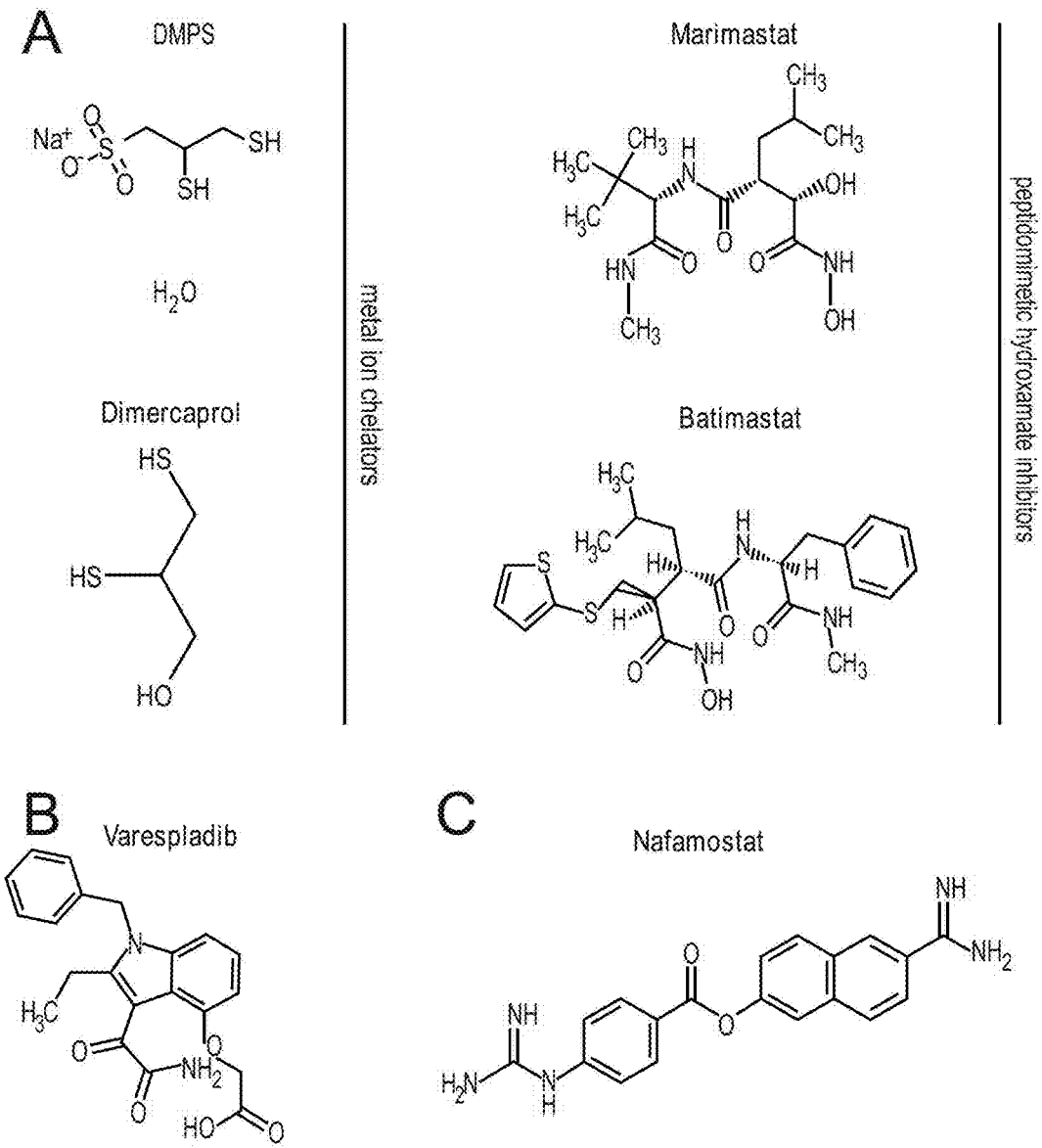

FIG. 8. Chemical structures of the small molecule toxin inhibitors used in this study. (A) Snake venom metalloproteinase (SVMP)-inhibitors: the metal ion chelators, DMPS (unithiol) and dimercaprol, and the peptidomimetic hydroxamate inhibitors, marimastat and batimastat. (B) The secretory phospholipase $A_2$ (PLA$_2$)-inhibitor, varespladib. (C) The serine protease-inhibitor, nafamostat.

Figure 9:
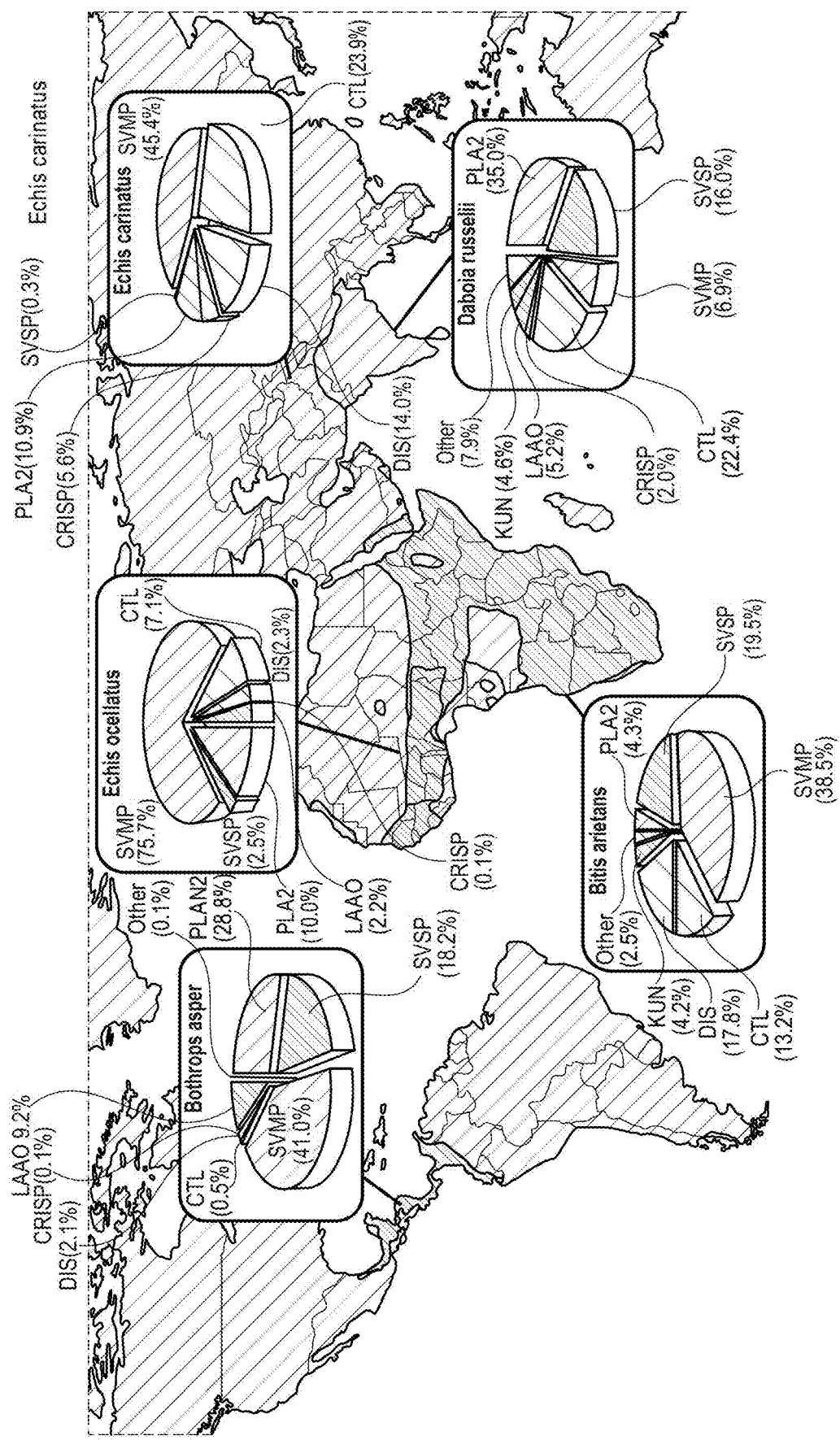

FIG. 9. The geographical distributions and varying proteomic venom compositions of the medically important viper species used in this study. The previously defined venom proteomes of *Echis ocellatus* (Nigeria)[63], *Echis carinatus* (India)[68], *Bothrops asper* (Costa Rica)[69], *Bitis arietans* (Nigeria)[70] and *Daboia russelii* (Sri Lanka)[64] are presented in pie charts. Toxin family key: SVMP, snake venom metalloproteinase; SVSP, snake venom serine protease; PLA$_2$, phospholipase A$_2$; CTL, C-type lectin; LAAO, L-amino acid oxidase; DIS, disintegrin; CRISP, Cysteine-rich secretory protein; KUN, Kunitz-type serine protease inhibitor. Geographical species distributions were drawn using QGIS v3.10 software based on data downloaded from the World Health Organization Venomous Snake Distribution database and the IUCN Red List of Threatened Species database.

Figure 10:
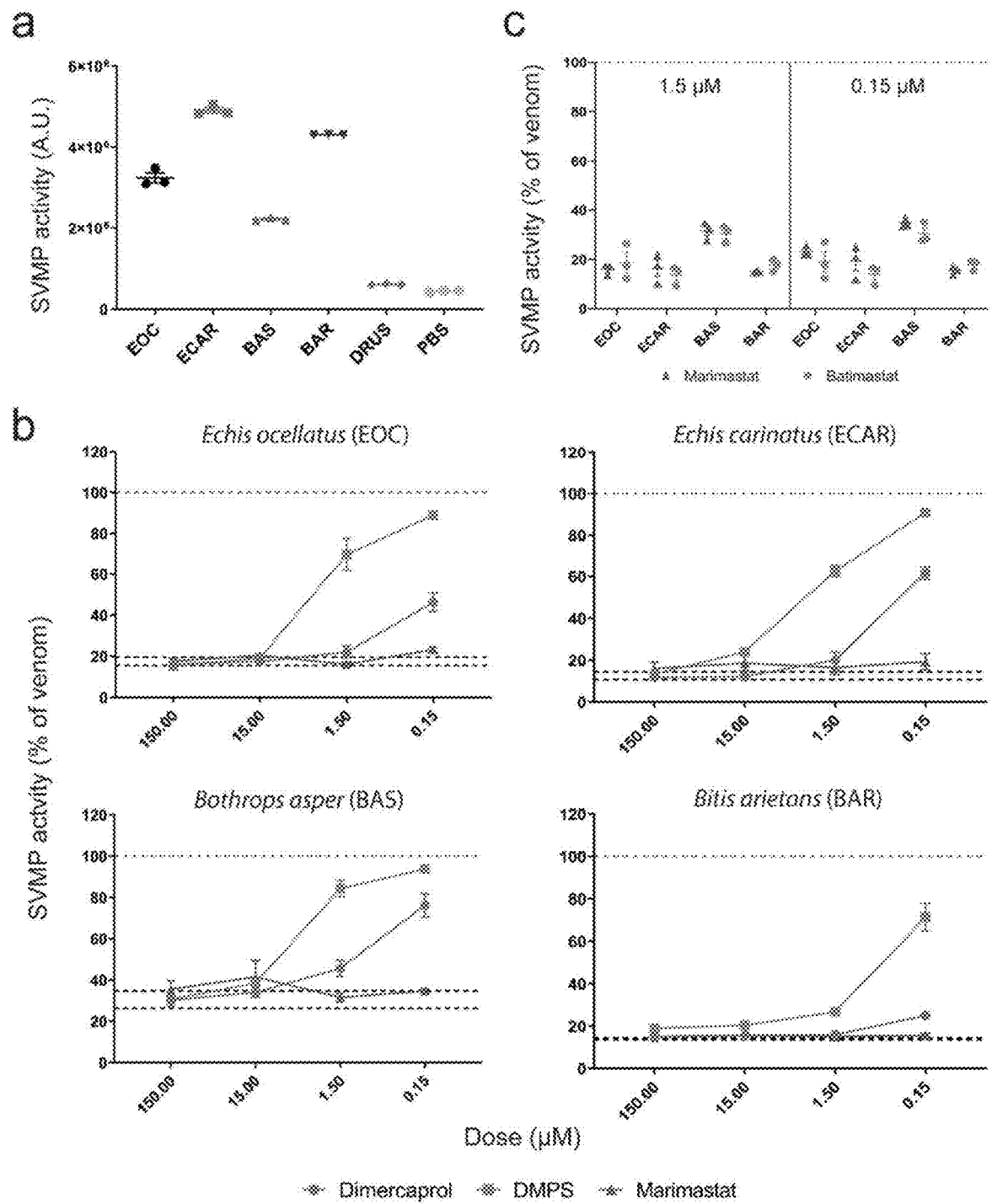

FIG. 10. Small molecule toxin inhibitors inhibit the in vitro SVMP activities of several geographically distinct viper venoms. (A) SVMP activities of the five viper venoms quantified by fluorogenic assay. The data presented represent mean measurements and SEMs of area under the curves of fluorescent arbitrary units taken from three independent experimental runs. EOC, *E. ocellatus*; ECAR, *E. carinatus*; BAS, *Bothrops asper*; BAR, *Bitis arietans*; DRUS, *Daboia russelii*. (B) The effectiveness of metal chelators and peptidomimetic hydroxamate inhibitors at inhibiting the SVMP activity of the various viper venoms. Drug concentrations from 150 µM to 150 nM (highest to lowest dose tested) are presented. The data is expressed as percentage of the venom-only sample (100%, top dashed line). The negative control is presented as an interval (bottom dashed lines) and represents the values recorded in the PBS-only samples (expressed as percentage of venom activity), where the highest and the lowest values in each set of independent experiments are depicted. Inhibitors are color-coded (dimercaprol, red; DMPS, turquoise; marimastat, purple). (C) Comparison of SVMP inhibition by marimastat and batimastat at two concentrations (1.5 µM, left; 0.15 µM, right), expressed as the percentage of the venom-only sample (100%, dashed line). All data represent triplicate independent repeats with SEMs, where each technical repeat represents the mean of n≥2 technical replicates.

Figure 11:
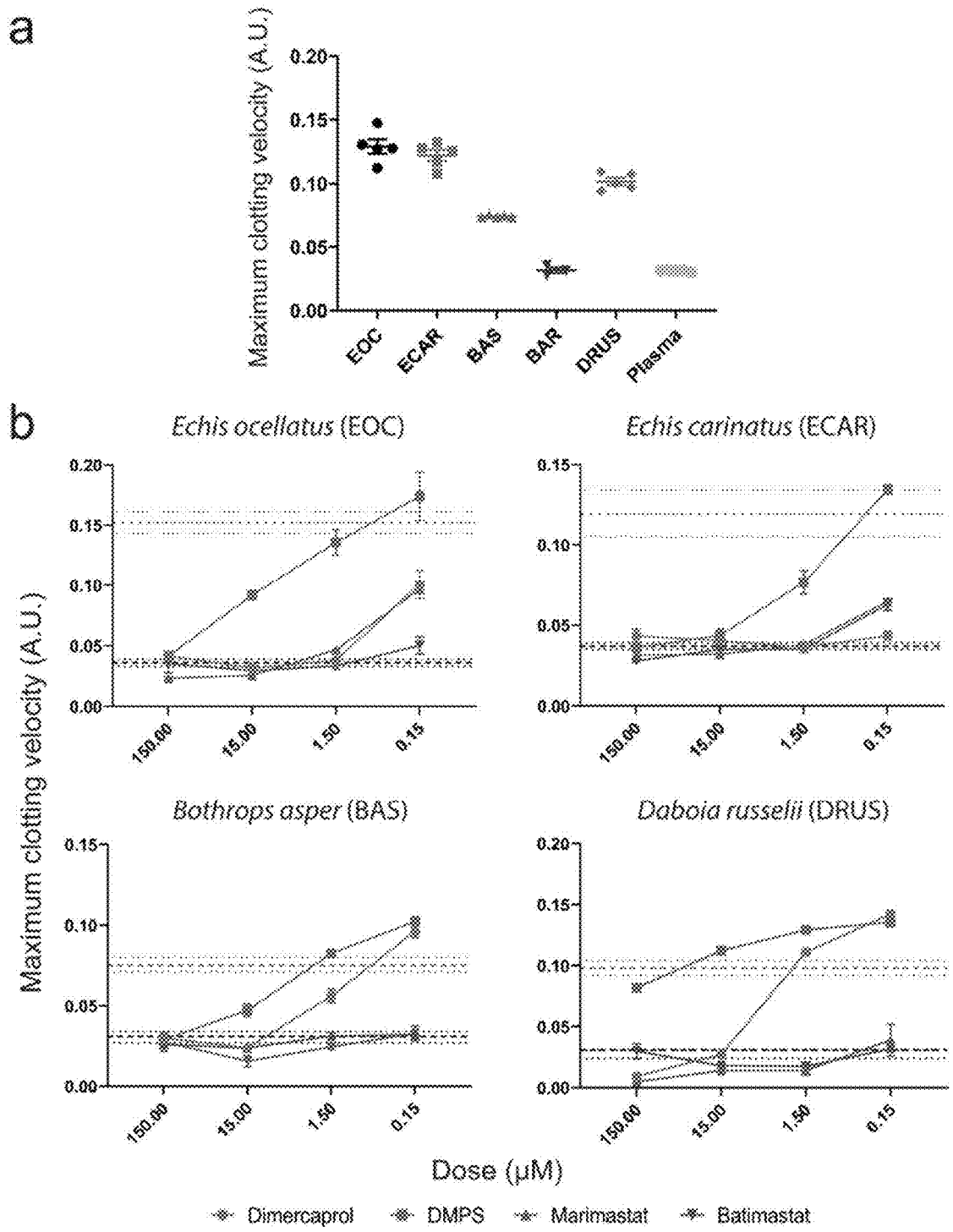

FIG. 11. SVMP-inhibitors neutralize the in vitro procoagulant activities of several geographically distinct viper venoms. (A) The coagulopathic activities of the viper venoms, showing that all, except *B. arietans* (BAR), exhibit procoagulant effects by increasing the clotting velocity in comparison with the normal plasma control. The data presented represents the maximum clotting velocity, calculated as the maximum of the first derivative of each clotting curve, from triplicate independent repeat experiments with SEMs, where each technical repeat represents the mean of n≥2 technical replicates. EOC, *E. ocellatus*; ECAR, *E. carinatus*; BAS, *Bothrops asper*, BAR, *Bitis arietans*; DRUS, *Daboia russelii*. (B) Neutralization of procoagulant venom activity by four SVMP-inhibitors across four drug concentrations (150 µM to 150 nM). The data is expressed as the maximum clotting velocity at each dose. The negative (PBS) and positive (venom-only) controls are presented as intervals (bottom dashed and top dashed lines, respectively), with the latter representing the mean maximum clotting velocity in these samples±SEM. The data represent triplicate independent repeats with SEMs, where each technical repeat represents the mean of n≥2 technical replicates. Note the different y-axis scales.

Figure 12:
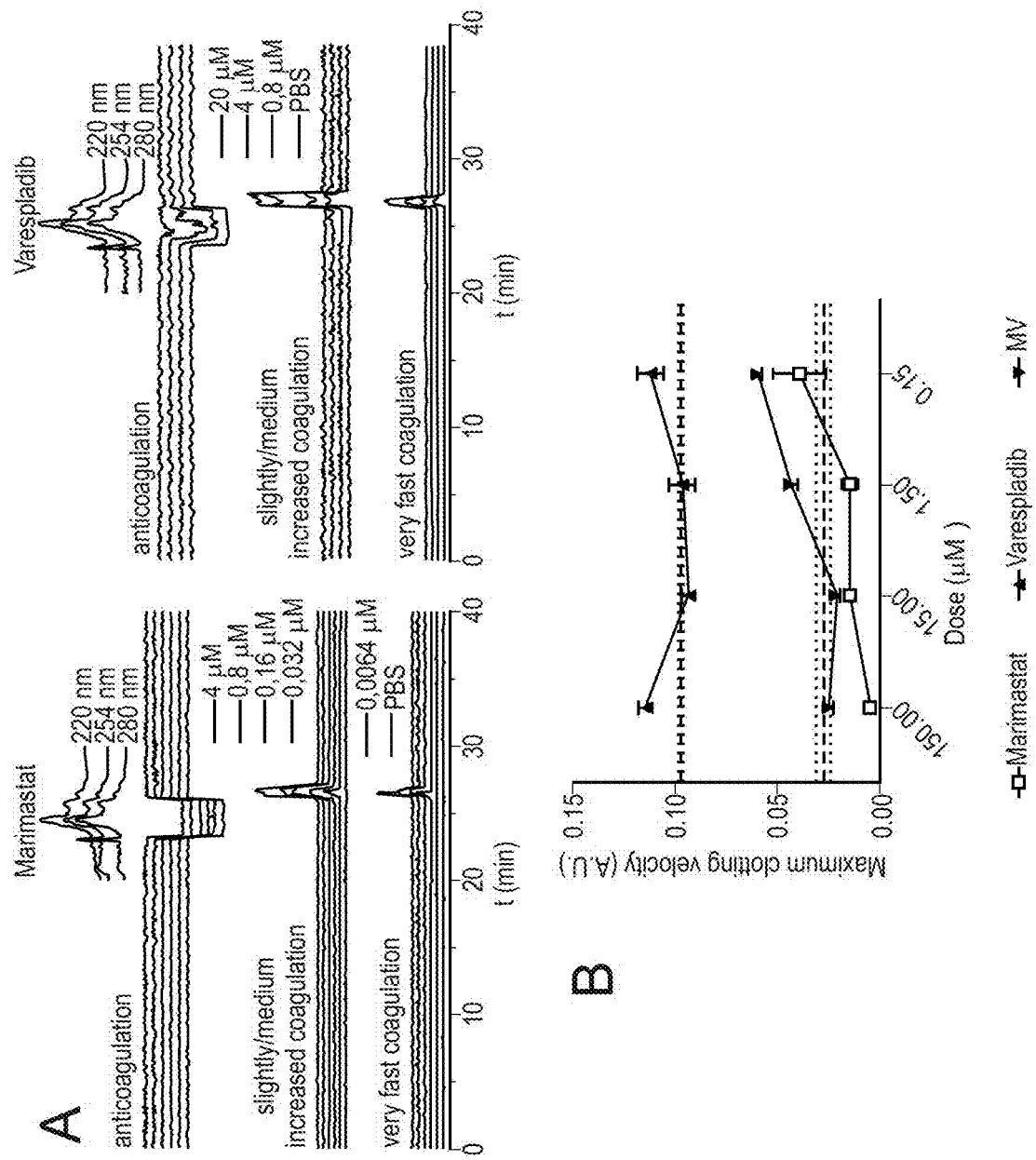

FIG. 12. The inhibitory effects of marimastat and varespladib against procoagulant and anticoagulant toxins fractionated from Russell's viper (*D. russelii*) venom. (A) Representative nanofractionation chromatograms showing the neutralizing potency of marimastat and varespladib against the pro- and anti-coagulant activities of *D. russelli* venom, respectively. The data is plotted separately for 'very fast coagulation', 'medium coagulation' and 'anticoagulation', based on the slopes of the 0-5 min and 0-20 min readings, and the single endpoint reading at 180 min. The tested inhibitor concentrations are presented alongside the chromatograms. (B) The interplay between marimastat and varespladib in neutralizing coagulation-related activities of *D. russelii* venom across a 150 µM-150 nM concentration range. The data is presented as the maximal clotting velocity at each concentration, and represents means of triplicate independent repeats with SEMs, where each technical repeat represents the mean of n≥2 technical replicates. The venom-only control (top dashed lines) and the negative control (bottom dashed lines) are presented as intervals and represent the average±SEM observed for the venom-only and PBS controls across all datasets and replicates.

Figure 13:
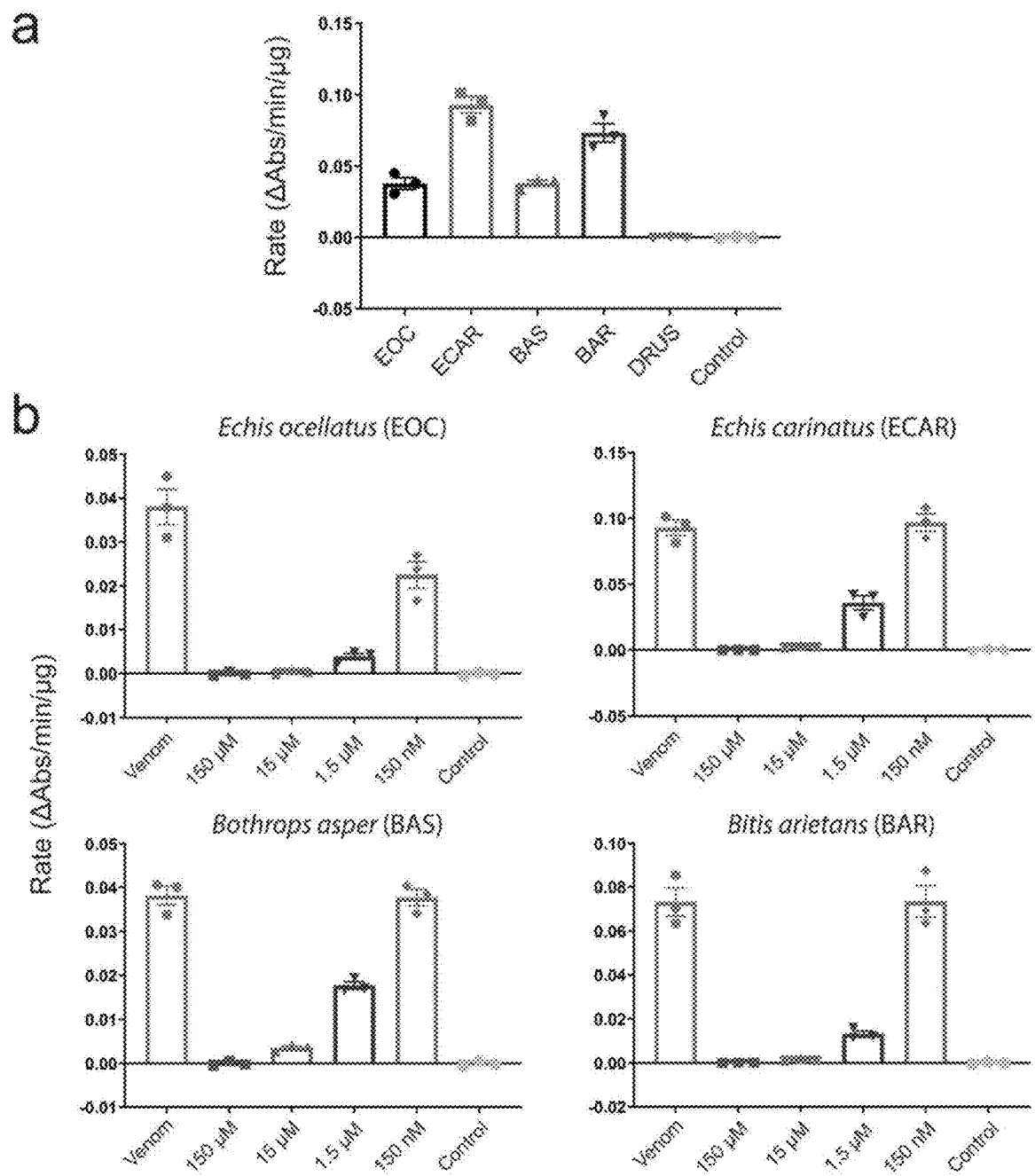

FIG. 13. Nafamostat inhibits the in vitro serine protease activities of several geographically distinct viper venoms. (A) The serine protease (SVSP) activity of five viper venoms expressed as the rate (ΔAbs/time/µg venom) of substrate consumption determined by kinetic chromogenic assay. The data represents triplicate independent repeats with SEMs, where each technical repeat represents the mean of n≥2 technical replicates. EOC, *E. ocellatus*; ECAR, *E. carinatus*; BAS, *Bothrops asper*, BAR, *Bitis arietans*; DRUS, *Daboia russelii*. (B) Neutralization of SVSP venom activity by the serine protease-inhibitor nafamostat. The data is expressed as rates (ΔAbs/time/µg venom) and represents triplicate independent repeats with SEMs, where each technical repeat represents the mean of n≥2 technical replicates. Venom only activity (venom) is displayed alongside venom incubated with decreasing molarities of nafamostat (150 µM to 150 nM). Note the different y-axis scales.

Figure 14:
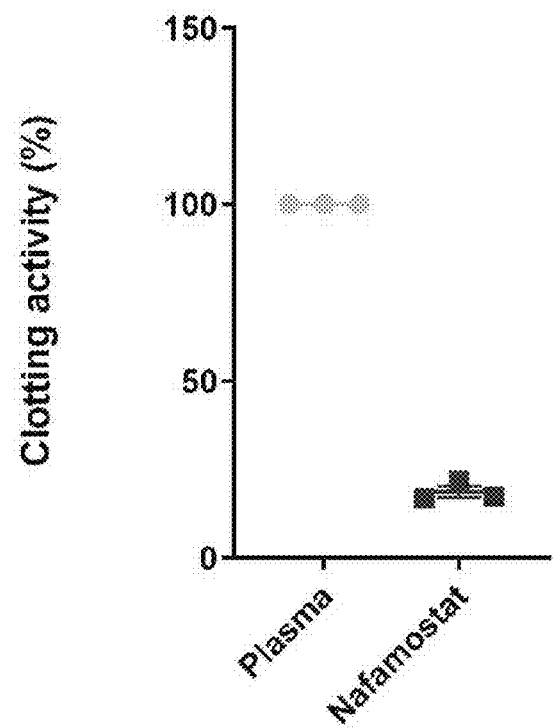

FIG. 14. The serine protease-inhibitor nafamostat inhibits normal plasma clotting. Comparison of normal clotting (i.e. in the absence of venom and inhibitors via recalcification) and clotting in the presence of the generic serine protease-inhibitor nafamostat. At high doses (150 µM), nafamostat dramatically inhibits plasma coagulation. The anticoagulant effect of this drug is expressed as a percentage of the plasma-only activity.

Figure 15:
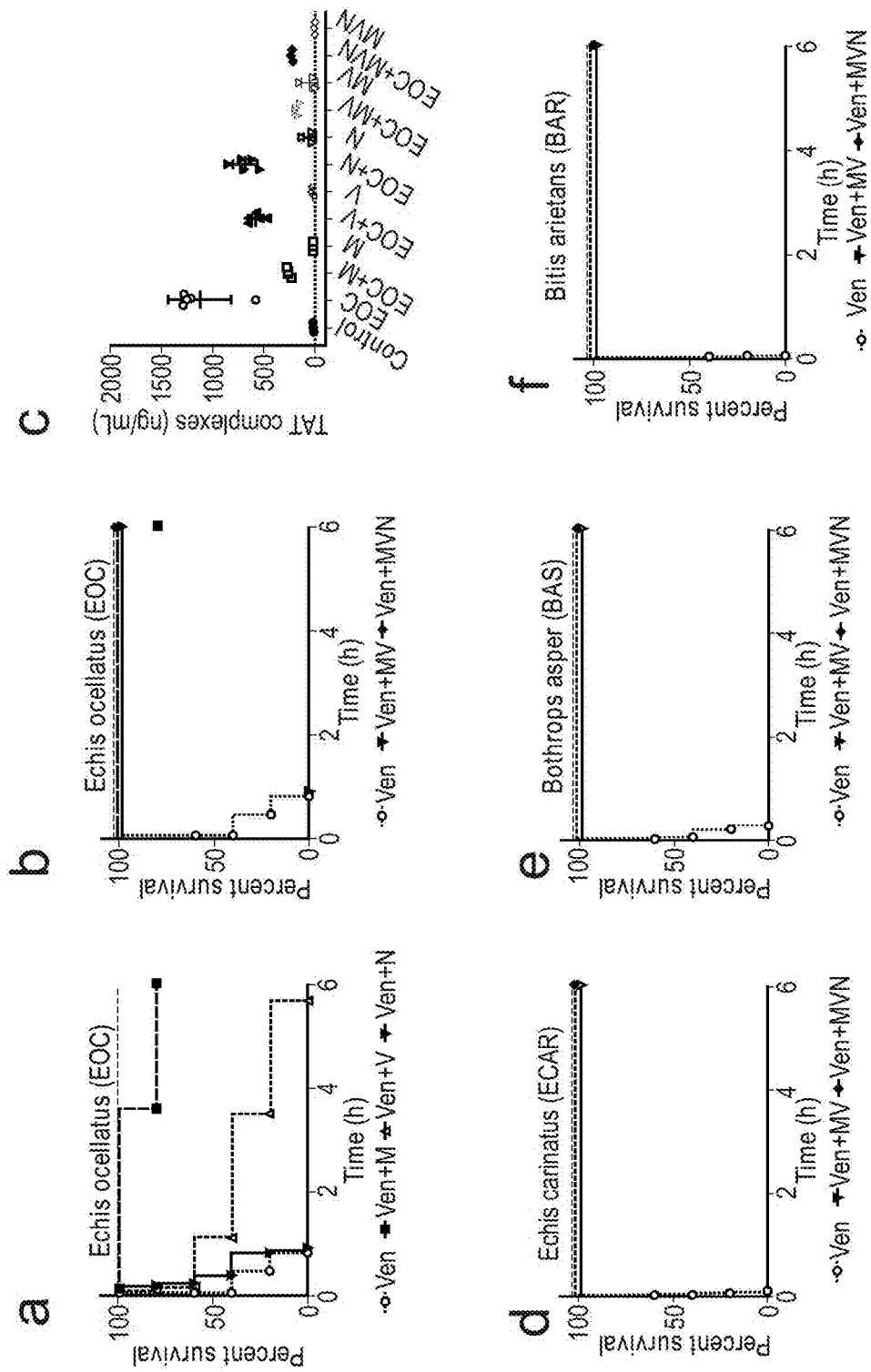
Figure 15:
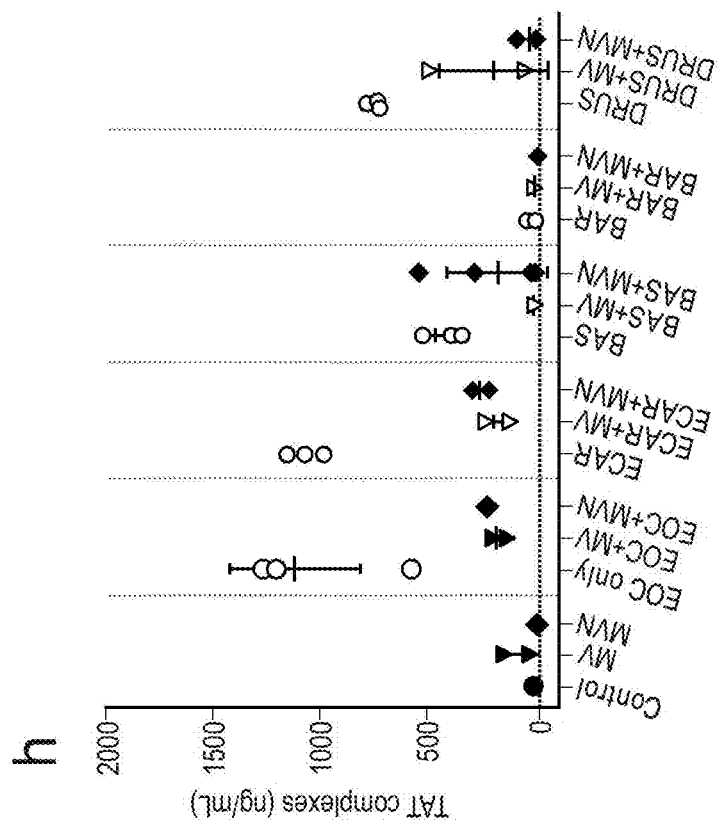
Figure 15:
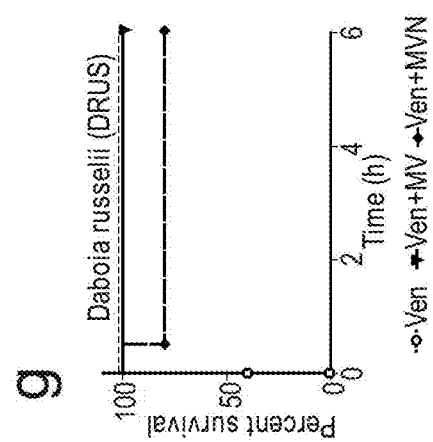

FIG. 15. Combinations of small molecule toxin inhibitors broadly protect against venom lethality in an in vivo 'preincubation' model of snake envenoming. Kaplan-Meier survival graphs for experimental animals (n=5) receiving venom (Ven) preincubated (30 mins at 37° C.) with different small molecule inhibitors or inhibitor mixes via the intravenous route and monitored for 6 h. Drug-only controls are presented as dashed lines at the top of each graph (none of the drugs exhibited any observable toxicity at the given doses). (A) Survival of mice receiving 45 µg of *E. ocellatus* venom (2.5×$LD_{50}$ dose) with and without 60 µg of marimastat or varespladib or nafamostat. (B) Survival of mice receiving 45 µg of *E. ocellatus* venom (2.5×$LD_{50}$ dose) with and without a dual combination mixture of marimastat and varespladib (MV, 60 µg each) or a triple combination mixture of marimastat, varespladib and nafamostat (MVN, 60 µg each). (C) Quantified thrombin-antithrombin (TAT) levels in the envenomed animals from (A) and (B). Where the time of death was the same within experimental groups (e.g. early deaths or complete survival) TAT levels were quantified for n=3, and where times of death varied, n=5. The data displayed represents means of the duplicate technical repeats plus SDs. (D-G) Kaplan-Meier survival graphs for experimental animals (n=5) receiving inhibitor mixes (MV or MVN) preincubated with 2.5×$LD_{50}$ dose of *E. carinatus* (47.5 µg, D), *B. asper* (47 µg, E), *B. arietans* (54 µg, F) or *D. russelii* (20 µg, G) venom. (H) Quantified TAT levels in the envenomed animals from (D-G), with data presented as described for (C).

Figure 16:
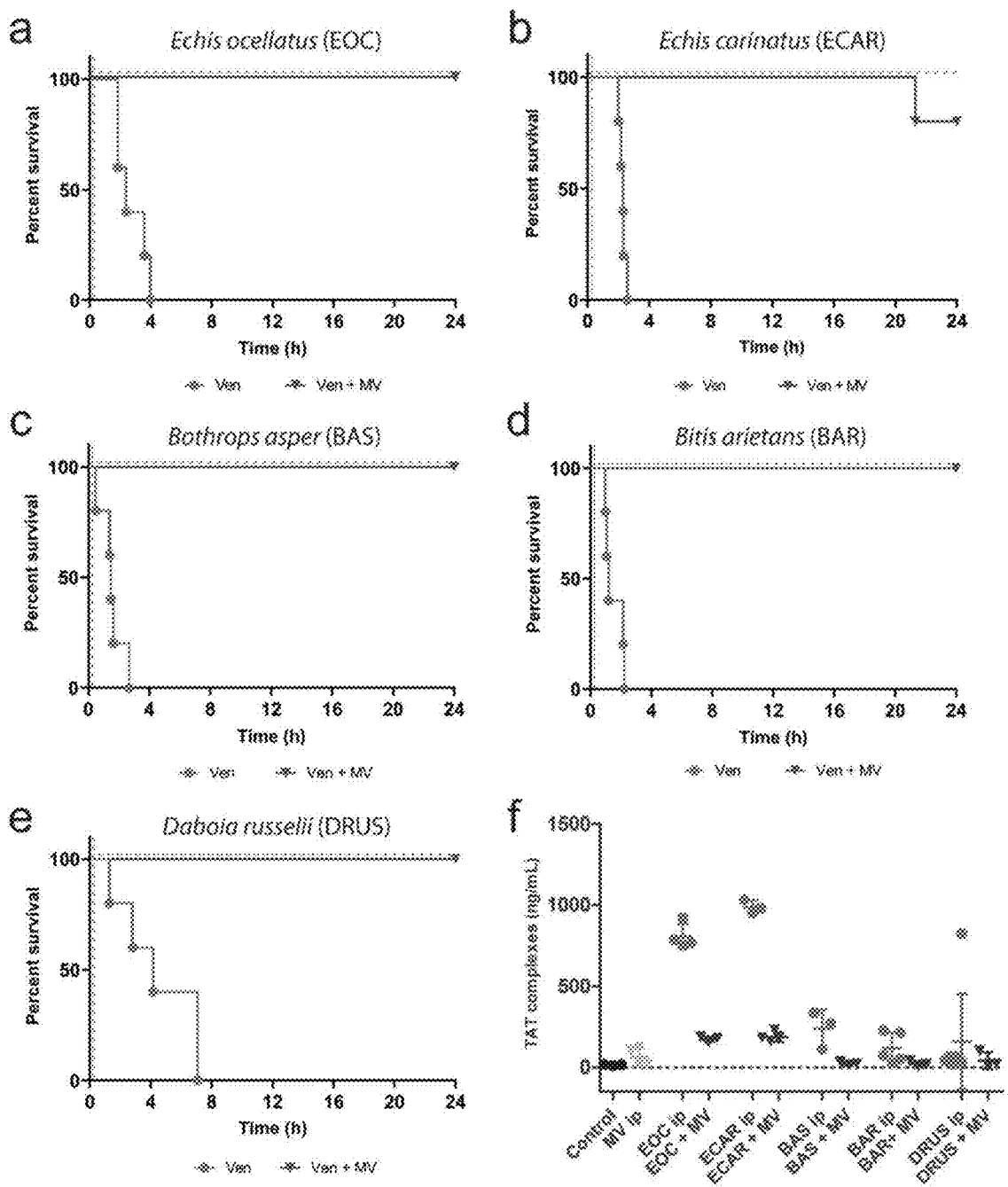

FIG. 16. The inhibitor combination of marimastat and varespladib (MV) provides broad preclinical efficacy against venom lethality in an in vivo 'challenge then treat' model of envenoming. Kaplan-Meier survival graphs for experimental animals (n=5) receiving venom (Ven), followed by delayed drug treatment (15 mins later) with a dual combination of marimastat and varespladib. Both venom and treatment were delivered via the intraperitoneal route, and the end of the experiment was at 24 h. Survival of mice receiving: (A) *E. ocellatus* (90 µg, 5×iv $LD_{50}$), (B) *E. carinatus* (95 µg, 5×iv $LD_{50}$), (C) *B. asper* (303 µg, 3×ip $LD_{50}$), (D) *B. arietans* (108 µg, 5×iv $LD_{50}$) and (E) *D. russelii* (105 µg, 13×iv $LD_{50}$) venom, with and without the inhibitor mix (120 µg of each drug) 15 mins later. The drug-only control is presented as a dashed line at the top of each graph (no toxicity was observed at the given dose). (F) Quantified thrombin-antithrombin (TAT) levels in the envenomed animals from (A-E). Where the time of death was the same within experimental groups (e.g. early deaths or complete survival) TAT levels were quantified for n=3, and where times of death varied, n=5. The data displayed represents means of the duplicate technical repeats plus SDs.

Figure 17:
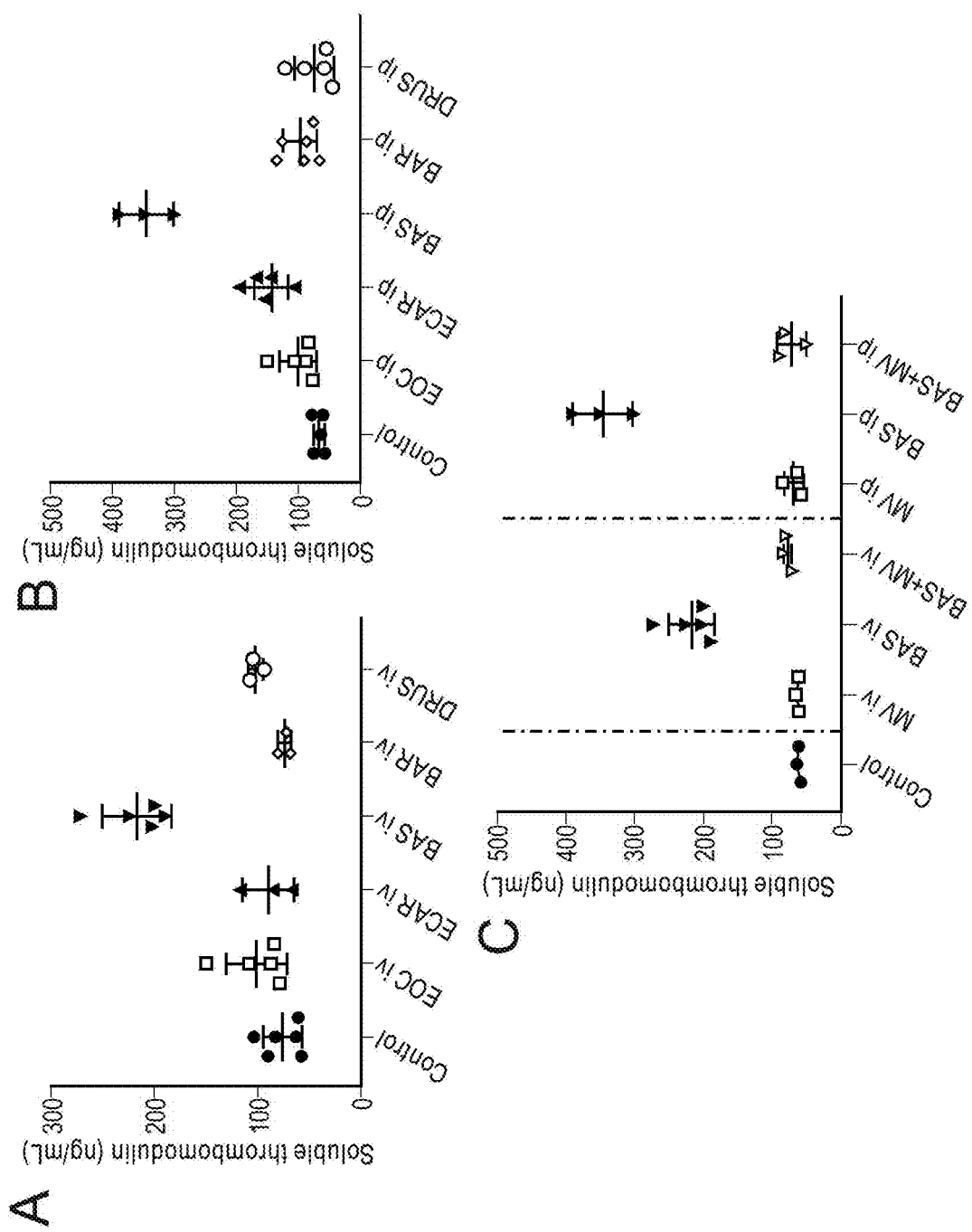

FIG. 17. Soluble thrombomodulin is a valuable biomarker for *Bothrops asper* envenoming. Quantified levels of soluble thrombomodulin determined by ELISA experiments using mouse plasma collected from experimental animals challenged with venoms±inhibitors via the intravenous (iv) and intraperitoneal (ip) routes. Quantified soluble thrombomodulin levels in animals that received venom iv (A) and ip (B) reveal elevations caused by *B. asper* venom. (C) Treatment with the marimastat and varespladib dual combination therapy (MV) reduces *B. asper*-elevated soluble thrombomodulin levels to values comparable with the control. Where the time of death was the same within experimental groups (e.g. early deaths or complete survival) thrombomodulin levels were quantified for n=3, and where times of death varied, n=5. The data displayed represents means of the duplicate technical repeats plus SDs.

Figure 18:
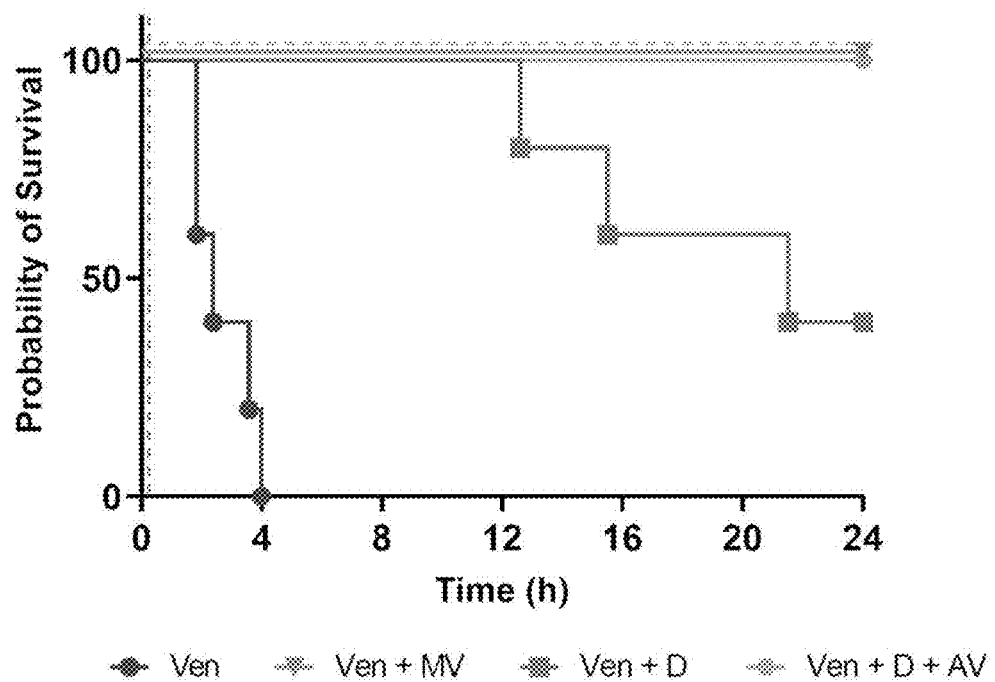

FIG. 18. The therapeutic combination of marimastat and varespladib outperforms the licensed metal chelator DMPS, and shows equipotency with a combination of DMPS and conventional antivenom in a 'challenge then treat' model of envenoming. Kaplan-Meier survival graphs for experimental animals (n=5) that received *E. ocellatus* venom (intraperitoneal administration of 90 µg; 5×iv. $LD_{50}$), followed by delayed drug treatment intraperitoneally 15 mins later. Drug doses were kept constant at 120 µg for each inhibitor used in the solo DMPS (D) treatment group and the marimastat and varespladib combination therapy (MV) group. For the DMPS and antivenom (D+AV) group, experimental animals received 120 µg of DMPS 15 mins after venom, and intravenous antivenom (168 µl of the *E. ocellatus* monospecific antivenom EchiTAbG, MicroPharm Ltd, UK) 1 hr after venom delivery. All DMPS data presented is taken from Albulescu et al. "Preclinical validation of a repurposed metal chelator as an early-intervention therapeutic for hemotoxic snakebite. Sci. Trans. Med. 12, eaay8314 (2020)".

SUMMARY OF THE INVENTION

In a first aspect, the invention provides a method of treating snake bite, the method comprising administering to a subject in need of such treatment a therapeutically effective amount of a combination of varespladib or its prodrug and a drug selected from the group consisting of: marimastat and DMPS.

In a variant of the first aspect, the invention provides a method of treating snake bite, the method comprising administering to a subject in need of such treatment a combination comprising varespladib and a metalloproteinase inhibitor selected from the group consisting of: marimastat and DMPS, in therapeutically effective amounts. Suitably, the combination comprises varespladib, marimastat and DMPS, In a second aspect, the invention provides a pharmaceutical composition comprising a therapeutically effective amount of a combination of varespladib and a metalloproteinase inhibitor selected from the group consisting of: marimastat and DMPS, and a pharmaceutically acceptable carrier.

In a variant of the second aspect, the invention provides a pharmaceutical composition comprising a therapeutically effective amount of a combination of varespladib and one or both metalloproteinase inhibitors: marimastat and DMPS, and a pharmaceutically acceptable carrier.

In a third aspect, the invention provides a kit for treating snake bite, the kit comprising a therapeutically effective amount of a combination of varespladib and a metalloproteinase inhibitor selected from the group consisting of: marimastat and DMPS.

In a variant of the third aspect, the invention provides a kit for treating snake bite, the kit comprising a therapeutically effective amount of a varespladib and one or both metalloproteinase inhibitors: marimastat and DMPS.

Each of the first, second, and third aspects of the invention employs "a therapeutically effective amount of a combination of varespladib and one or both metalloproteinase inhibitors selected from the group consisting of marimastat and DMPS". As considered further below, a "therapeutically effective amount" for the purposes of the present disclosure is an amount sufficient to mitigate at least some of the effects of envenoming by snake bite. Both the varespladib and the selected metalloproteinase inhibitor (or metalloproteinase inhibitors) contribute to this therapeutic effect.

It will be appreciated that in the pharmaceutical compositions of the second aspect of the invention, the combination of varespladib and the metalloproteinase inhibitor (or metalloproteinase inhibitors) is provided in the same composition. In the methods of treatment of the first aspect of the invention the combination of the varespladib and the selected metalloproteinase inhibitor (or inhibitors) may be provided in the same composition, or by means of separate compositions. In the kits of the third aspect of the invention, the combination of the varespladib and the selected metalloproteinase inhibitor (or metalloproteinase inhibitors) will typically be provided in the form of separate compositions.

The pharmaceutical compositions of the second aspect of the invention, and the kits of the third aspect of the invention, are both suitable for putting into practice the methods of treatment of the first aspect of the invention.

The methods of treatment, pharmaceutical compositions, and kits of the invention make use of combinations of therapeutic agents that surprisingly offer improved therapeutic effectiveness as compared to their individual components. This is demonstrated by the results of experimental studies set out in the Examples.

The improved effectiveness of the particular combinations of agents used in the methods, compositions and kits of the invention could not be predicted on the basis of the information available to the public prior to the disclosure of the instant application.

In particular, the inventors have found that the metalloproteinase inhibitors marimastat and DMPS are both unexpectedly effective in their ability to provide therapeutic effects in respect of snake bites. These agents demonstrated better inhibitory potency in vivo than could have been predicted on the basis of in vitro activity. On the other hand, other metalloproteinase inhibitors that exhibited equally impressive activity in vitro did not perform as well in vivo.

The methods of treatment, pharmaceutical compositions, and kits of the invention may be employed in combination with one or more other treatments (for example, in combination with treatment using an appropriate antivenom). Alternatively, methods of treatment, pharmaceutical compositions, and kits of the invention may be employed as the sole treatment for snake bite. It is an advantage of the invention that the methods of treatment, pharmaceutical compositions and kits provided are able to provide useful therapy in respect of a broad spectrum of snake bites. This avoids or reduces the need to identify the particular genus or species of snake responsible for a bite, which may otherwise be necessary when using therapies based upon specific antivenoms.

Not only do the methods of treatment, compositions and kits of the invention provide broad spectrum activity in a manner that cannot be achieved with individual antivenoms, but they also exhibit greater therapeutic potency than the current "gold standard" therapies. Without wishing to be bound by hypothesis, the inventors believe that this greater potency arises as a result of the increased specificity with which these agents are able to counteract to the damaging elements of snake venoms.

The invention further provides other notable advantages as compared to prior art treatments, such as those using antivenoms, in that the therapeutic agents used are amenable to delivery by a wider range of routes of administration. In particular, the methods, compositions and kits of the invention are capable of use by oral administration, which markedly increases their convenience in use, particularly when used by those with little or no medical training, when compared to antivenom therapies which must be administered by injection.

Furthermore, the therapeutic agents used (varespladib and one or both metalloproteinase inhibitors selected from the group consisting of: marimastat and DMPS) have better stability in a range of conditions than do many prior art therapeutic agents. As a result, the compositions and kits of the invention may have improved shelf-life and reduced requirement for cold chain distribution and storage as compared to prior art therapies. This offers significant advantages in practice, in that the compositions and kits of the invention (and so methods of treatment using these compositions and kits) are more likely to be available at an earlier time point post envenoming, as snake bites frequently occur in remote locations.

DETAILED DESCRIPTION OF THE INVENTION

The invention will now be further described with reference to the following definitions, which may be helpful in understanding and practicing the invention. Except for where the context requires otherwise, suggestions set out in respect of a particular aspect or embodiment of the invention should be taken as also applicable to other aspects or embodiments set out herein.

Varespladib

Varespladib (also known as LY315920) is an inhibitor of secretory phospholipase A2 (sPLA2), and in particular the IIa, V and X isoforms of this enzyme.

In the context of the present disclosure, references to varespladib should, except where the context requires otherwise, be taken as encompassing any pharmaceutically acceptable forms of varespladib known to the skilled person, including suitable prodrugs or salts of varespladib.

Particular forms of varespladib that may be utilised in the context of the various aspects and embodiments of the invention include: "varespladib methyl" an orally bioavailable prodrug of varespladib that is particularly suitable for use in embodiments in which varespladib is to be administered orally (after which varespladib methyl undergoes ester hydrolysis to yield biologically active varespladib in vivo); and "varespladib sodium", a sodium salt of varespladib that is particularly suitable for administration by injection (such as intravenous injection).

Varespladib is commercially available from sources including Sigma-Aldrich.

Metalloproteinase Inhibitor

As used herein, the term "metalloproteinase inhibitor" refers to any agent (e.g. compound, drug etc.) that is capable of directly or indirectly inhibiting the activity of a metalloproteinase. An indirect inhibitor includes a chelating agent, such as DMPS, which is capable of inhibiting the activity of metal ion-dependent metalloproteinases.

Marimastat

Marimastat is a metalloproteinase inhibitor, in particular a broad-spectrum matrix metalloproteinase inhibitor.

In the context of the present disclosure, references to marimastat should, except where the context requires otherwise, be taken as encompassing any pharmaceutically acceptable forms of marimastat known to the skilled person, including suitable prodrugs or salts of marimastat.

Marimastat is particularly suitable for oral administration, and so oral formulations of marimastat may be utilised in the various aspects or embodiments of the invention described herein.

Marimastat is commercially available from sources including Sigma-Aldrich.

DMPS 2,3-dimercapto-1-propanesulfonic acid, referred to herein as DMPS, is a chelating agent. As such, it is capable of inhibiting the activity of metal ion-dependent metalloproteinases. In the context of the present disclosure DMPS is classed as a metalloproteinase inhibitor.

In the context of the present disclosure, references to DMPS should, except where the context requires otherwise, be taken as encompassing any pharmaceutically acceptable forms of DMPS known to the skilled person, including suitable prodrugs or salts of DMPS. In particular, references to DMPS should be taken as encompassing its sodium salt monohydrate, also known as Unithiol (which is also known by the trade name Dimaval).

The sodium monohydrate form of DMPS is particularly suitable for oral administration, and so while this salt of DMPS may be utilised in the various aspects and embodiments of the invention, it is particularly suitable for use in those in which DMPS is to be orally administered.

DPMS is commercially available from a range of sources, including sources including Alfa Aesar.

Methods of Treatment in Accordance with the Present Invention

The first aspect of the invention provides a method of treating snake bite. A method in accordance with this aspect of the invention comprises administering to a subject in need of such treatment a therapeutically effective amount of a combination of varespladib and one or both metalloproteinase inhibitors selected from the group consisting of: marimastat and DMPS.

The invention also provides method of treating snake bite, the method comprising administering to a subject in need of such treatment a therapeutically effective amount of varespladib and a therapeutically effective amount of a metalloproteinase inhibitor selected from the group consisting: of marimastat and DMPS.

The invention also provides method of treating snake bite, the method comprising administering to a subject in need of such treatment a therapeutically effective amount of varespladib and a therapeutically effective amount of marimastat and a therapeutically effective amount of DMPS.

The invention also provides method of treating snake bite, the method comprising administering to a subject in need of such treatment a therapeutically effective amount of a combination of varespladib and marimastat.

The invention also provides method of treating snake bite, the method comprising administering to a subject in need of such treatment a therapeutically effective amount of a combination of varespladib and DMPS.

The invention also provides method of treating snake bite, the method comprising administering to a subject in need of such treatment a therapeutically effective amount of a combination of varespladib, marimastat and DMPS.

A further aspect of the invention provides a method of treating snake bite, the method comprising administering to a subject in need of such treatment a combination of or comprising varespladib and a metalloproteinase inhibitor selected from the group consisting of: marimastat and DMPS in a therapeutically effective amount.

There is also provided a method of treating snake bite, the method comprising administering to a subject in need of such treatment a combination of or comprising varespladib and a metalloproteinase inhibitor selected from the group consisting: of marimastat and DMPS in therapeutically effective amounts.

A method of treating snake bite, the method comprising administering to a subject in need of such treatment a therapeutically effective amount of a combination of or comprising varespladib and a metalloproteinase inhibitor selected from the group consisting of: marimastat and DMPS.

In a suitable embodiment, of a method of the invention, the subject is provided with a therapeutically effective amount of a combination of varespladib and marimastat.

In a suitable embodiment of a method of the invention, the varespladib and marimastat are provided in the same composition.

In a suitable embodiment of a method of the invention, the varespladib and marimastat are provided in separate compositions.

In a suitable embodiment of a method of the invention, the subject is provided with a therapeutically effective amount of a combination of varespladib and DMPS.

In a suitable embodiment of a method of the invention, the varespladib and DMPS are provided in the same composition.

In a suitable embodiment of a method of the invention, the varespladib and DMPS are provided in separate compositions.

In a suitable embodiment of a method of the invention, the subject is provided with a therapeutically effective amount of a combination of varespladib, marimastat, and DMPS.

In a suitable embodiment of a method of the invention, the varespladib, marimastat, and DMPS are provided in the same composition.

In a suitable embodiment of a method of the invention, the varespladib, marimastat, and DMPS are provided in separate compositions.

When the therapeutic agents (varespladib and one or both of marimastat and DMPS) are provided in separate compositions, these compositions should be administered such that each of the therapeutic agents is present in the subject's circulation at the same time.

In a suitable embodiment of a method of the invention, when the therapeutic agents are provided in separate compositions, the separate compositions are co-administered.

In a suitable embodiment of a method of the invention, when the therapeutic agents are provided in separate compositions, the separate compositions are administered sequentially.

In a suitable embodiment of a method of the invention, when separate compositions are administered sequentially, the compositions may be administered within an hour of one another. In a suitable embodiment of a method of the invention, when separate compositions are administered sequentially, the compositions may be administered within thirty minutes of one another. In a suitable embodiment of a method of the invention, when separate compositions are administered sequentially, the compositions may be administered within fifteen minutes of one another. In a suitable embodiment of a method of the invention, when separate compositions are administered sequentially, the compositions may be administered within ten minutes of one another. In a suitable embodiment of a method of the invention, when separate compositions are administered sequentially, the compositions may be administered within five minutes of one another. In a suitable embodiment of a method of the invention, when separate compositions are administered sequentially, the compositions may be administered within two minutes of one another. In a suitable embodiment of a method of the invention, when separate compositions are administered sequentially, the compositions may be administered within one minute of one another.

In a suitable embodiment of a method of the invention the combination of or comprising varespladib and a metalloproteinase inhibitor selected from the group consisting of: marimastat and DMPS is provided to the subject in a single incidence of treatment.

In a suitable embodiment of a method of the invention the combination of or comprising varespladib and a metalloproteinase inhibitor selected from the group consisting of: marimastat and DMPS is provided to the subject in multiple incidences of treatment. Suitably, a method of treatment in accordance with this embodiment of the invention may employ two, three, four, five, or more incidences of treatment. The number of incidences of treatment required may be determined by a responsible physician.

A suitable embodiment, a first incidence of treatment (whether this is the sole incidence of treatment, or one of a plurality of incidences of treatment) may occur within about 24 hours, such as within about twelve hours, of envenoming by snake bite. For example, a first incidence of treatment may occur within twenty hours, within fifteen hours, within twelve hours, within ten hours, within eight hours, within six hours, or within five hours of envenoming by snake bite. In a suitable embodiment, such a first incidence of treatment may occur within four hours, within three hours, within two hours, or within one hour of envenoming by snake bite. A first such incidence of treatment may occur within forty-five minutes, within thirty minutes, within fifteen minutes, within ten minutes, or within five minutes of envenoming by snakebite.

In a suitable embodiment of a method of the invention when the combination of varespladib and one or both metalloproteinase inhibitors selected from the group consisting of: marimastat and DMPS is provided to the subject in multiple incidences of treatment, the incidences of treatment may take place within twenty-four hours of one another. In a suitable embodiment of a method of the invention utilising multiple incidences of treatment, the incidences of treatment may take place within eighteen or twelve hours of one another. Suitably, incidences of treatment may take place within ten hours, eight hours, six hours, or five hours of one another. In a suitable embodiment of a method of the invention utilising multiple incidences of treatment, the incidences of treatment may take place within two hours of one another. In a suitable embodiment of a method of the invention utilising multiple incidences of treatment, the incidences of treatment may take place within one hour of one another.

In a suitable embodiment of a method of the invention the varespladib and metalloproteinase inhibitor, or inhibitors, are administered orally.

In a suitable embodiment of a method of the invention the varespladib and metalloproteinase inhibitor, or inhibitors, are administered topically.

In a suitable embodiment of a method of the invention the varespladib and metalloproteinase inhibitor, or inhibitors, are administered by injection.

In a suitable embodiment of a method of the invention the varespladib and metalloproteinase inhibitor, or inhibitors, are administered by intravenous injection.

In a suitable embodiment of a method of the invention the varespladib and metalloproteinase inhibitor, or inhibitors, are administered by intramuscular injection.

In a suitable embodiment of a method of the invention the varespladib and metalloproteinase inhibitor, or inhibitors, are administered by subcutaneous injection.

Each of varespladib, marimastat and DMPS may be administered in the same way (e.g. orally, topically or by injection) or two or more different ways (e.g. one orally and one or more by injection). In suitable embodiments of a method of the invention each of the varespladib and metalloproteinase inhibitor, or inhibitors, are administered orally, topically and/or by injection.

In a suitable embodiment of a method of the invention the combination of or comprising varespladib and a metalloproteinase inhibitor selected from the group consisting of: marimastat and DMPS is administered to the subject by a first route of administration in a first incidence of treatment, and administered by the same route of administration in a second or subsequent incidence of treatment. Merely by way of example, oral administration may be used in both a first incidence of treatment, and also in a second or subsequent incidence of treatment.

In an alternative embodiment of a method of the invention, the combination of varespladib and one or both metalloproteinase inhibitors selected from the group consisting of: marimastat and DMPS is administered to the subject by a first route of administration in a first incidence of treatment, and administered by a different route of administration in a second or subsequent incidence of treatment. In such an embodiment, oral administration may be used for a first incidence of treatment, and administration by injection used for a second or subsequent incidence of treatment, or vice versa.

In a suitable embodiment of a method of the invention the varespladib is provided in a dose of up to 10 g per day. In a suitable embodiment of a method of the invention, the amount of varespladib administered is a dose of between approximately 10 mg and approximately 10 g per day. For example, varespladib may be administered in a dose of between around 500 mg and 7 g per day. Suitably, varespladib may be administered in a dose of between around 750 mg and 5 g per day.

In a suitable embodiment of a method of the invention marimastat is provided in a dose of up to 10 g per day. In a suitable embodiment of a method of the invention, the amount of marimastat administered is a dose of between approximately 10 mg and approximately 10 g per day. For example, marimastat may be administered in a dose of between around 500 mg and 7 g per day. Suitably, marimastat may be administered in a dose of between around 750 mg and 5 g per day.

In a suitable embodiment of a method of the invention DMPS is provided in a dose of up to 10 g per day. In a suitable embodiment of a method of the invention, the amount of DMPS administered is a dose of between approximately 10 mg and approximately 10 g per day. For example, DMPS may be administered in a dose of between around 500 mg and 7 g per day. Suitably, DMPS may be administered in a dose of between around 750 mg and 5 g per day. Suitably, the DMPS is administered in a dose between 500 mg and 2000 mg. The inventors have determined that an oral dose of up to 1,500 mg is well tolerated and safe. Suitably, the DMPS is administered in a dose of 1500 mg. The dosing frequency for oral administration may be six times per day (4-hourly dosing). For the intravenous formulation of DMPS an individual dose of up to 10 mg/kg intravenous may be used. The dosing frequency for intravenous administration of DMPS may be six times per day (4-hourly dosing), although a continuous intravenous infusion may also be used. In certain scenarios, an intravenous loading dose may be administered followed by continuation with regular oral dosing of DMPS.

It will be appreciated that a therapeutically effective amount of a combination of therapeutic agents as required by the methods of treatment of the invention may be established over multiple incidences of treatment. In such an embodiment, a single incidence of treatment provides a fraction of a therapeutically effective amount, but the total number of incidences of treatment leads to a therapeutically effective amount being administered to the subject. Further incidences of treatment may be continued until a desired outcome is achieved.

Alternatively, a single incidence of treatment may provide a therapeutically effective amount of the combination of selected therapeutic agents to the subject. In this case, further incidences of treatment may not be required.

Pharmaceutical Compositions in Accordance with the Present Invention

The second aspect of the invention provides a pharmaceutical composition. A pharmaceutical composition in accordance with this aspect of the invention comprises a therapeutically effective amount of a combination of varespladib and one or both metalloproteinase inhibitors selected from the group consisting of: marimastat and DMPS, and a pharmaceutically acceptable carrier.

In a suitable embodiment a pharmaceutical composition in accordance with the invention comprises a therapeutically effective amount of a combination of varespladib and marimastat, and a pharmaceutically acceptable carrier.

In a suitable embodiment a pharmaceutical composition in accordance with the invention comprises a therapeutically effective amount of a combination of varespladib and DMPS, and a pharmaceutically acceptable carrier.

In a suitable embodiment a pharmaceutical composition in accordance with the invention comprises a therapeutically effective amount of a combination of varespladib and both marimastat and DMPS, and a pharmaceutically acceptable carrier.

A suitable form of a pharmaceutical composition of the invention may be selected with reference to a number of factors. These include the therapeutic agents to be incorporated in the pharmaceutical composition, the doses of the therapeutic agents required, and the route of administration by which the pharmaceutical composition is to be used.

These factors, and particularly the consideration of the route of administration to be used, may be taken into consideration when selecting a suitable form of the therapeutic agents to be incorporated in a pharmaceutical composition of the invention.

For example, in the case of pharmaceutical compositions of the invention for oral administration, it may be preferred to use varespladib in the form of the varespladib salt varespladib sodium. The properties of this salt of varespladib make it particularly suited to administration by injection.

On the other hand, in the case of pharmaceutical compositions of the invention for administration by injection, it may be preferred to use varespladib in the form of the prodrug varespladib methyl, since this prodrug form of varespladib is particularly suited to oral administration.

The same factors may also be taken into consideration when selecting a suitable pharmaceutically acceptable carrier for use in a pharmaceutical composition of the invention. Pharmaceutically acceptable carriers useful herein are conventional. Remington's Pharmaceutical Sciences, by E. W. Martin, Mack Publishing Co, Easton, PA, 15th Edition (1975), describes compositions and formulations suitable for pharmaceutical delivery of the compounds herein disclosed.

In a suitable embodiment, a pharmaceutical composition of the invention is for oral administration. Without limitation, the forms of such pharmaceutical compositions for oral administration, and examples of pharmaceutically acceptable carriers that may be employed in such compositions for oral administration, may be selected with reference to the following examples.

Solid dosage forms for oral administration include capsules, tablets (also called pills), powders and granules. In such solid dosage forms, the active compound is typically mixed with at least one inert, pharmaceutically acceptable excipient or carrier such as sodium citrate or dicalcium phosphate and/or one or more fillers, extenders, humectants, dissolution aids, ionic surface active agents. Therapeutic agents may also be in micro-encapsulated form, if appropriate, with one or more excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers.

Compositions suitable for oral administration (e.g., by ingestion) may be presented as discrete units such as capsules, cachets or tablets, each containing a predetermined amount of the therapeutic agent; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g. compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach In a suitable embodiment, a pharmaceutical composition of the invention is for injection. Suitably, the pharmaceutical composition may be for intravenous injection, for intramuscular injection, or for subcutaneous injection. Without limitation, the forms of such pharmaceutical compositions for injection, and examples of pharmaceutically acceptable carriers that may be employed in such compositions for injection, may be selected with reference to the following examples.

Compositions suitable for injection (including cutaneous, subcutaneous, intramuscular, intravenous and intradermal injection), include aqueous and non-aqueous isotonic, pyrogen-free, sterile injection solutions which may contain antioxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such compositions include sodium chloride Injection, Ringer's Solution, or Lactated Ringer's Injection. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Compositions may be in the form of liposomes or other microparticulate systems which are designed to target the active compound to blood components or one or more organs.

In a suitable embodiment, a pharmaceutical composition of the invention is for topical administration. Without limitation, the forms of such pharmaceutical compositions for topical administration, and examples of pharmaceutically acceptable carriers that may be employed in such compositions for topical administration, may be selected with reference to the following examples.

Compositions suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical compositions may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulation.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Pharmaceutical compositions of the invention may also include antioxidants and/or preservatives. As antioxidants may be mentioned tocopherols, butylated hydroxyanisole, butylated hydroxytoluene, sulfurous acid salts (e.g. sodium sulfate, sodium bisulfite, acetone sodium bisulfite, sodium metabisulfite, sodium sulfite, sodium formaldehyde sulfoxylate, sodium thiosulfate) and nordihydroguaiareticacid. Suitable preservatives may for instance be phenol, chlorobutanol, benzylalcohol, methyl paraben, propyl paraben, benzalkonium chloride and cetylpyridinium chloride.

The preceding considerations are also applicable to the kits of the third aspect of the invention.

The amount of varespladib, marimastat, or DMPS to be incorporated in a suitable embodiment of a pharmaceutical composition of the invention may be varied with reference to a number of factors, including the route by which the pharmaceutical composition is to be administered. General principles by which such suitable amounts of varespladib, marimastat, or DMPS may be determined experimentally will be well known to those of skill in the art.

Merely by way of example, in a suitable embodiment a pharmaceutical composition of the invention may be formulated such that the amount of varespladib provided in a therapeutically effective amount is between approximately 10 mg and approximately 10 g per day. For example, a pharmaceutical composition of the invention may be formulated to provide a therapeutically effective amount of varespladib that is between around 500 mg and 7 g per day. Such a pharmaceutical composition may be formulated to provide a therapeutically effective amount of varespladib that is between about 750 mg and 5 g per day.

Similarly, in a suitable embodiment a pharmaceutical composition of the invention may be formulated such that the amount of marimastat provided in a therapeutically effective amount is between approximately 10 mg and approximately 10 g per day. For example, a pharmaceutical composition of the invention may be formulated to provide a therapeutically effective amount of marimastat that is between around 500 mg and 7 g per day. Such a pharmaceutical composition may be formulated to provide a therapeutically effective amount of marimastat that is between about 750 mg and 5 g per day.

Further, in a suitable embodiment a pharmaceutical composition of the invention may be formulated such that the amount of DMPS provided in a therapeutically effective amount is between approximately 10 mg and approximately 10 g per day. For example, a pharmaceutical composition of the invention may be formulated to provide a therapeutically effective amount of DMPS that is between around 500 mg and 7 g per day. Such a pharmaceutical composition may be formulated to provide a therapeutically effective amount of DMPS that is between about 750 mg and 5 g per day. Such a pharmaceutical composition may be formulated to provide a therapeutically effective amount of DMPS of about 1500 mg per day.

It will be appreciated that a suitable pharmaceutical composition of the invention may be used in a method of treatment of the invention, or may be provided in a kit of the invention.

Kits in Accordance with the Present Invention

The third aspect of the invention provides a kit for use in treating snake bite. A kit in accordance with this aspect of the invention comprises a therapeutically effective amount of a combination of varespladib and one or both metalloproteinase inhibitors selected from the group consisting of: marimastat and DMPS.

In a suitable embodiment, a kit in accordance with the invention comprises varespladib and the selected metalloproteinase inhibitor (or metalloproteinase inhibitors) in separate compositions. In the case that both marimastat and DMPS are present in a kit of the invention, these therapeutic agents may be provided in the same composition, or in separate compositions.

In a suitable embodiment a kit in accordance with the invention comprises: varespladib and a pharmaceutically acceptable carrier; and marimastat and a pharmaceutically acceptable carrier.

In a suitable embodiment a kit in accordance with the invention comprises: varespladib and a pharmaceutically acceptable carrier; and DMPS and a pharmaceutically acceptable carrier.

In a suitable embodiment a kit in accordance with the invention comprises: varespladib and a pharmaceutically acceptable carrier; and both marimastat and DMPS and a pharmaceutically acceptable carrier.

In a suitable embodiment a kit in accordance with the invention comprises: varespladib and a pharmaceutically acceptable carrier, marimastat and a pharmaceutically acceptable carrier, and DMPS and a pharmaceutically acceptable carrier.

The therapeutic agents provided in the kits of the invention may be formulated for any suitable route of administration.

A kit in accordance with the present invention may comprise varespladib formulated for oral administration. Alternatively, a kit in accordance with the present invention may comprise varespladib formulated for topical administration. A kit in accordance with the present invention may comprise varespladib formulated for administration by injection. In such an embodiment, the varespladib may be formulated for intravenous injection, for intramuscular injection, or for subcutaneous injection.

A kit in accordance with the present invention may comprise marimastat formulated for oral administration. A kit in accordance with the present invention may comprise marimastat formulated for topical administration. A kit in accordance with the present invention may comprise marimastat formulated for administration by injection. In such an embodiment, the marimastat may be formulated for intravenous injection, for intramuscular injection, or for subcutaneous injection.

A kit in accordance with the present invention may comprise DMPS formulated for oral administration. As an alternative, a kit in accordance with the present invention may comprise DMPS formulated for topical administration. A kit in accordance with the present invention may comprise DMPS formulated for administration by injection. In such an embodiment, the DMPS may be formulated for intravenous injection, for intramuscular injection, or for subcutaneous injection.

The different therapeutic agents present in a kit of the invention may each be formulated for the same route of administration. Alternatively, the different therapeutic agents present in a kit of the invention may each be formulated for different routes of administration. In such an embodiment, the way in which each therapeutic agent is formulated may be selected independently of one another from the options set out above.

A kit of the invention may comprise an amount of varespladib that is between approximately 10 mg and approximately 10 g. For example, a kit of the invention may comprise an amount of varespladib that is between around 500 mg and 7 g. Suitably, a kit of the invention comprises an amount of varespladib that is between about 750 and 5 g per day.

Similarly, in a suitable embodiment a kit of the invention may comprise an amount of marimastat that is between approximately 10 mg and approximately 10 g. For example, a kit of the invention may comprise an amount of marimastat that is between around 500 mg and 7 g. Suitably, a kit of the invention comprises an amount of marimastat that is between about 750 and 5 g per day.

Further, in a suitable embodiment a kit of the invention may comprise an amount of DMPS that is between approximately 10 mg and approximately 10 g. For example, a kit of the invention may comprise an amount of DMPS that is between around 500 mg and 7 g. Suitably, a kit of the invention comprises an amount of DMPS that is between about 750 and 5 g per day. Suitably, a kit of the invention comprises an amount of DMPS that is about 1500 mg per day.

Snake Bite

Treatment in accordance with the present invention, and the use of the compositions or kits of the invention, is useful in the treatment of bites from a wide variety of snakes.

Merely by way of example, in a suitable embodiment, the snake bite is from a snake native to North America.

In a suitable embodiment the snake bite is from a snake of a genus selected from the group consisting of: *Crotalus; Sistrurus; Agkistrodon; Micrurus*; and *Micruroides*.

In a suitable embodiment the snake bite is from a viper. In a suitable embodiment the snake bite is from a snake of a genus selected from the group consisting of: *Crotalus; Sistrurus;* and *Agkistrodon*. In the case of a snake bite from a snake of genus *Crotalus*, the bite may be from a snake selected from the group consisting of: *Crotalus atrox, Crotalus adamanteus, Crotalus cerastes, Crotalus enyo, Crotalus horridus, Crotalus lepidus, Crotalus mitchellii, Crotalus molossus, Crotalus pricei, Crotalus ruber, Crotalus scutulatus, Crotalus tigris, Crotalus viridis* and *Crotalus willardi*. In a suitable embodiment of a case of a snake bite from a snake of genus *Crotalus*, the bite may be from a snake selected from the group consisting of: *Crotalus atrox, Crotalus adamanteus, Crotalus horridus,* and *Crotalus scutulatus*.

In suitable embodiments, the snake bite is from a snake selected from the group consisting of: *Crotalus atrox, Crotalus adamanteus, Crotalus cerastes, Crotalus enyo, Crotalus horridus, Crotalus lepidus, Crotalus mitchellii, Crotalus molossus, Crotalus pricei, Crotalus ruber, Crotalus scutulatus, Crotalus tigris, Crotalus viridis, Crotalus willardi, Sistrurus miliarius* and *Agkistrodon contortrix*.

In suitable embodiments, the snake bite is from a snake selected from the group consisting of: *Crotalus atrox, Crotalus scutulatus, Crotalus adamanteus, Crotalus horridus, Sistrurus miliarius* and *Agkistrodon contortrix*.

It will be appreciated that snake bites, and particularly those of many of the species of snake referred to herein, can give rise to a wide range of pathologies, including (but not limited to) causing swelling, local tissue damage, and bleeding and clotting disorders. On occasions, they can even prove to be lethal. However, the results generated by the inventors demonstrate that the methods, compositions and kits of the invention are able to decrease the incidence and/or severity of pathologies occurring as a result of envenoming, and also to reduce mortality or morbidity.

Accordingly, references to "a therapeutically effective amount" of the combinations of varespladib, marimastat and/or DMPS considered in each of the first, second, and third aspects of the invention may be construed with reference to the likely outcome of envenoming that would occur without such treatment. Thus, a therapeutically effective amount, in the context of the present invention should be construed as an amount that is sufficient to bring about at least some reduction or alleviation in the level of a pathology that would otherwise arise as a result of envenoming by snake bite. A therapeutically effective amount may be an amount sufficient to reduce or alleviate swelling that results from envenoming. A therapeutically effective amount may be an amount sufficient to reduce or alleviate local tissue damage that results from envenoming. A therapeutically effective amount may be an amount sufficient to reduce or alleviate bleeding or clotting disorders that result from envenoming. A therapeutically effective amount may be an amount sufficient to reduce incidences of morbidity that result from envenoming.

EXAMPLES

Study 1
Methods
Venoms

*Echis ocellatus, Echis carinatus* and *Bitis arietans* venoms were sourced from wild-caught specimens maintained in the herpetarium of the Liverpool School of Tropical Medicine, while *Daboia russelii, Bothrops asper, Crotalus atrox, Crotalus adamanteus, Crotalus horridus, Sistrurus miliarius* and *Agkistrodon contortrix* venoms were sourced from the historical venom collection in the herpetarium of the Liverpool School of Tropical Medicine. Crude venoms were lyophilized and stored at 4° C. to ensure long term stability. Prior to use, venoms were resuspended to 1 mg/ml in PBS (pH 7.4) for the described experiments.

Drug Preparations for In Vitro Studies

All drugs were reconstituted in DMSO to 10 mM stocks stored at −20° C. Daughter plates were made at 1 mM concentrations in a 384-well format to allow the creation of assay ready plates using a Viaflo 384 electronic pipette (Integra) for all screening against *Echis ocellatus*. Both daughter plates and assay ready plates were stored at −20° C., with the latter used within a month.

Varespladib (Cat no: SML1100) and marimastat (Cat no: M2699) were purchased from Sigma-Aldrich. DMPS (2,3-dimercapto-1-propanesulfonic acid sodium salt monohydrate, 95%, Cat no: H56578) was sourced from Alfa Aesar. The remaining drugs, defined as either matrix metalloproteinase inhibitors (MMPi; numbered sequentially herein as MMPi1-MMPi10) or drugs predicted to have metalloproteinase inhibitory properties based on drug annotation (numbered sequentially herein as "drug A-drug C") were all sourced from MedChemExpress. For in vitro screening against venoms from North American pit vipers (i.e. *Crotalus* spp.) all drugs were diluted to 2.5 mM concentrations from the 10 mM stocks as described above to allow for the creation of assay ready plates. The North American ovine Fab polyclonal antibody CroFab antivenom (BTG, Lot: BN 201296) was also utilised for these experiments. Due to the distinct nature of this therapeutic (i.e. vs small molecule drugs), a dilution of 2.5 mg/ml of antivenom antibodies was utilised for assay ready plates, and stored at −20° C. before use.

In Vitro Snake Venom Metalloproteinase Assay

The snake venom metalloproteinase activity in the presence of inhibitors or vehicle control (DMSO), was measured using a quenched fluorogenic substrate (ES010, R&D Biosystems). Briefly, the substrate was used at a final concentration of 10 μM (supplied as a 6.2 mM stock), which had a total volume per well of 91 μl. The substrate was suspended in reaction buffer (150 mM NaCl, 50 mM Tris-HCl pH 7.5). Reactions consisted of 1 μg/reaction of venom (1 μg in 15 μl PBS) co-incubated with 0.91 μl of 1 mM of inhibitor, both added using the VIAFLO 384 (Integra). The 384 well plate (Greiner) was spun down and incubated at 37° C. for 25 minutes with an additional 5 minutes on the bench to acclimate to room temperate before the final addition of the freshly diluted fluorogenic substrate (75 μl of 12.1 μM). All additions above were made using the VIAFLO 384. The plate was immediately run on an Omega FluoSTAR (BMG Labtech) instrument at an excitation wavelength of 320 nm and emission wavelength of 405 nm at 25° C. for 45 minutes. The end-reads were calculated for each sample and normalised to DMSO and 10 μM marimastat controls to allow for percentage metalloproteinase activity read out (DMSO 100% and marimastat 0%); this time point was chosen as the time where all fluorescence curves had typically reached a plateau (maximum fluorescence). Strong hits were determined as those with less than 20% metalloproteinase activity of the venom and mediocre hits between 20 and 50%.

To provide context and to facilitate inhibitory comparisons against the current gold-standard therapeutic currently available in North America (i.e. the FDA-approved polyclonal antibody therapy CroFab), the same assay as described above was undertaken for three medically important *Crotalus* species from North America (*C. atrox, C. adamanteus*, and *C. horridus*) using the drugs marimastat, DMPS and "MMPi5" and a commercially available antivenom, CroFab, with the following modifications: (i) CroFab antivenom was diluted in sterile PBS to 2.5 mg/mL and 0.91 μl added to a 384 well plate (Greiner), (ii) all three drugs were diluted to a concentration of 2.5 mM in DMSO and 0.91 μl of this dilution co-incubated with 1 μg/well of venom. The remaining assay protocol with respects to fluorogenic substrate preparation, plate-read settings and data processing was the same as described above.

Murine In Vivo Preclinical Studies

All animal experiments were conducted using protocols approved by the Animal Welfare and Ethical Review Boards of the Liverpool School of Tropical Medicine and the University of Liverpool, and performed in specific pathogen-free conditions under licensed approval of the UK Home Office and in accordance with the Animal [Scientific Procedures] Act 1986 and institutional guidance on animal care. Experimental design was based upon refined World Health Organization-recommended protocols, with the observers being blinded to the experimental groups. Drug stocks were freshly prepared to allow for a ratio of 1:1.33 venom to inhibitor. Drugs were sourced from MedChemExpress and re-suspended to make 1 mg/ml in PBS from 10 mM DMSO stocks (final DMSO percentage in the injection was 5.5 to 10.1%), with the exception of Marimastat, DMPS and Varespladib, which were sourced from Sigma-Aldrich (Cat no: M2699, H56578 and SML1100) and resuspended to 1 mg/ml stock in water (marimastat) or PBS (DMPS) or 5 mg/ml in DMSO (Varespladib).

Co-Incubation Model of Preclinical Efficacy

The intravenous median lethal dose (venom $LD_{50}$) for *E. ocellatus* (Nigeria) of 17.85 μg per mouse was previously determined. Mice were challenged with 45 μg of *E. ocellatus* venom (2.5×the intravenous $LD_{50}$ dose) in a refined version of the World Health Organization-recommended antivenom efficacy experiments. Groups of five male 18-22 g CD-1 mice (Charles River, UK) received experimental doses that consisted of either (a) venom only (2.5×$LD_{50}$ dose), (b) venom and drug (60 μg) or (c) drug only. All experimental doses were prepared to a volume of 200 μl in PBS and incubated at 37° C. for 30 mins prior to their intravenous injection via the tail vein. Animals were monitored for 6 hours and euthanized upon observation of humane endpoints (seizure, pulmonary distress, paralysis, hemorrhage). Deaths, time of death, and survivors were recorded; where "deaths/time of death" represents the implementation of euthanasia based on the defined humane endpoints.

The same murine preincubation model was used to assess the efficacy of distinct toxin family inhibiting drugs in comparison with a drug combination. Groups of five mice received experimental doses that consisted of either: (a) venom only (2.5×$LD_{50}$ dose of *E. ocellatus* venom; 45 μg); (b) venom and solo drug (60 μg of either the snake venom metalloproteinase inhibitor marimastat or the phospholipase A2 inhibitor varespladib); (c) solo drug-only (60 μg of marimastat or varespladib, as control); (d) venom and a mix of the two drugs (60 μg each of marimastat and varespladib); or (e) a mix of the two drugs only (60 μg each, as control). Marimastat was dissolved in water at 1 mg/ml, while varespladib was prepared as a 5 mg/ml stock in DMSO (2.5% in the final dose) due to solubility. All experimental doses were prepared to a volume of 200 μl in PBS and incubated at 37° C. for 30 min prior to their intravenous injection via the tail vein. Animals were monitored for 6 h, and euthanized via rising concentrations of $CO_2$ upon observation of previously defined humane end points that are predicators of lethality (e.g., seizure, pulmonary distress, paralysis, hemorrhage). Deaths, time of death, and survivors were recorded; where death/time of death represents the implementation of euthanasia based on defined humane end points.

Thereafter, the same murine animal model was used to explore the efficacy of the same snake venom metalloproteinase and phospholipase A2 inhibiting drugs as solo and combination treatments against North American pit viper venoms. The intravenous median lethal dose (venom $LD_{50}$) for *C. atrox, C. scutulatus, S. miliariius* and *A. contortrix* venoms was previously determined (3.79 μg, 0.17 μg, 4.87 μg and 4.99 μg per mouse, respectively). For each of the four venoms, groups of five mice received experimental doses that consisted of either: (a) venom only (2.5×$LD_{50}$ dose); (b) venom and solo drug (60 μg of either the snake venom metalloproteinase inhibitors marimastat or DMPS, or the phospholipase A2 inhibitor varespladib); (c) venom and a mix of marimastat and varespladib (60 μg of each drug); or (d) venom and a mix of DMPS and varespladib (60 μg of each drug). Marimastat was dissolved in water at 1 mg/ml, DMPS was dissolved in sterile PBS at 1 mg/ml, while varespladib was prepared as a 5 mg/ml stock in DMSO (2.5% in the final dose) due to solubility. As described above, all experimental doses were prepared to a volume of 200 μl in PBS and incubated at 37° C. for 30 min prior to their intravenous injection via the tail vein. Animals were monitored for 6 h, and euthanized via rising concentrations of $CO_2$ upon observation of previously defined humane end points that are predicators of lethality (e.g., seizure, pulmonary distress, paralysis, hemorrhage). Deaths, time of death, and survivors were recorded; where death/time of death represents the implementation of euthanasia based on defined humane end points.

Preclinical Efficacy Via a 'Challenge then Treat' Model of Envenoming

To better mimic a snakebite scenario, mice were initially challenged with venom, followed by the delayed administration of a single drug or a combination of drugs, as previously described. The venom challenge dose was increased to ensure complete lethality in the venom-only control group occurred within 4-5 hours. Groups of five male 18-22 g CD-1 mice (Charles River, UK) were injected with venom (100 μl final volume), followed by a drug dose that was scaled up accordingly after 15 min. We tested DMPS versus the DMPS and varespladib drug combination against *Echis ocellatus* venom in this model, as well as the marimastat and varespladib combination against several viper species. For *E. ocellatus, E. carinatus* and *B. arietans* venoms we challenged mice with 5×i.v. $LD_{50}$ doses (90, 95 and 108 μg, respectively), while higher doses were required to cause lethality with *B. asper* (303 μg, ~16×i.v. $LD_{50}$s) and *D. russelii* (13×i.v. $LD_{50}$, 105 μg) venoms in this model. All intraperitoneal venom doses consisted a final volume of 100 µl in PBS. Drug doses were scaled up from 60 µg/mouse in the preincubation experiments outlined above to 120 µg/mouse here, in line with the (at least) doubling of the venom challenge dose from 2.5×LD$_{50}$ to 5×LD$_{50}$ (i.e., for $E.$ ocellatus, E. carinatus and B. arietans). All inhibitor doses were delivered intraperitoneally 15 min after venom injection and consisted of 200 µl final volumes. The experimental groups comprised mice receiving: (a) venom only+200 µl PBS (15 min later); (b) venom+drug (120 µg, 15 min later); (c) sham (100 µl PBS)+drug (120 µg, 15 min later); (d) venom+drug combination (120 µg each, 15 min later); and (e) sham (100 µl PBS)+drug combination (120 µg each, 15 min later). Experimental animals were monitored for 24 h, with humane end points for euthanasia, and data recording, performed as described above.

Results

1. In Vitro Selection of Snake Venom Metalloproteinase Inhibitors

The ability of several rationally-selected potential inhibitors of metalloproteinases (e.g. matrix metalloproteinase inhibitors, metal chelators, aminopeptidase inhibitors, etc) to inhibit snake venom metalloproteinase activity was tested in vitro in a kinetic fluorogenic assay. A medically important metalloproteinase-rich snake venom was chosen for testing, that of *Echis ocellatus* (the West-African saw-scaled viper). The inhibitors were selected based on pre-defined drug target descriptions from a commercially available library of repurposed drugs sourced from MedChem Express and the scientific literature.

The variation of activity for the known matrix metalloproteinase inhibitor (MMPi) drugs ("MMPi 1 to MMPi 10") was unexpected. Only three drugs presented inhibition of venom at high levels, defined as reducing the percentage of venom metalloproteinase activity to 20% or lower (MMPi 1, MMPi 2 and marimastat), with the vast majority of MMP inhibitors resulting in little to moderate inhibition, as evidenced by the percentage metalloproteinase activity remaining at >75% (FIG. 1). These findings demonstrate that the metalloproteinase inhibitory potency of different MMPi drugs is variable and unpredictable. An additional four drugs not defined as MMPis, based on target site knowledge, showed similarly potent levels of inhibition of venom metalloproteinase activity to marimastat, MMPi1 and MMPi2 (i.e. reduced venom activity to <20%; "drug A", "drug B", "drug C" and the metal chelator DMPS; FIG. 1). Based on these results, these four drug hits alongside the aforementioned three MMPi's were progressed into in vivo testing. As anticipated, the control drug employed during in vitro screening, the phospholipase A2 inhibitor varespladib, had no inhibitory effect against venom metalloproteinase activity (FIG. 1).

2. In Vivo Efficacy of Metalloproteinase Inhibitors

Strong drug hits, those defined as inhibiting >80% of the venom activity in the previously described in vitro metalloproteinase assay (FIG. 1), were next progressed into murine preclinical efficacy studies, to assess their ability to prevent venom-induced lethality in vivo. We used an established in vivo model of envenoming to test the efficacy of the seven snake venom metalloproteinase toxin inhibitors identified. This model consisted of the preincubation of the test drug with venom, followed by intravenous injection of the mixture into groups of five male CD-1 mice (18-20 g) via the tail vein followed by 6 hour monitoring, and is based on principles laid out in the gold standard method of preclinical efficacy recommended by the World Health Organization.

We used the murine preincubation model to test the ability of our in vitro drug hits to prevent venom-induced lethality in mice challenged with the same 2.5×median lethal dose (LD$_{50}$) of *E. ocellatus* venom (45 µg). All five of the experimental animals receiving only *E. ocellatus* venom succumbed to the lethal effects of the venom rapidly (i.e. within 60 mins; FIG. 2). Among the tested drug hits, only marimastat and DMPS were able to effectively prevent lethality in our animal model, with all animals surviving in the DMPS group and only one death recorded at 216 min in the marimastat group (FIGS. 2C and 2F). All other strong drug hits identified in the in vitro metalloproteinase activity screening experiments displayed limited efficacy against the lethal effects of *E. ocellatus* venom (FIGS. 2A, 2B, 2D, 2E and 2G), despite comparable in vitro inhibitory profiles (FIG. 1). Based on these results derived from rational testing, DMPS and marimastat were retained for exploration as metalloproteinase inhibiting components of new therapeutic drug combinations for snakebite.

3. The Therapeutic Combination of Marimastat and the Phospholipase A2 Inhibitor Varespladib Enhances the Preclinical Efficacy of Each Therapeutic Component Because snake venoms are complex mixtures of distinct toxin types, a snake venom metalloproteinase inhibitor may not be highly efficacious as a solo therapy against certain venoms due to the potential toxicity imparted by members of distinct toxin families found in the same venom. One such important toxin family is the phospholipase A2 toxins, which like metalloproteinases, are typically found in the venom of all snakes in reasonably high abundance. These toxins are pathogenic and, recent studies have shown that the drug varespladib is capable of inhibiting toxin phospholipase A2 activity in vitro, and that varespladib provides varying degrees of preclinical protection against certain snake venoms in animal models. Thus, we speculated that combining a metalloproteinase inhibitor with a phospholipase A2 inhibitor might provide enhanced efficacy against snakebite envenoming (and potentially against more diverse snake species), than each drug alone.

We used the same murine preincubation efficacy model to first test the ability of marimastat and varespladib as solo therapies to prevent venom-induced lethality in mice challenged with the same 2.5×median lethal dose (LD$_{50}$) of *E. ocellatus* venom (45 µg). All five of the experimental animals receiving only *E. ocellatus* venom succumbed to the lethal effects of the venom within 50 min (FIG. 3). Both the phospholipase A2-inhibitor varespladib and the snake venom metalloproteinase-inhibitor marimastat (60 µg inhibitor/mouse) prolonged the survival of experimentally envenomed animals (FIG. 3 left and middle). However, marimastat conferred substantially greater protection than varespladib, as only one experimental animal succumbed towards the end of the experimental time frame of 6 h (death at 216 min), and the remaining four survived (FIG. 3 left), while treatment with varespladib failed to prevent lethality over the full experimental time course, with two early deaths (5 and 9 min) and three later deaths (67, 210 and 341 min vs <50 min for the venom-only control) observed (FIG. 3 middle). Inhibitor-only controls revealed no obvious signs of acute toxicity of either drug, as experimental animals survived without ill effects and exhibited normal behaviors throughout the 6 h treatment period (dashed lines in FIG. 3). When assessing the preclinical efficacy of the inhibitor combination consisting of the two drugs simultaneously—i.e. marimastat and varespladib (60 µg each)—against the lethal effects of *E. ocellatus* venom, we observed the survival of all experimental animals until the end of the experiment (FIG. 3 right), demonstrating that this combination of the metalloproteinase inhibitor marimastat with the phospholipase inhibitor varespladib results in increased efficacy compared with the therapeutic use of each inhibitory drug alone.

4. The Combination of DMPS with the Phospholipase A2 Inhibitor Varespladib Enhances the Preclinical Efficacy of the Solo Therapy The use of DMPS as a solo therapy provided complete protection against the lethal effects of *Echis ocellatus* venom in the previously described 6 hour intravenous preincubation model (FIG. 2). Thus, to assess whether the combination of DMPS with varespladib confers increased efficacy over DMPS alone, we required use of a more challenging model of efficacy where venom is first administered intraperitoneally followed by the delivery of therapy after a delay, followed by monitoring for 24 hours. This model more accurately recapitulates an envenoming scenario. Thus, we challenged groups of mice intraperitoneally with 90 µg (the equivalent of 5×the intravenous $LD_{50}$ dose) of *E. ocellatus* venom, followed by the administration of an intraperitoneal dose (120 µg) of DMPS 15 minutes later. All experimental animals were then monitored for signs of envenoming for 24 h, along with those from the venom-only and drug-only control groups. These experiments were then repeated using the therapeutic combination consisting of DMPS and varespladib (120 µg of each drug).

None of the animals receiving DMPS alone displayed any adverse effects over the 24 hour monitoring period, while the venom-only group succumbed to the lethal effects of the venom within 4 hours (FIG. 4). The delayed dosing of DMPS protected against venom-induced lethality for over 12 hours after envenoming (~8 hours post-lethality of the venom only control group), though only two of the five experimental animals survived to the end of the experiment at 24 hours (FIG. 4 left). Contrastingly, the therapeutic combination of DMPS and varespladib resulted in prolonged survival of experimentally envenoming animals. With the exception of one early experimental death (~3 hrs), the remaining mice survived for the entirety of the experimental window (FIG. 4 right), surpassing the efficacy of DMPS alone. These results demonstrate that the therapeutic combination of DMPS with varespladib confers enhanced efficacy over DMPS alone in a robust preclinical model mimicking a snakebite scenario.

5. The Therapeutic Combination of Marimastat and Varespladib Provides Potent Preclinical Efficacy Against Venoms from a Variety of Diverse Viper Snake Species We next tested the marimastat and varespladib combination therapy in the same preclinical 'challenge then treat' model of envenoming as described above; i.e. where the venom is first administered intraperitoneally and then the test therapy is administered intraperitoneally separately after venom challenge. We used venom sourced from five geographically distinct, medically important, viper snake species (*Echis ocellatus* [Africa], *Bitis arietans* [Africa], *Daboia russelii* [Asia], *Echis carinatus* [Asia], *Bothrops asper* [Americas]) in doses equivalent to at least 5×the intravenous (i.v.) median lethal dose ($LD_{50}$) dose followed, 15 min later, by a single dose of the inhibitor mixture (120 µg of both marimastat and varespladib). Experimental animals were then monitored for 24 hours. For *E. ocellatus, E. carinatus* and *B. arietans* venoms we challenged mice with 5×i.v. $LD_{50}$ doses (90, 95, and 108 µg of venom, respectively), while higher venom doses were required for *B. asper* (303 µg, equivalent to ~16×i.v. $LD_{50}$ or 3×i.p. $LD_{50}$) and *D. russelii* (13×i.v. $LD_{50}$, 105 µg) to ensure mortality occurred within 7 hours, thus leaving a 17 hour window for measuring prolonged survival in the treatment groups.

All of the venom-only groups succumbed to the lethal effects of envenoming within 4 hours, with the exception of two mice receiving *D. russelii* venom (mortality at ~7 h), while experimental animals dosed with only the inhibitor combination (i.e., treatment control) survived for the duration of the experiment (24 h) with no apparent adverse effects (FIG. 5). Across all of the diverse venoms tested, the delayed administration of a single dose of the marimastat and varespladib combination resulted in prolonged survival for at least 17 hours after the venom-only controls suffered venom-induced lethality (FIG. 5). All animals receiving the delayed treatment survived for the full duration of the experiment (24 h) irrespective of the venom used as challenge, with the sole exception of one mouse receiving *E. carinatus* venom, for which survival was still prolonged by at least 18 h when compared with the venom-only control (death registered at 21.3 h) (FIG. 5B). These findings robustly demonstrate that the therapeutic combination of marimastat and varespladib provides broad preclinical efficacy against a diversity of medically important snake venoms, irrespective of variation in venom composition (i.e. the etiological toxins) found among those viper snake species.

6. Marimastat and DMPS Inhibit the In Vitro Metalloproteinase Activity of North American *Crotalus* Rattlesnake Venoms To explore whether the two metalloproteinase inhibiting drugs selected herein (i.e. marimastat and DMPS) would retain inhibitory potency against the venoms of medically important North American pit viper venoms, we used the previously described in vitro metalloproteinase assay (see Section 1) and venom from three rattlesnake species (*Crotalus* spp.). These species were selected for their clinical importance in the USA, namely: 1) *Crotalus atrox* (Western diamondback), which is found across the southwest USA and into Mexico and is thought to be the most common cause of snakebite envenoming in USA, 2) *Crotalus horridus* (Timber rattlesnake), which is found across Eastern and central USA, and is categorised as a Group I medically important snake by the World Health Organization. Furthermore, this species is not included in the immunising mixture of the current FDA-approved CroFab antivenom. 3) *Crotalus adamanteus* (Eastern diamondback), which is another Group I medically important snake, found in the South-East USA. We quantified the inhibitory potency of marimastat and DMPS against the metalloproteinase activity of each of these three venoms, and compared these with the inhibitory capabilities of MMPi5 and the FDA-approved antivenom CroFab.

Despite considerable venom variation among viper species from different regions of the world, and despite previously reported venom toxin variation between these three related species of North American rattlesnakes, our in vitro experiments demonstrated that both marimastat and DMPS effectively and potently inhibited metalloproteinase toxins from North American pit vipers (FIG. 6). Contrastingly, neither MMPi5 nor CroFab exhibited strong inhibition of either of the three venoms—no inhibitory effect against any of the venoms at the maximal dose tested (25 µg of antibodies) was observed with CroFab, while at the maximal drug concentrations tested (25 µM), MMPi5 only resulted in slight reduction in metalloproteinase activity across the three venoms (23.4-26.6% inhibition; FIG. 6). Both DMPS and marimastat (25 µM) potently reduced the metalloproteinase activity of each of the three venoms to near control levels in a comparable manner, with marimastat conferring 90.9-

99.1% inhibition of metalloproteinase activity across the three rattlesnake venoms, while DMPS conferred 88.6-97.8% inhibition (FIG. 6). These findings demonstrate that metalloproteinase inhibitors have variable potencies against snake venom metalloproteinases found in viper venoms, but provide confidence that both marimastat and DMPS are likely to be of therapeutic benefit against the venoms of medically important North American pit viper species.

7. The Therapeutic Combinations of Marimastat and Varespladib and DMPS and Varespladib Provide Potent Preclinical Efficacy Against Venoms from a Variety of North American Snake Species, and these Therapeutic Combinations Enhance the Preclinical Efficacy of Each Therapeutic Component To explore whether the two therapeutic drug combinations described herein (i.e. marimastat and varespladib, and DMPS and varespladib) are capable of delivering in vivo preclinical protection against the lethal effects of venoms sourced from medically important North American pit viper venoms, we used the previously described murine preincubation efficacy model (see Section 2) and venom from four North American pit viper species. These snake species were selected for their taxonomic diversity and clinical importance in the USA, namely: 1) *Crotalus atrox* (Western diamondback), which is found across the southwest USA and into Mexico and is thought to be the most common cause of snakebite envenoming in USA, 2) *Crotalus scutulatus* (Mojave rattlesnake), which is also found across the southwest USA and into Mexico, 3) *Sistrurus miliarius* (pygmy rattlesnake), which is found in the South-East USA, and 4) *Agkistrodon contortrix* (Eastern copperhead), which is found in central and eastern USA. As described above, we used a murine preincubation model of protection against venom lethality to assess the efficacy of test drugs, with each drug treatment coincubated with $2.5 \times LD_{50}$ dose of each venom followed by intravenous injection of the mixture into groups of five male CD-1 mice (18-20 g) via the tail vein followed by 6 hour monitoring. The drug treatments consisted of: DMPS, marimastat, or varespladib as solo drug treatments, or a DMPS and varespladib combination, or a marimastat and varespladib combination.

All five experimental animals receiving each of the four venoms rapidly succumbed to the lethal effects of envenoming (<10 mins for *C. atrox*, *S. miliarius* and *A. contortrix* venom, and <150 mins for *C. scutulatus* venom). As solo drug treatments, the metalloproteinase inhibiting drugs marimastat and DMPS provided some limited protection against envenoming by *C. scutulatus*, while marimastat additionally provided some protection against envenoming by *S. miliarius*, as measured by increased mean survival times (FIG. 7A). Neither drug provided protection against *C. atrox* or *A. contortrix* envenoming at the tested dose. Experimental animals treated with varespladib survived for longer periods of time than the venom only controls for each venom tested, however in only the group of animals challenged with *C. scutulatus* venom did the mice survive the duration of the experiment (FIG. 7A). While the two therapeutic drug combinations (DMPS+varespladib, and marimastat+varespladib) also provided complete preclinical protection against *C. scutulatus* venom lethality, both these drug combinations surpassed the preclinical efficacy conferred by any of the solo drug treatments for the remaining three venoms (FIG. 7B). The DMPS+varespladib combination also provided considerable protection against lethality caused by *S. miliarius* venom (80% survival of animals at end of experiment), and substantially delayed the onset of lethality caused by *C. atrox* and *A. contortrix* venoms (FIG. 7B). The marimastat+varespladib combination therapy provided complete protection against the lethal effects of *S. miliarius*, *A. contortrix* and *C. scutulatus* venoms, and substantially prolonged the survival times of animals challenged with *C. atrox* venom (FIG. 7B). These findings demonstrate that specific toxin inhibiting drugs have variable efficacy against the different venoms of North American pit viper species, but that the therapeutic drug combinations of marimastat+varespladib and DMPS+varespladib, provide superior and broad cross-species efficacy against the lethal envenoming effects caused by these variable snake species.

Conclusions

The work described herein demonstrates that the potency of previously ascribed Thetalloproteinase inhibitors' against snake venom metalloproteinases is unpredictable. In vitro inhibition experiments identified seven of the fifteen rationally selected drugs of potential interest, of which only two of these (marimastat and DMPS) conferred preclinical efficacy against the lethal effects of a venom rich in metalloproteinases. The combination of each of these rationally identified metalloproteinase-inhibiting drugs with the phospholipase inhibitor varespladib resulted in demonstrable evidence of enhanced preclinical efficacy against venom-induced lethality compared with a single drug alone. Moreover, combining these drugs results in broad preclinical efficacy against the lethal effects of envenoming caused by geographically-diverse and toxin variable, snake venoms. Thus, the two combination therapies identified here, namely DMPS+varespladib and marimastat+varespladib, offer considerable promise as completely novel therapeutic interventions for snakebite. Both of the metalloproteinase inhibiting components of the drug combinations identified herein exhibit high potency against North American pit viper (rattlesnake) venoms in vitro. Crucially, against representative North American pit viper species the two combination therapies identified here, namely DMPS+varespladib and marimastat+varespladib, exhibited broad cross-species efficacy against the lethal effects of envenoming, and both combination therapies conferred superior efficacy to each single drug component alone.

Study 2

A Therapeutic Combination of Two Small Molecule Toxin Inhibitors Provides Broad Preclinical Efficacy Against Viper Snakebite Abstract Snakebite is a medical emergency causing high mortality and morbidity in rural tropical communities that typically experience delayed access to unaffordable therapeutics. Viperid snakes are responsible for the majority of envenomings, but extensive interspecific variation in venom composition dictates that different antivenom treatments are used in different parts of the world, resulting in clinical and financial snakebite management challenges. Here, we show that a number of repurposed Phase 2-approved small molecules are capable of broadly neutralizing distinct viper venom bioactivities in vitro by inhibiting different enzymatic toxin families. Furthermore, using murine in vivo models of envenoming, we demonstrate that a single dose of a rationally selected dual inhibitor combination consisting of marimastat and varespladib prevents murine lethality caused by venom from the most medically-important vipers of Africa, South Asia and Central America. Our findings support the translation of combinations of repurposed small molecule-based toxin inhibitors as broad-spectrum therapeutics for snakebite.

Introduction

Snakebite is a Neglected Tropical Disease (NTD) that causes extensive mortality (138,000/annum) and morbidity (400,000/annum) in the impoverished rural communities of sub-Saharan Africa, South and Southeast Asia, Oceania, and Central and South America[1]. Despite annual snakebite deaths equating to one quarter of those that succumb to malaria[2], this NTD has long been overlooked by the global health community, resulting in little investment in snakebite management, the development of new therapeutics or improving speed of access to treatment. In 2017, snakebite was reclassified as a priority NTD by the World Health Organization (WHO) and, soon after, a global roadmap was published outlining the goal of halving snakebite-related deaths and disabilities by 2030[3]. Key tasks to achieve this goal include those relating to therapeutics, specifically the necessity to improve their safety, efficacy, affordability and accessibility to those in greatest need.

Snake venoms are complex mixtures of numerous proteins and peptides and extensive interspecific variation in venom composition poses major challenges for the development of generic (i.e. pancontinental) snakebite treatments[4,5]. Current therapies, known as antivenoms, consist of polyclonal immunoglobulins purified from the plasma/serum of large animals (e.g. equines, ovines) hyperimmunized with snake venoms. Because of the specificity of the resulting immunoglobulins towards the toxins present in the venoms used in manufacture, antivenoms typically have limited efficacy against envenoming by different snake species[6]. Consequently, distinct antivenom products are produced (>45 manufacturers worldwide) to treat envenoming by numerous snake species found in different parts of the world, resulting in a highly fragmented drug market, issues with affordability, and a lack of sustainability[7,8]. Other limitations with current antivenom include: (i) poor dose efficacy, as the majority (~80-90%) of their immunoglobulins do not bind venom toxins[1,9], (ii) high incidences of adverse reactions due to the administration of large doses of foreign immunoglobulins[10], (iii) the requirement for intravenous delivery in a healthcare facility, and (iv) reliance on cold chain transport and storage. In addition, many rural snakebite victims suffer major delays in accessing healthcare facilities following a bite, if they choose to attend at all, as evidenced by estimates suggesting that 75% of snakebite deaths occur outside of a hospital setting[11]. Cumulatively, these limitations identify an urgent and compelling need to develop cross-generically efficacious, stable and affordable, prehospital treatments as an effective means to considerably decrease snakebite mortality and morbidity[2,13].

Vipers represent a major group of medically important snakes that are widely distributed across the globe, ranging from the Americas to Africa and Asia, and are responsible for causing the majority of snake envenomings in these regions[14-16]. Treatments for systemic viper envenoming need to neutralize a number of major classes of hemotoxins, which are found in varying abundances across medically important snake species, and typically include the $Zn^{2+}$-dependent snake venom metalloproteinases (SVMPs), phospholipase $A_2$ (PLA$_2$s) and snake venom serine proteases (SVSPs)[17]. Collectively, these three enzymatic families typically comprise >60% of all toxins found in viper venom proteomes[5] and, in combination, are largely responsible for: (i) the destruction of local tissue, often resulting in necrosis, (ii) the degradation of the basement and cellular membranes resulting in extravasation, and (iii) the onset of coagulopathy via the activation and breakdown of clotting factors—with the latter two effects often culminating in life-threatening systemic hemorrhage[17-20].

Small molecule toxin inhibitors have received limited attention as potential alternatives to immunoglobulin-based snakebite therapies[12,21-25], although recent findings have suggested that a number of Phase-2 approved drugs may hold therapeutic promise[23,26-28]. Perhaps the most notable of these is the PLA$_2$-inhibitor, varespladib, which has been widely explored for repurposing as a snakebite therapy, and has shown substantial promise in preclinical models against a number of elapid and viper venoms[22,26,27,29]. In addition, several SVMP-inhibitors have been demonstrated to be capable of abolishing venom-induced hemorrhage or dermonecrosis, including metal ion chelators[21,24,25,28] and peptidomimetic hydroxamate inhibitors[23,24,30]. We recently reported that 2,3-dimercapto-1-propanesulfonic acid (DMPS), a $Zn^{2+}$ chelator that is a licensed oral medicine used to treat heavy metal poisoning, was particularly effective in preclinically neutralizing both the local and systemic toxicity of $Zn^{2+}$-dependent SVMP-rich saw-scaled viper venoms (genus *Echis*)[28]. However, despite the promise of both varespladib and DMPS as orally delivered prehospital therapeutics for snakebite, both are likely to be somewhat restricted in terms of their efficacy, as each predominately targets only one of the handful of major toxin families found in the venoms of medically important snakes.

To address this limitation, and cognisant of the complexity of snake venoms, herein we explored the potential of combinations of small molecule toxin inhibitors as new 'broad spectrum' snakebite therapeutics. Our goal—to rationally select and preclinically validate a therapeutic small molecule mixture capable of neutralizing distinct pathogenic toxins found in the venoms of geographically diverse, medically important, hemotoxic vipers—was achieved. Thus, we demonstrate, in a mouse model of envenoming, that a single dose of the SVMP-inhibitor marimastat, combined with the PLA$_2$-inhibitor varespladib, provides in vivo protection against the lethal effects of envenoming caused by the most medically important vipers of Africa, south Asia and Central America. Our findings suggest that combinations of small molecule toxin inhibitors are promising drug leads for the future development of generic prehospital therapies for treating hemotoxic snakebites.

Results

Venom SVMP activities are neutralized by peptidomimetic inhibitors and metal chelators SVMPs represent a major class of enzymatic toxins responsible for causing severe snakebite pathology, including hemorrhage, coagulopathy and tissue necrosis[17-19]. Two classes of SVMP-inhibitors have been historically investigated in the field of snakebite: metal chelators and peptidomimetic hydroxamate inhibitors[13]. These different molecules have distinct modes of action; chelators reduce the available pool of $Zn^{2+}$ required for SVMP bioactivity, while peptidomimetic hydroxamate inhibitors directly bind the $Zn^{2+}$ ion present in the catalytic core of the metalloproteinase[31]. Here, we compared the inhibitory capabilities of the peptidomimetic inhibitors marimastat and batimastat (both Phase 2-approved) and the chelators DMPS and dimercaprol (both licensed drugs) (FIG. 8) against a variety of venoms representing highly medically important viper species from distinct geographical regions[15,32-34] and with variable toxin compositions (FIG. 9); namely the West African and south Asian saw-scaled vipers (*Echis ocellatus* and *Echis carinatus*), the Central American fer-de-lance or terciopelo (*Both-*

*rops asper*), the African puff adder (*Bitis arietans*) and the south Asian Russell's viper (*Daboia russelii*).

We used an in vitro kinetic fluorogenic assay[28] to assess the SVMP bioactivity of each venom and its inhibition by varying concentrations of the four SVMP-inhibitors. All venoms exhibited considerable SVMP activity when compared to the PBS control (FIG. 10A), except for *D. russelii*, whose venom SVMP abundance was the lowest (6.9% of all venom proteins; FIG. 9) of the tested species. Marimastat displayed complete in vitro neutralization of SVMP bioactivity of the four active venoms across a 1000-fold drug concentration range (150 nM-150 µM) (FIG. 10B). Batimastat displayed equivalent efficacy to marimastat at the two lowest doses (1.5 µM and 150 nM, FIG. 10C), but could not be tested at the two higher concentrations due to the low water solubility of this drug and the interference of DMSO (>1%) in our assay. Conversely, dimercaprol was generally effective down to 1.5 µM ($IC_{50}$s=0.02-0.4 µM), and 15 µM of DMPS was required to fully inhibit SVMP activities ($IC_{50}$s=0.29-4.19 µM) (FIG. 10B). We therefore concluded that both peptidomimetic inhibitors are equally effective (with $IC_{50}$s<150 nM), and that both supersede the preclinically validated metal chelators[28] in neutralizing the in vitro SVMP activities of the African, Asian and American snake venoms tested here.

Procoagulant Venom Activities are Antagonized by Peptidomimetic Inhibitors and Metal Chelators Since SVMPs are key toxins associated with causing coagulopathy, we next investigated whether the same peptidomimetic and metal chelating inhibitors could also neutralize the procoagulant bioactivities of viper venoms. To do so, we used a validated kinetic absorbance-based assay monitoring plasma clotting[35] in the presence or absence of venoms and inhibitors (FIG. 11). Consistent with prior studies[38,37], all of the tested viper venoms displayed net procoagulant activity, with the exception of *B. arietans*, which had no effect on plasma clotting (FIG. 11A). While DMPS was effective at neutralizing the procoagulant activities of *E. ocellatus, E. carinatus* and *B. asper* venoms at the highest dose (150 µM) (FIG. 11B-D), it was ineffective against *D. russelii* (FIG. 11E). Dimercaprol outperformed DMPS in inhibiting procoagulant activity across all venoms ($IC_{50}$=<0.15-3.7 µM vs 0.8-25.91 µM, respectively), whereas the two peptidomimetic inhibitors were equivalent to (*Echis* spp.) or outperformed (*B. asper* and *D. russelii*) both chelators across the concentration range tested ($IC_{50}$=<0.15-1.92 µM for marimastat and <0.15 µM for batimastat). Notably, the complete neutralization of SVMP activity in *D. russelii* venom by high doses of marimastat and batimastat revealed clear venom anticoagulant effects (FIG. 11E), which is likely due to the lack of neutralization of anticoagulant venom components, such as $PLA_2$s[37].

The results of the SVMP and coagulation assays demonstrated that the peptidomimetic inhibitors outperformed the metal chelators and, although marimastat and batimastat are similar drugs in terms of both mechanism of action and in vitro efficacy, marimastat has a number of potential clinical advantages over batimastat, including: (i) increased solubility, (ii) excellent oral bioavailability vs. parenteral administration, and (iii) generally well tolerated vs. some reports of acute bowel toxicity[38]. Therefore, we selected marimastat as our candidate SVMP-inhibitor for use in in vivo venom-neutralization experiments.

Combinations of Inhibitors Inhibit Distinct Pro- and Anti-Coagulant Venom Toxins The coagulation assay findings described above for *D. russelii* provided a strong rationale for exploring combinations of small molecule toxin inhibitors as snakebite therapeutics. While the SVMP-inhibitors potently inhibited the dominant procoagulant activities of this venom, inhibition revealed a secondary, uninhibited, anticoagulant activity (FIG. 11E). To better understand these effects, we applied a validated nanofractionation approach[35,37] to *D. russelii* venom and reassessed the inhibition of pro- and anticoagulant bioactivities of the resulting venom fractions (FIG. 12A). Consistent with our findings using whole venom, the resulting nanofractionated bioactivity profiles displayed procoagulant peaks that were effectively inhibited in a dose-dependent manner by marimastat, while fractions with anticoagulant activity were not neutralized by this inhibitor at any of the tested concentrations (FIG. 12A).

Prior research suggests that the anticoagulant activity of *D. russelii* venom is mediated by $PLA_2$ toxins[37]. Indeed, of the toxins found in *D. russelii* venom, 35% are $PLA_2$s, while only 16% are SVSPs and 6.9% SVMPs[5] (FIG. 9). Consequently, we tested the well-established $PLA_2$-inhibitor varespladib (FIG. 8) against the same venom fractions. As anticipated, we found that varespladib effectively inhibited the anticoagulant activity of *D. russelii* venom (FIG. 12A) and, surprisingly, also exhibited some inhibitory effect against procoagulant venom toxins, but only at very high doses (20 µM), suggesting perhaps a non-specific effect (FIG. 12A).

Since marimastat effectively neutralizes the SVMP-driven procoagulant activity of *D. russelii* venom, while varespladib inhibits the anticoagulant $PLA_2$ toxins, we next tested whether a combination of these two drugs could restore normal clotting caused by the whole venom. At the two highest doses tested (15 µM and 150 µM), the combination of these two inhibitors restored clotting profiles to levels similar to those observed in the control (FIG. 12B), demonstrating that a rationally designed small molecule toxin inhibitor mix is capable of simultaneously inhibiting both procoagulant and anticoagulant venom toxins.

Venom SVSP Activities are Abrogated by the Serine Protease-Inhibitor Nafamostat

While inhibitors against SVMP and $PLA_2$ toxins have been actively researched, to our knowledge no serine protease-inhibitors have been investigated as drugs against snakebite. We selected nafamostat (FIG. 8), a serine protease-inhibitor licensed as an anticoagulant medicine in Japan[39], as a candidate SVSP-inhibitor and tested its in vitro efficacy using a chromogenic assay. Among the tested venoms, all except *D. russelii* displayed detectable SVSP activity in our assay (FIG. 13A). These activities were broadly neutralized in a dose-dependent manner by nafamostat (FIG. 13B), with the highest doses (150 and 15 µM) completely inhibiting SVSP activity, irrespective of venom ($IC_{50s}$=0.12-1.07 µM). Although SVSP toxins can also perturb coagulation, we were unable to test the efficacy of nafamostat in the plasma assay described above due to nafamostat's inherent anticoagulant potency (FIG. 14), which is mediated via interactions with cognate serine proteases found in the blood clotting cascade, such as thrombin and factors Xa and XIIa[40]. Because of these off-target interactions, generic SVSP-inhibitors must be carefully evaluated prior to any inclusion in a human snakebite therapy, especially since SVSPs are often less abundant in venom than SVMP or $PLA_2$ toxins[5]. Nevertheless, the in vitro efficacy of nafamostat demonstrated here justified its evaluation in in vivo models of envenoming to select the most efficacious mixture of inhibitors.

Preclinical Efficacy of Small Molecule Toxin Inhibitors as Solo and Combination Therapies We used an established in vivo model of envenoming[41,42] to test the efficacy of small molecule toxin inhibitors. This model consists of the preincubation of the test therapy with venom, followed by intravenous injection of the mixture into groups of five male CD-1 mice (18-20 g) via the tail vein, and is based on the gold standard method of preclinical efficacy recommended by the World Health Organization[43]. We first tested the ability of marimastat, varespladib and nafamostat as solo therapies to prevent venom-induced lethality in mice challenged with a 2.5×median lethal dose ($LD_{50}$) of E. ocellatus venom (45 µg)[25]. We selected this snake venom and venom dose as our initial model based upon its medical importance and results from our recent work exploring the preclinical venom-neutralizing efficacy of metal chelators[28]. All five of the experimental animals receiving only E. ocellatus venom succumbed to the lethal effects within 50 mins. Both the $PLA_2$-inhibitor varespladib and the SVMP-inhibitor marimastat (60 µg inhibitor/mouse) prolonged the survival of experimentally envenomed animals (FIG. 15A). However, marimastat conferred substantially greater protection than varespladib, as only one experimental animal succumbed towards the end of the experimental time frame of 6 h (death at 216 min), and the remaining four survived (FIG. 15A), while treatment with varespladib failed to prevent lethality over the full experimental time course, with two early deaths (5 and 9 min) and three later deaths (67, 210 and 341 min vs. <50 min for the venom-only control) observed (FIG. 15A). Conversely, the administration of the SVSP-inhibitor nafamostat (60 µg inhibitor/mouse) resulted in no evident efficacy, with negligible differences in survival times compared with the venom-only control (mean survival of 27.4 vs 17.8 min, respectively). Inhibitor-only controls revealed no obvious signs of acute toxicity of any of the drugs, as experimental animals survived without ill effects and exhibited normal behaviors throughout the 6 h treatment period.

We next tested the preclinical efficacy of two different inhibitor combinations against the lethal effects of E. ocellatus venom; (i) a dual mixture consisting of marimastat and varespladib (MV, 60 µg each) and (ii) a triple mixture containing marimastat, varespladib and nafamostat (MVN, 60 µg each). Both toxin inhibitor mixtures resulted in survival of all experimental animals until the end of the experiment (FIG. 15B), demonstrating that the combination of small molecules results in increases in efficacy, in line with our in vitro coagulation findings.

We next assessed markers of venom-induced coagulopathy in the envenomed animals via the quantification of thrombin-antithrombin (TAT) levels, a proxy for thrombin generation, in plasma collected following euthanasia. In line with previous reports[25,28], TAT levels correlated well with treatment efficacy. While animals in the venom-only group displayed very high TAT levels (mean of 1127.3 ng/ml), those receiving the MV and MVN inhibitor combinations exhibited substantially lower levels (162.0-203.9 and 238.1-255.5 ng/ml), and closer to those found in normal mice (i.e. no venom or treatment) controls (10.2-15.9 ng/ml) (FIG. 15C). TAT levels in the marimastat solo therapy group were also reduced (231.2-267.9 ng/ml) and comparable with the two combination therapies, but those detected in the less efficacious varespladib- and nafamostat-only treatment groups displayed substantially higher TAT levels (472.7-649.9 ng/ml and 543.9-859.1 ng/ml, respectively), although these remain lower than those of the venom-only controls. In combination, these findings suggest that marimastat is likely responsible for much of the observed efficacy against the lethal effects of E. ocellatus venom, but that small molecule combinations with additional toxin inhibitors provide superior preclinical efficacy than treatment with marimastat alone.

Inhibitor Mixes Protect Against Lethality Caused by a Diverse Range of Viper Venoms We next investigated whether the two inhibitor combination therapies were equally effective against the other viper venoms tested in vitro, as these venoms exhibit highly variable toxin compositions in comparison with the SVMP-rich toxin profile of E. ocellatus (FIG. 9). We adopted the same approach as described above, and intravenously challenged groups of experimental animals with $2.5 \times LD_{50}$ doses of E. carinatus (47.5 µg)[41], B. asper (47 µg)[44], B arietans (54 µg)[41] and D. russelii (20 µg)[45] venoms in the presence and absence of the MV and MVN therapeutic mixtures.

These results of these studies demonstrate the therapeutic potential of small molecule inhibitors, as despite extensive venom differences, we found that the dual mixture of marimastat and varespladib protected mice from the lethal effects of all four venoms for the duration of the experiment (FIG. 15D-G). The triple mixture, additionally containing nafamostat, proved equally effective across the venoms, with the exception of one early death (31 min) in the group dosed with D. russelii venom (FIG. 15D-G). TAT levels increased in all venom-only groups (FIG. 15H), although these increases were negligible in those receiving B. arietans venom—a finding in line with our in vitro data suggesting that this venom has little coagulopathic activity (FIG. 11A). TAT levels were consistently reduced in the experimental animals treated with the two inhibitor mixtures, resulting in 53.6-95.5% reductions compared with the various venom-only groups (FIG. 15H).

Comparable preclinical efficacy between the MV and MVN inhibitor combinations against a variety of medically important viper venoms suggests that the SVSP-inhibitor nafamostat does not contribute substantially to venom neutralization. Because (i) SVSP-inhibitors such as nafamostat can induce off-target effects by interacting with serine proteases found in the coagulation cascade, (ii) the inclusion of every additional molecule in an inhibitory therapeutic combination substantially increases regulatory hurdles for future translation, and (iii) the inhibition of SVMP and $PLA_2$ toxins appears sufficient to protect against lethality caused by a diverse array of viper venoms, we decided to proceed with the marimastat and varespladib combination as our lead candidate for testing in more therapeutically challenging preclinical models of envenoming.

Administration of the Marimastat and Varespladib (MV) Dual Therapy after Venom Challenge Broadly Protects Against Venom Lethality To better mimic a real-life envenoming scenario, we next tested the marimastat and varespladib inhibitor mixture in a preclinical 'challenge then treat' model of envenoming, where the venom is first administered intraperitoneally and then the test therapy is administered intraperitoneally separately after the venom challenge[28]. To this end, we injected venom from each of the five viper species in doses equivalent to at least 5×the intravenous (iv) $LD_{50}$ dose followed, 15 mins later, by a single dose of the inhibitor mixture (120 µg of both marimastat and varespladib). Experimental animals were then monitored for 24 h. For E. ocellatus, E. carinatus and B. arietans venoms we challenged mice with 5×iv. $LD_{50}$ doses (90 µg, 95 µg and 108 µg, respectively), while higher venom doses were required for B. asper (303 µg, equivalent to ~16×iv $LD_{50}$ or 3×ip $LD_{50}$[46]) and D. russelii (13×iv $LD_{50}$, 105 µg) to ensure mortality occurred within 7 h, thus leaving a 17 h window for measuring prolonged survival in the treatment groups.

All of the venom-only groups succumbed to the lethal effects of envenoming within 4 h, with the exception of two mice receiving *D. russelii* venom (deaths at ~7 h), while experimental animals dosed with only the inhibitor combination (i.e. treatment control) survived the duration of the experiment (24 h) with no apparent adverse effects (FIG. 16A-E). Across all of the diverse venoms tested, the delayed administration of a single dose of the marimastat and varespladib combination resulted in prolonged survival for at least 17 h after the venom-only controls suffered venom-induced lethality (FIG. 16A-E). All animals receiving the delayed treatment survived for the full duration of the experiment (24 h) irrespective of the venom used as challenge, with the sole exception of one mouse receiving *E. carinatus* venom, for which survival was still prolonged by at least 18 h when compared with the venom-only control (death registered at 21.3 h) (FIG. 16B).

Quantified TAT levels from the envenomed animals correlated with survival, with those receiving the inhibitor mixture exhibiting 78.5-90.5% reductions compared to the elevated levels of the various venom-only controls (FIG. 16F). Contrastingly, quantification of soluble thrombomodulin, a marker of endothelial cell damage, was only elevated in *B. asper* 'envenomed' mice. This observation was noted for both the 'intravenous preincubation' and 'intraperitoneal challenge then treat' models of envenoming (FIGS. 17A and B), and these elevated levels were reduced to control levels in experimental animals treated with the inhibitor combination in both experimental approaches (FIG. 17C). These findings suggest that, in addition to protecting against the lethal effects of the various viper venoms, the marimastat and varespladib therapeutic combination is capable of preventing coagulopathy, and in the case of *B. asper*, inhibiting toxins acting to disrupt certain components of the endothelium.

Discussion

Snakebite is the world's most lethal NTD, resulting in ~138,000 deaths annually and primarily affecting the world's resource-poor populations of the tropics and subtropics[1]. Although conventional polyclonal immunoglobulin-based antivenoms save thousands of lives each year, their lack of specificity, poor cross-species efficacy, reliance on delivery in clinical settings and low affordability severely hamper their accessibility and utility for treating tropical snakebite victims[1,42]. Consequently, new strategies capable of circumventing variation in snake venom composition to deliver broad neutralization across snake species, while simultaneously improving the safety, affordability and storage logistics of treatment, are urgently needed[3,47]. Approaches showing signs of promise include the rational design of immunogens to improve the neutralizing breadth of conventional products[48], the selection of human or humanized toxin-specific monoclonal or oligoclonal antibodies[49,50], and the use of small molecule inhibitors specific to certain toxin families[12], such as the PLA$_2$-inhibitor varespladib[22,26,27] and the metal chelator DMPS[28]. Small molecule toxin inhibitors offer a number of desirable characteristics over existing snakebite therapies, including desirable specificity, potent dose-efficacy, higher tolerability, greater stability and superior affordability[12]. These characteristics, combined with their oral formulation, provide an opportunity to explore their utility as prehospital treatments for snakebite, thereby circumventing one of the major challenges faced by impoverished snakebite victims, who have great difficulty in rapidly accessing the secondary and tertiary healthcare facilities where current treatments are held. Here, we show that a small molecule mixture consisting of the inhibitors marimastat and varespladib, which are directed against the hemotoxicity-inducing SVMP and PLA$_2$ toxin families, provides preclinical protection against lethality caused by a geographically diverse array of medically important viper venoms that differ considerably in their toxin compositions.

Due to their importance in many snake venoms, we first rationally selected an inhibitory molecule capable of abrogating the activity of SVMP toxins. In vitro SVMP and coagulation assays convincingly demonstrated that the Phase 2-approved peptidomimetic hydroxamate inhibitors batimastat and marimastat provided superior venom neutralization over the metal chelators DMPS and dimercaprol (FIGS. 10 and 11). Despite previous reports of batimastat exhibiting increased efficacy over marimastat in preventing venom-induced local hemorrhage[23], we found both drugs to be equipotent in vitro. We selected marimastat as our candidate for in vivo efficacy experiments due to a number of desirable characteristics that make it amenable for a future field intervention for snakebite, specifically its oral vs. intraperitoneal route of administration, and its increased solubility and tolerability compared to batimastat[38]. Indeed, these characteristics seemingly contributed to the demise of batimastat during development, although both drugs were ultimately discontinued following lack of efficacy in Phase 3 clinical trials[38], despite showing early promise as cancer therapeutics[51]. Marimastat displays particularly good oral bioavailability. It can be detected in the blood of patients within 15-60 min after ingestion, reaches peak plasma concentrations 1.5-3 h post-administration with a half-life of 8-10 h[52], and can be detected in the circulation when given at doses >200 mg for up to 2 days[52]. Furthermore, marimastat is well tolerated, with no notable side effects observed with single doses of up to 800 mg or bidaily doses of 200 mg for 6.5 days[52], or when 75 mg doses were administered daily for 28 days in patients with advanced pancreatic cancer[53]. In our study, we used a low dose of 3 µg/g or 6 µg/g for the intravenous and intraperitoneal murine models of envenoming respectively, which translates to 0.24 mg/kg and 0.48 mg/kg when applying a facile mouse to human dose conversion[54]. Even when considering the differences in route of administration (intravenous/intraperitoneal vs. oral), our extrapolated dose (33.6 mg per 70 kg adult) is very low compared to that well-tolerated in Phase 1 trials (800 mg) and this, combined with the relatively high oral bioavailability of marimastat (70%), offers substantial scope for the development of this drug as a prehospital therapeutic for use soon after a snakebite. However, murine bridging studies incorporating pharmacokinetic (PK) profiling coupled with pharmacodynamic (PD) assessments of venom neutralization are required in the future to enable accurate simulations of predicted human doses.

The second drug in our mixture, varespladib, is a secretory PLA$_2$-inhibitor previously investigated for use in the treatment of various acute coronary syndromes[55]. Both varespladib and varespladib methyl (its oral prodrug, which is rapidly converted in vivo to varespladib) have been used clinically in Phase 1 and 2 trials[55-57], although a lack of efficacy at Phase 3 ultimately resulted in discontinuation[58]. More recently, varespladib has been explored for repurposing as a potential therapeutic for the treatment of snakebite. Both varespladib and its oral prodrug have been shown to exhibit promising neutralizing capabilities against a variety of different snake venoms[22,29], but have proven to be particularly effective at mitigating the life-threatening effects of neurotoxicity caused by certain elapid venoms in animal models of envenoming[26,27,59]. Similar to marimastat, varespladib shows good oral bioavailability, and has a half-life equating to 5 hr when delivered by iv infusion[55]. Varespladib has also been demonstrated to be well tolerated at Phase 1 and 2[55], although a double-blind randomized Phase 3 clinical trial showed that acute coronary syndrome patients receiving 500 mg of oral varesapldib daily had a greater risk of myocardial infarction than those receiving placebo[58], despite the same daily dose used in Phase 2B (>300 patients for >6 months) resulting in no greater risk of major adverse cardiovascular events[56]. Given that the dose of varespladib used in these clinical studies is ~15-fold higher than the facilely-extrapolated human equivalent dose used intraperitoneally in our animal model (0.48 mg/kg, 33.6 mg per 70 kg adult)[54], there appears to be considerable space to safely optimize the dose and dosing frequency of varespladib to establish an appropriate therapeutic regimen for use for treating snakebite, though murine bridging study-based simulations of appropriate human doses are needed.

Our in vivo venom neutralization studies demonstrate that a combination of these SVMP- and PLA$_2$-inhibiting drugs is capable of counteracting the lethal hemorrhagic, coagulopathic and/or hemostasis-disrupting effects of a variety of venoms sourced from the most medically important vipers of Central America, sub-Saharan African and South Asia[15,32-34] (FIGS. 15 and 16). The addition of the serine protease-inhibitor nafamostat to the therapeutic mixture resulted in no additional protection to the marimastat and varespladib dual combination (FIG. 15) despite SVSP toxins also being common pathogenic constituents of many viper venoms[5], and this drug exhibiting potent inhibition of SVSP toxins in vitro (FIG. 13). These findings, alongside evidence that nafamostat provides no protection against the lethal effects of E. ocellatus venom when used as a solo therapy (FIG. 15A), suggest that nafamostat does not appear to substantially contribute to the preclinical efficacy observed (FIG. 15). Despite being a licensed anticoagulant drug in Japan since the early 1990s[39], nafamostat has potential detrimental off-target effects for use in snake envenoming via interaction with cognate coagulation cascade serine proteases[40], has a short half-life (~8 min)[60], and requires intravenous administration, thereby limiting its utility and applicability as a potential prehospital snakebite therapeutic. For those various reasons, our lead candidate therapeutic mixture remained restricted to the marimastat and varespladib combination.

The administration of the marimastat and varespladib combination 15 mins after 'envenoming' resulted in the survival of experimental animals for at least 17 h after mortality was observed in the venom-only control groups (FIG. 16). In our previous work, we demonstrated that the licensed metal chelator DMPS, which shows much promise as an early intervention therapeutic against snakes with SVMP-rich venoms (e.g. the West African saw-scaled viper, E. ocellatus)[28], prevented lethality for ~8 h in the same preclinical model, but required a later dose of antivenom (1 hr after venom delivery) to extend protection to a comparable duration to that observed here with the marimastat and varespladib combination (FIG. 18). While DMPS remains a promising future therapeutic for snakebite, not least because of its oral formulation, licensed drug status and decades of therapeutic use for other indications[61,62], it seems unlikely to be highly efficacious as a solo therapy against a wide variety of different snake species due to only targeting SVMP toxins[28]. Contrastingly, the combination of marimastat and varespladib reported here provided consistent and prolonged preclinical protection against lethality caused by a wide diversity of medically important vipers despite, for example, the south Asian Russell's viper (D. russelii) having substantially different abundances of distinct venom toxins to that of E. ocellatus[4,63-65] (FIG. 9). Given that all existing antivenoms are geographically-restricted in terms of their snake species efficacy (e.g. restricted to specific continents or countries within), and require considerably higher doses to be preclinically effective (e.g. 166.66 μg of monospecific antivenom antibodies[25] vs 1.33 μg of each inhibitor per 1 μg of venom challenge for E. ocellatus, for example), these findings suggest that this therapeutic combination of small molecule toxin inhibitors may represent a highly specific yet generic future treatment for viperid snakebite.

Notwithstanding the apparent therapeutic promise of this small molecule toxin inhibitor combination, a considerable amount of future research is required to facilitate its translation. Despite the combination of animal models used here providing confidence of broad anti-envenoming efficacy, these models remain limited in terms of accurately recapitulating cases of human envenoming (e.g. in terms of venom dose, route of venom delivery, treatment duration, etc). Thus, additional preclinical studies are needed to further explore the neutralizing efficacy of this drug combination, including the use of oral dosing regimens, and repeat dosing experiments combined with pharmacokinetic analyses, to effectively model the oral dose required to maintain effective concentrations of the drugs sufficient to provide prolonged protection from envenoming. This may be particularly challenging for cases where envenoming may result in prolonged treatment times, for example as the result of recurrence of coagulopathy or acute kidney injury, and thus additional model development addressing this point is needed. While no overt adverse reactions were observed in the experimental animals used in this study, and both marimastat and varespladib have previously been demonstrated to be well tolerated clinically[52,53,57,66], potential drug-drug interactions at PK/PD-informed human doses also need to be robustly assessed. The in vitro and in vivo venom neutralization data presented here should also be extended to additional medically important snake species, and the efficacy of this combination therapy against the local, morbidity-inducing, effects of snake venoms should be explored. Finally, the successful delivery and uptake of any prehospital snakebite treatment comes with a number of long-term implementation challenges that require careful consideration, including ensuring (i) acceptable safety profiles across the target population (e.g. both children and adults) and (ii) that health seeking behavior after initial treatment is strongly promoted so that patients are carefully monitored in case additional (i.e. doses) or complementary (i.e. antivenom) treatment is required.

Despite these remaining challenges, we demonstrated here that a combination of two Phase 2-approved drugs, marimastat and varespladib, provides broad protection against venom-induced lethality in both a conventional 'preincubation' model of envenoming, and a far more challenging preclinical model consisting of delayed drug delivery post-envenoming. While these findings hold much promise, we propose that the future translation of this inhibitor combination should occur in parallel with other small molecule toxin inhibitor lead candidates, such as DMPS and varespladib[26-28,59], to increase the breadth of new molecules being added to the snakebite treatment toolbox and, most importantly, to help offset the risk of potential drug failures during clinical trials. Ultimately, our data provides the first empirical evidence that combinations of small molecule toxin inhibitors can provide cross-species neutralization of medically important snake venoms, and thus advocates for the future translation of such combinations as generic, prehospital treatments to reduce the life-threatening and life-changing consequences of the world's most lethal neglected tropical disease—snakebite.

Methods

Venoms

Venoms were sourced from either wild-caught specimens maintained in, or historical venom samples stored in, the Herpetarium of the Liverpool School of Tropical Medicine. This facility and its protocols for the expert husbandry of snakes are approved and inspected by the UK Home Office and the LSTM and University of Liverpool Animal Welfare and Ethical Review Boards. The venom pools were from vipers with diverse geographical localities, namely: *E. ocellatus* (Nigeria), *E. carinatus sochureki* (India, referred to throughout as *E. carinatus*), *B. arietans* (Nigeria), *B. asper* (Atlantic coast of Costa Rica) and *D. russelii* (Sri Lanka). Note that the Indian *E. carinatus* venom was collected from a single specimen that was inadvertently imported to the UK via a boat shipment of stone, and then rehoused at LSTM on the request of the UK Royal Society for the Prevention of Cruelty to Animals (RSPCA). Crude venoms were lyophilized and stored at 4° C. to ensure long term stability. Prior to use, venoms were resuspended to 10 mg/ml in PBS (pH 7.4) and then further diluted to 1 mg/ml stock solutions (with PBS) for the described experiments.

Inhibitors

Dimercaprol (2,3-dimercapto-1-propanol 98% iodometric, Cat no: 64046-10 ml), marimastat (≥98% HPLC M2699-5MG), batimastat (SML0041-5MG) and varespladib (≥98% HPLC SML1100-5MG) were purchased from Sigma-Aldrich. Nafamostat mesylate (ab141432 10 mg) was purchased from Abcam and DMPS (2,3-dimercapto-1-propanesulfonic acid sodium salt monohydrate, 95%, Cat no: H56578) from Alfa Aesar. Working stocks (tenfold dilutions from 2 mM to 2 μM) were made using deionized water, with the exception of varespladib and batimastat, for which we used DMSO due to water insolubility.

Enzymatic Assays

The SVMP assay measuring metalloproteinase activity and the plasma assay measuring coagulation in the presence or absence of venoms and inhibitors were performed as previously described[28]. The SVMP assay kinetically measured cleavage of a quenched fluorogenic substrate (ES010, R&D Biosystems) by venom in the presence or absence of inhibitors.

Briefly, 10 μl of the substrate (supplied as a 6.2 mM stock) was used per 5 ml reaction buffer (150 mM NaCl, 50 mM Tris-CI pH 7.5). Reactions consisted of 10 μl of venom±inhibitors in PBS and 90 μl of substrate. Venoms were used at 1 μg/reaction and final inhibitor concentrations ranged from 150 μM to 150 nM. Samples were preincubated for 30 min at 37° C. and pipetted in triplicate into 384-well plates (Greiner). Thereafter, data was collected on an Omega FLUOstar (BMG Labtech) instrument at an excitation wavelength of 320 nm and emission wavelength of 405 nm at 25° C. for 1 h. The areas under the curve (AUCs) in the 0-40 min interval were calculated for each sample using MARS data analysis software v3.31 (BMG Labtech); this time point was chosen as the time where all fluorescence curves had reached a plateau (maximum fluorescence). For comparing venom-only samples, the means of at least three independent experimental runs for each condition, expressed as AUCs (n≥3), were plotted at each inhibitor concentration with standard error of the mean (SEM). To determine inhibitor efficacy, the AUCs for each of the samples that consisted of venom+inhibitors were transformed and expressed as percentages of the venom-only sample (where the venom was 100%). The negative control (PBS only) was also expressed relative to the venom, and the variation in background was presented as an interval delineated by the lowest and highest values in the PBS-only samples across concentrations and inhibitors for a specific venom. Due to the sensitivity of the assay to DMSO concentrations above 1% in the final reaction, the 2 mM stock of batimastat was further diluted in reaction buffer to obtain 200 μM, 20 μM and 2 μM stocks, alongside appropriate DMSO only controls. However, only the latter two concentrations were sufficiently depleted of DMSO for viable use in the assay.

We used a previously developed plasma clotting assay[35] to measure venom-induced coagulation. Briefly, 100 ng of each venom was incubated at 37° C. for 30 min in the presence or absence of inhibitors (150 μM to 150 nM final concentrations). The final reaction consisted of 10 μl venom±inhibitors in PBS, 20 μl 20 mM $CaCl_2$), and 20 μl citrated bovine plasma (VWR). The samples were pipetted in triplicate into 384-well plates, and absorbance monitored at 595 nm for 2 h at 25° C. on an Omega FLUOstar instrument. We calculated the maximum clotting velocity of each of the curves as per clot waveform analysis[67], by calculating the maximum of the first derivative. The means of at least three independent experimental runs for each condition were plotted at each inhibitor concentration with SEMs.

SVSP activity was measured using a chromogenic substrate (S-2288, Cambridge Bioscience). Reactions consisted of 15 μl of venom±inhibitors in PBS, 15 μl of assay buffer (100 mM Tris-CI pH 8.5, 100 mM NaCl) and 15 μl of 6 mM substrate. A positive venom-only control, a negative control containing 15 μl of PBS and a drug-only control (where applicable) were also included. The final substrate concentration was 2 mM and venoms were used at 1 μg/reaction. When testing inhibitors, these were preincubated with the venoms for 30 min at 37° C. with concentrations ranging from 150 μM to 150 nM (tenfold dilutions). The samples were pipetted in triplicate into 384-well plates (Greiner) and absorbance at 405 nm was monitored kinetically for ~30 min on an Omega FLUOstar instrument (BMG Labtech). Given the linearity of the resulting slopes, negative control readings (PBS) were subtracted from each reading and the rate of substrate consumption calculated by measuring the slope between 0 and 5 mins. The mean rates (expressed as ΔAbs/time/μg venom) of at least three independent experimental runs for each condition (n 3) were plotted at each inhibitor concentration with SEMs using Prism v8 software (GraphPad).

Nano Fractionation Experiments

Fifty microlitres of venom solution (*D. russelii;* 1 mg/ml) was injected into a Shimadzu LC-2010 system with nanofractionation in parallel. Separation was performed on a Waters XBridge reversed-phase C18 column (250×4.6 mm column with 3.5 μm pore-size) at 30° C. The total flow rate of the mobile phase solution was 0.5 ml/min with eluent A (98% $H_2O$, 2% acetonitrile [ACN], 0.1% formic acid [FA]) and eluent B (98% ACN, 2% $H_2O$, 0.1% FA). Liquid chromatography gradients consisted of a linear increase of mobile phase B from 0 to 50% in 20 min, followed by a linear increase to 90% B in 4 min, then isocratic at 90% B for 5 min, after which the percentage of mobile phase B was decreased from 90% to 0% in 1 min, followed by 10 min at 0% B to re-equilibrate. The effluent was split in a 1:9 ratio of which the 10% fraction was sent to a Shimadzu SPD-M20A prominence diode array detector and the 90% fraction was directed to a nanofractionation collector which dispensed the fractions into transparent 384-well plates (F-bottom, rounded square well, polystyrene, without lid, clear, non-sterile; Greiner Bio One, Alphen aan den Rijn, The Netherlands) at a resolution of 6 s/well. The collector used was either a commercially available FractioMate™ nanofractionator (SPARK-Holland & VU, Netherlands, Emmen & Amsterdam) controlled by FractioMator software v1.0 (Spark-Holland, The Netherlands, Emmen) or a modified Gilson 235P autosampler controlled by in-house written software Ariadne v1.8 (VU Amsterdam). The well plates with venom fractions were then dried overnight in a Christ Rotational Vacuum Concentrator (RVC 2-33 CD plus, Zalm en Kipp, Breukelen, The Netherlands) equipped with a cooling trap, and maintained at −80° C. during operation. The freeze-dried plates were then stored at −80° C. prior to bioassaying.

Neutralization of coagulopathic venom toxins by marimastat and varespladib was assessed by assaying the *D. russelii* venom nanofractionated plates in the plasma coagulation assay, as recently described[35]. To each well of the nanofractionated well plate, 10 µl of inhibitor solution (e.g. marimastat or varespladib in PBS, or PBS-only control) was pipetted by a VWR Multichannel Electronic Pipet, followed by brief low-speed collection of samples via centrifugation at 805×g. The final assay concentrations of the inhibitors tested in the assay were 20 µM, 4 µM, 0.8 µM, 0.16 µM, 0.032 µM and 0.0064 µM. The plates were then incubated for 30 min at room temperature, and during this time bovine plasma (Sterile Filtered, Biowest, Nuaille, France) was defrosted in a water bath and centrifuged for 4 min at 805×g prior to use. Following incubation, 20 µl $CaCl_2$) solution (20 mM), followed by 20 µl plasma (with instrument rinsing in between with Milli-Q water), were pipetted into each well on the plate using a Multidrop™ 384 Reagent Dispenser (Thermo Fisher Scientific, Ermelo, The Netherlands). The plate was then read immediately for absorbance kinetically for 100 min at 595 nm at 25° C. using a Varioskan™ Flash Multimode Reader (Thermo Fisher Scientific, Ermelo, The Netherlands). The obtained results were normalized by dividing the slope measured in each well by the median of all slope values across the plate, and the processed coagulation chromatograms were plotted to visualize very fast coagulation, medium increased coagulation and anticoagulation, as previously described[37].

In Vivo Experimentation

All animal experiments were conducted using protocols approved by the Animal Welfare and Ethical Review Boards of the Liverpool School of Tropical Medicine and the University of Liverpool, and performed in specific pathogen-free conditions under licensed approval (PPL #4003718 and #P5846F90) of the UK Home Office and in accordance with the Animal [Scientific Procedures] Act 1986 and institutional guidance on animal care. All experimental animals (18-20 g [4-5 weeks old], male, CD-1 mice, Charles River, UK) were housed in groups of five with environmental enrichment, water and food ad libitum and their health monitored daily during acclimatization. The experimental design was based upon 3R-refined WHO-recommended protocols[28,41], with animals randomized and observers being blinded to the experimental condition. The median lethal doses (venom $LD_{50}$) used for *E. ocellatus* (Nigeria), *E. carinatus* (India), *B. asper* (Costa Rica), *D. russelii* (Sri Lanka) and *B. arietans* (Nigeria) venoms were previously determined[25,41,44,45].

Preclinical Efficacy Via a Preincubation Model of Envenoming

For our initial in vivo experiments, we used 2.5×the intravenous $LD_{50}$ doses of *E. ocellatus* (45 µg), *E. carinatus* (47.5 µg), *B. asper* (47 µg), *D. russelii* (20 µg) and *B. arietans* (54 µg) venoms in a 3R-refined version of the WHO-recommended[41] antivenom $ED_{50}$ neutralization experiment[25]. Groups of five mice received experimental doses that consisted of either: (a) venom only (2.5×$LD_{50}$ dose); (b) venom and solo drug (60 µg); (c) solo drug only (60 µg); (d) venom and a mix of two or three drugs (60 µg each); or (e) a mix of two or three drugs only (60 µg each). Drugs were dissolved in water, with the exception of varespladib, which was prepared as a 5 mg/ml stock in DMSO (2.5% in the final reaction) due to solubility. All experimental doses were prepared to a volume of 200 µl in PBS and incubated at 37° C. for 30 mins prior to their intravenous injection via the tail vein. Animals were monitored for 6 h, and euthanized via rising concentrations of $CO_2$ upon observation of previously defined humane endpoints that are predicators of lethality (e.g. seizure, pulmonary distress, paralysis, hemorrhage)[28]. Deaths, time of death, and survivors were recorded; where death/time of death actually represents the implementation of euthanasia based on defined humane endpoints.

Preclinical Efficacy Via a 'Challenge then Treat' Model of Envenoming

In these experiments, mice were challenged with venom intraperitoneally followed by delayed dosing of the marimastat and varespladib inhibitor mix 15 mins later, as previously described[28]. For *E. ocellatus, E. carinatus* and *B. arietans* venoms we challenged mice with 5×iv $LD_{50}$ doses (90 µg, 95 µg and 108 µg, respectively), while higher doses were required to cause lethality with *B. asper* (303 µg, ~16×iv. $LD_{50}$s) and *D. russelii* (13×iv. $LD_{50}$, 105 µg) venoms in this model. All intraperitoneal venom doses consisted a final volume of 100 µl in PBS. Drug doses were scaled up from 60 µg/mouse in the preincubation experiments outlined above to 120 µg/mouse here, in line with the (at least) doubling of the venom challenge dose from 2.5× $LD_{50}$ to 5×$LD_{50}$ (i.e. for *E. ocellatus, E. carinatus* and *B. arietans*). All inhibitor doses were delivered intraperitoneally 15 mins after venom injection and consisted of 200 µl final volumes. The experimental groups comprised five mice receiving: (a) venom only+200 µl PBS (15 min later); (b) venom+drug mix (120 µg marimastat and 120 µg varespladib, 15 min later); and (c) sham (100 µl PBS)+drug mix (15 min later). Experimental animals were monitored for 24 h, with humane end points for euthanasia, and data recording, performed as described above.

Quantification of Thrombin-Antithrombin Levels and Thrombomodulin Levels by ELISA For all experimental animals described above, blood samples were collected via cardiac puncture immediately post-euthanasia. Plasma was separated by centrifugation at 400×g for 10 min and stored at −80° C. We assessed the levels of thrombin-antithrombin complexes (TAT) and soluble thrombomodulin using mouse ELISA Kits (ab137994 and ab209880, Abcam), following the manufacturer's protocol. All available plasma samples (some were unobtainable via cardiac puncture due to extensive internal hemorrhage) were assessed if the time of death within the group varied, whereas three samples were randomly chosen if the time of death was the same (e.g. either very rapid death within 2 minutes, or survival until the end of the experiment [360 min or 24 h]). The resulting data was plotted as the median of duplicate measurements for each animal and is presented with standard deviations (SDs).

Data Availability

There are no restrictions on data availability. Data used to construct the species distributions displayed in FIG. 9 are freely available on the World Health Organization Venomous Snake Distribution database: https://apps.who.int/bloodproducts/snakeantivenoms/database/) and the IUCN Red List of Threatened Species database: (https://www.iucnredist.org/).

REFERENCES

1. Gutiérrez, J. M. et al. Snakebite envenoming. *Nat. Rev. Dis. Prim.* 3, 17063 (2017).
2. Harrison, R. A., Casewell, N. R., Ainsworth, S. A. & Lalloo, D. G. The time is now: a call for action to translate recent momentum on tackling tropical snakebite into sustained benefit for victims. *Trans. R. Soc. Trop. Med. Hyg.* 113, 835-838 (2019).
3. Williams, D. J. et al. Strategy for a globally coordinated response to a priority neglected tropical disease: Snakebite envenoming. *PLoS Negl. Trop. Dis.* 13, e0007059 (2019).
4. Casewell, N. R. et al. Medically important differences in snake venom composition are dictated by distinct postgenomic mechanisms. *Proc. Natl. Acad. Sci. U.S.A.* 111, 9205-10 (2014).
5. Tasoulis, T. & Isbister, G. K. A review and database of snake venom proteomes. *Toxins* (Basel). 9, 290 (2017).
6. Williams, D. J. et al. Ending the drought: New strategies for improving the flow of affordable, effective antivenoms in Asia and Africa. *J. Proteomics* 74, 1735-1767 (2011).
7. Arnold, C. Vipers, mambas and taipans: the escalating health crisis over snakebites. *Nature* 537, 26-28 (2016).
8. Gutiérrez, J. M. Global availability of antivenoms: The relevance of public manufacturing laboratories. *Toxins* 11, 5 (2019).
9. Casewell, N. R. et al. Pre-clinical assays predict pan-African *Echis* viper efficacy for a species-specific antivenom. *PLoS Negl. Trop. Dis.* 4, e851 (2010).
10. de Silva, H. A. et al. Low-dose adrenaline, promethazine, and hydrocortisone in the prevention of acute adverse reactions to antivenom following snakebite: A randomised, double-blind, placebo-controlled trial. *PLoS Med.* 8, e1000435 (2011).
11. Mohapatra, B. et al. Snakebite mortality in India: a nationally representative mortality survey. *PLoS Negl. Trop. Dis.* 5, e1018 (2011).
12. Bulfone, T. C., Samuel, S. P., Bickler, P. E. & Lewin, M. R. Developing small molecule therapeutics for the initial and adjunctive treatment of snakebite. *J. Trop. Med.* 2018, 1-14 (2018).
13. Knudsen, C. & Laustsen, A. H. Recent advances in next generation snakebite antivenoms. *Trop. Med. Infect. Dis.* 3, 42 (2018).
14. Habib, A. G., Gebi, U. I. & Onyemelukwe, G. C. Snake bite in Nigeria. *Afr. J. Med. & Med. Sci.* 30, 171-178 (2001).
15. Otero-Patiño, R. Epidemiological, clinical and therapeutic aspects of *Bothrops asper* bites. *Toxicon* 54, 998-1011 (2009).
16. Kumar, K. G. S., Narayanan, S., Udayabhaskaran, V. & Thulaseedharan, N. K. Clinical and epidemiologic profile and predictors of outcome of poisonous snake bites—an analysis of 1,500 cases from a tertiary care center in Malabar, North Kerala, India. *Int. J. Gen. Med.* 11, 209-216 (2018).
17. Slagboom, J., Kool, J., Harrison, R. A. & Casewell, N. R. Haemotoxic snake venoms: their functional activity, impact on snakebite victims and pharmaceutical promise. *Br. J. Haematol.* 177, 947-959 (2017).
18. Gutiérrez, J. M. & Rucavado, A. Snake venom metalloproteinases: their role in the pathogenesis of local tissue damage. *Biochimie* 82, 841-850 (2000).
19. Gutiérrez, J. M., Escalante, T., Rucavado, A. & Herrera, C. Hemorrhage caused by snake venom metalloproteinases: a journey of discovery and understanding. *Toxins* (Basel). 8, 93 (2016).
20. Ferraz, C. R. et al. Multifunctional toxins in snake venoms and therapeutic implications: from pain to hemorrhage and necrosis. *Front. Ecol. Evol.* 7, 1-19 (2019).
21. Howes, J.-M., Theakston, R. D. G. & Laing, G. D. Neutralization of the haemorrhagic activities of viperine snake venoms and venom metalloproteinases using synthetic peptide inhibitors and chelators. *Toxicon* 49, 734-739 (2007).
22. Lewin, M., Samuel, S., Merkel, J. & Bickler, P. Varespladib (LY315920) appears to be a potent, broad-spectrum, inhibitor of snake venom phospholipase A2 and a possible pre-referral treatment for envenomation. *Toxins* (Basel). 8, 248 (2016).
23. Arias, A. S., Rucavado, A. & Gutiérrez, J. M. Peptidomimetic hydroxamate metalloproteinase inhibitors abrogate local and systemic toxicity induced by *Echis ocellatus* (saw-scaled) snake venom. *Toxicon* 132, 40-49 (2017).
24. Rucavado, A. et al. Inhibition of local hemorrhage and dermonecrosis induced by *Bothrops asper* snake venom: effectiveness of early in situ administration of the peptidomimetic metalloproteinase inhibitor batimastat and the chelating agent CaNa2EDTA. *Am. J. Trop. Med. Hyg.* 63, 313-319 (2000).
25. Ainsworth, S. et al. The paraspecific neutralisation of snake venom induced coagulopathy by antivenoms. *Commun. Biol.* 1, 34 (2018).
26. Lewin, M. et al. Delayed LY333013 (Oral) and LY315920 (Intravenous) reverse severe neurotoxicity and rescue juvenile pigs from lethal doses of *Micrurus fulvius* (Eastern coral snake) venom. *Toxins* (Basel). 10, 479 (2018).
27. Lewin, M. et al. Delayed oral LY333013 rescues mice from highly neurotoxic, lethal doses of Papuan taipan (*Oxyuranus scutellatus*) venom. *Toxins* (Basel). 10, 380 (2018).
28. Albulescu, L.-O. et al. Preclinical validation of a repurposed metal chelator as an early-intervention therapeutic for hemotoxic snakebite. *Sci. Trans. Med.* 12, eaay8314 (2020).
29. Wang, Y. et al. Exploration of the inhibitory potential of varespladib for snakebite envenomation. *Molecules* 23, 391 (2018).
30. Layfield, H. J. et al. Repurposing cancer drugs batimastat and marimastat to inhibit the activity of a group I metalloprotease from the venom of the Western diamondback rattlesnake, *Crotalus atrox*. *Toxins* 12, 309 (2020).
31. Rowsell, S. et al. Crystal structure of human MMP9 in complex with a reverse hydroxamate inhibitor. *J. Mol. Biol.* 319, 173-81 (2002).
32. Warrell, D. A. & Arnett, C. The importance of bites by the saw scaled or carpet viper (*Echis carinatus*): Epide- 32. miological studies in Nigeria and a review of the world. *Acta Trop.* 33, 307-341 (1976).
33. Warrell, D. Clinical Toxicology of Snakebite in Asia. in *Handbook of Clinical Toxicology of Animal Venoms and Poisons* (eds. White, J. & Meier, J.) pp. 534-594 (CRC Press, 1995).
34. Warrell, D. Clinical Toxicology of Snakebite in Africa and the Middle East/Arabian Peninsula. in *Handbook of Clinical Toxicology of Animal Venoms and Poisons* (eds. White, J. & Meier, J.) pp. 455-492 (CRC Press, 1995).
35. Still, K. et al. Multipurpose HTS Coagulation Analysis: Assay Development and Assessment of Coagulopathic Snake Venoms. *Toxins* (Basel). 9, 382 (2017).
36. Rogalski, A. et al. Differential procoagulant effects of saw-scaled viper (Serpentes: Viperidae: *Echis*) snake venoms on human plasma and the narrow taxonomic ranges of antivenom efficacies. *Toxicol. Lett.* 280, 159-170 (2017).
37. Slagboom, J. et al. High throughput screening and identification of coagulopathic snake venom proteins and peptides using nanofractionation and proteomics approaches. *PLoS Negl. Trop. Dis.* 14, e0007802 (2020).
38. Winer, A., Adams, S. & Mignatti, P. Matrix metalloproteinase inhibitors in cancer therapy: turning past failures into future successes. *Mol. Cancer Ther.* 17, 1147-1155 (2018).
39. Kim, E. Y. et al. Low-dose nafamostat mesilate in hemodialysis patients at high bleeding risk. *Kidney Res. Clin. Pract.* 30, 61-66 (2011).
40. Kim, H. S. et al. Cardiac arrest caused by nafamostat mesilate. *Kidney Res. Clin. Pract.* 35, 187-189 (2016).
41. Theakston, R. D. & Reid, H. A. Development of simple standard assay procedures for the characterization of snake venom. *Bull. World Health Organ.* 61, 949-56 (1983).
42. Harrison, R. A. et al. Preclinical antivenom-efficacy testing reveals potentially disturbing deficiencies of snakebite treatment capability in East Africa. *PLoS Negl. Trop. Dis.* 11, e0005969 (2017).
43. WHO|WHO Guidelines for the Production, Control and Regulation of Snake Antivenom Immunoglobulins. *WHO* (2018).
44. Bolanos, R. Toxicity of Costa Rican snake venoms for the white mouse. *Am. J. Trop. Med. Hyg.* 21, 360-363 (1972).
45. Villalta, M. et al. Development of a new polyspecific antivenom for snakebite envenoming in Sri Lanka: Analysis of its preclinical efficacy as compared to a currently available antivenom. *Toxicon* 122, 152-159 (2016).
46. Mora-Obando, D. et al. Proteomic and functional profiling of the venom of *Bothrops ayerbei* from Cauca, Colombia, reveals striking interspecific variation with *Bothrops asper* venom. *J. Proteomics* 96, 159-172 (2014).
47. Harrison, R. A. & Gutiérrez, J. M. Priority actions and progress to substantially and sustainably reduce the mortality, morbidity and socioeconomic burden of tropical snakebite. *Toxins* (Basel). 8, 351 (2016).
48. de la Rosa, G. et al. Horse immunization with short-chain consensus α-neurotoxin generates antibodies against broad spectrum of elapid venomous species. *Nat. Commun.* 10, 3642 (2019).
49. Kini, R. M., Sidhu, S. S. & Laustsen, A. H. Biosynthetic oligoclonal antivenom (BOA) for snakebite and next-generation treatments for snakebite victims. *Toxins* (Basel). 10, 534 (2018).
50. Laustsen, A. H. et al. In vivo neutralization of dendrotoxin-mediated neurotoxicity of black mamba venom by oligoclonal human IgG antibodies. *Nat. Commun.* 9, 3928 (2018).
51. Peterson, J. The importance of estimating the therapeutic index in the development of matrix metalloproteinase inhibitors. *Cardiovasc. Res.* 69, 677-687 (2006).
52. Millar, A. W. et al. Results of single and repeat dose studies of the oral matrix metalloproteinase inhibitor marimastat in healthy male volunteers. *Br. J. Clin. Pharmacol.* 45, 21-6 (1998).
53. Rosemurgy, A. et al. Marimastat in patients with advanced pancreatic cancer: a dose-finding study. *Am. J. Clin. Oncol.* 22, 247-52 (1999).
54. Nair, A. & Jacob, S. A simple practice guide for dose conversion between animals and human. *J. Basic Clin. Pharm.* 7, 27 (2016).
55. Varespladib. *Am. J. Cardiovasc. Drugs* 11, 137-143 (2011).
56. Rosenson, R. S. et al. Effects of varespladib methyl on biomarkers and major cardiovascular events in acute coronary syndrome patients. *J. Am. Coll. Cardiol.* 56, 1079-1088 (2010).
57. Abraham, E. et al. Efficacy and safety of LY315920Na/S-5920, a selective inhibitor of 14-kDa group IIA secretory phospholipase A2, in patients with suspected sepsis and organ failure. *Crit. Care Med.* 31, 718-728 (2003).
58. Nicholls, S. J. et al. Varespladib and cardiovascular events in patients with an acute coronary syndrome: The VISTA-16 randomized clinical trial. *JAMA—J. Am. Med. Assoc.* 311, 252-262 (2014).
59. Gutiérrez, J. M., Lewin, M. R., Williams, D. J. & Lomonte, B. Varespladib (LY315920) and methyl varespladib (LY333013) abrogate or delay lethality induced by presynaptically acting neurotoxic snake venoms. *Toxins* (Basel). 12, 131 (2020).
60. Ohtake, Y. et al. Nafamostat mesylate as anticoagulant in continuous hemofiltration and continuous hemodiafiltration. *Contrib. Nephrol.* 93, 215-217 (1991).
61. Maiorino, R. M., Xu, Z. F. & Aposhian, H. V. Determination and metabolism of dithiol chelating agents. XVII. In humans, sodium 2,3-dimercapto-1-propanesulfonate is bound to plasma albumin via mixed disulfide formation and is found in the urine as cyclic polymeric disulfides. *J. Pharmacol. Exp. Ther.* 277, 375-84 (1996).
62. Kosnett, M. J. The role of chelation in the treatment of arsenic and mercury poisoning. *J. Med. Toxicol.* 9, 347-354 (2013).
63. Wagstaff, S. C., Sanz, L., Juarez, P., Harrison, R. A. & Calvete, J. J. Combined snake venomics and venom gland transcriptomic analysis of the ocellated carpet viper, *Echis ocellatus. J. Proteomics* 71, 609-623 (2009).
64. Tan, N. H. et al. Functional venomics of the Sri Lankan Russell's viper (*Daboia russelii*) and its toxinological correlations. *J. Proteomics* 128, 403-423 (2015).
65. Pla, D. et al. Phylovenomics of *Daboia russelii* across the Indian subcontinent.
Bioactivities and comparative in vivo neutralization and in vitro third-generation antivenomics of antivenoms against venoms from India, Bangladesh and Sri Lanka. *J. Proteomics* 207, 103443 (2019).
66. Bradley, J. D. et al. A randomized, double-blinded, placebo-controlled clinical trial of LY333013, a selective inhibitor of group II secretory phospholipase A2, in the treatment of rheumatoid arthritis. *J. Rheumatol.* 32, 417-423 (2005).

67. Sevenet, P. O. & Depasse, F. Clot waveform analysis: Where do we stand in 2017? *Int. J. Lab. Hematol.* 39, 561-568 (2017).
68. Patra, A., Kalita, B., Chanda, A. & Mukherjee, A. K. Proteomics and antivenomics of *Echis carinatus carinatus* venom: Correlation with pharmacological properties and pathophysiology of envenomation. *Sci. Rep.* 7, 1-17 (2017).
69. Alape-Giron, A. et al. Studies on the venom proteome of *Bothrops asper* perspectives and applications. *Toxicon* 54, 938-948 (2009).
70. Calvete, J. J., Escolano, J. & Sanz, L. Snake venomics of *Bitis* species reveals large intragenus venom toxin composition variation: application to taxonomy of congeneric taxa. *J. Proteome Res.* 6, 2732-2745 (2007).

What is claimed is:

1. A method of treating snake bite, the method comprising administering to a subject in need of such treatment a combination comprising varespladib and DMPS in therapeutically effective amounts, wherein the varespladib and DMPS are administered simultaneously or sequentially and wherein the snake bite is from a snake native to North America.

2. The method according to claim 1, wherein varespladib and DMPS are provided in the same composition or in separate compositions.

3. The method according to claim 1, wherein the subject is administered a combination of varespladib, marimastat, and DMPS.

4. The method according to claim 3, wherein varespladib, marimastat, and DMPS are provided in the same composition or in separate compositions.

5. The method according to claim 3, wherein varespladib, marimastat, and DMPS are administered orally, topically, and/or by injection.

6. The method according to claim 3, wherein varespladib, marimastat, and DMPS are administered sequentially.

7. The method according to claim 3, wherein the snake bite is from a snake of a genus selected from the group consisting of: *Crotalus, Sistrurus, Agkistrodon, Micrurus,* and *Micruroides*.

8. The method according to claim 7, wherein the snake bite is from a snake selected from the group consisting of: *Crotalus atrox, Crotalus adamanteus, Crotalus cerastes, Crotalus enyo, Crotalus horridus, Crotalus lepidus, Crotalus mitchellii, Crotalus molossus, Crotalus pricei, Crotalus ruber, Crotalus scutulatus, Crotalus tigris, Crotalus viridis, Crotalus willardi, Sistrurus militaries,* and *Agkistrodon contortrix*.

9. The method according to claim 7, wherein the snake bite is from a snake selected from the group consisting of: *Crotalus atrox, Crotalus scutulatus, Crotalus adamaneus, Crotalus horridus, Sistrurus miliarius,* and *Agkistrodon contortrix*.

10. The method according to claim 1, wherein varespladib and DMPS are administered orally, topically, and/or by injection.

11. The method according to claim 1, wherein the snake bite is from a snake of a genus selected from the group consisting of: *Crotalus, Sistrurus, Agkistrodon, Micrurus,* and *Micruroides*.

12. The method according to claim 11, wherein the snake bite is from a snake selected from the group consisting of: *Crotalus atrox, Crotalus adamanteus, Crotalus cerastes, Crotalus enyo, Crotalus horridus, Crotalus Lepidus, Crotalus mitchellii, Crotalus molossus, Crotalus pricei, Crotalus ruber, Crotalus scutulatus, Crotalus tigris, Crotalus viridis, Crotalus willardi, Sistrurus militaries,* and *Agkistrodon contortrix*.

13. The method according to claim 11, wherein the snake bite is from a snake selected from the group consisting of: *Crotalus atrox, Crotalus scutulatus, Crotalus adamanteus, Crotalus horridus, Sistrurus miliarius,* and *Agkistrodon contortrix*.

14. A pharmaceutical composition comprising a therapeutically effective amount of a combination of varespladib, DMPS, and a pharmaceutically acceptable carrier.

15. The pharmaceutical composition according to claim 14, which is adapted for administration orally, topically, or by injection.

16. A kit for treating a North American snake bite, the kit comprising a therapeutically effective amount of varespladib and DMPS.

17. The kit according to claim 16, wherein varespladib and DMPS are in separate compositions.

18. The kit according to claim 16, wherein varespladib and DMPS are in the same composition.

19. The kit according to claim 16, wherein varespladib and DMPS are formulated for oral, topical, and/or injection administration.

20. A kit for treating a North American snake bite, the kit comprising a therapeutically effective amount of varespladib, marimastat, and DMPS.

21. The kit according to claim 20, wherein varespladib, marimastat, and DMPS are in separate compositions.

22. The kit according to claim 20, wherein varespladib, marimastat, and DMPS are in the same composition.

23. The kit according to claim 20, wherein varespladib, marimastat, and DMPS are formulated for oral, topical, and/or injection administration.

24. A pharmaceutical composition comprising a therapeutically effective amount of a combination of varespladib, marimastat, DMPS, and a pharmaceutically acceptable carrier.

25. The pharmaceutical composition according to claim 24, which is adapted for administration orally, topically, or by injection.

* * * * *